US008759493B2

(12) United States Patent
Zavada et al.

(10) Patent No.: US 8,759,493 B2
(45) Date of Patent: **\*Jun. 24, 2014**

(54) MN GENE AND PROTEIN

(75) Inventors: Jan Zavada, Prague (CZ); Silvia Pastorekova, Bratislava (SK); Jaromir Pastorek, Bratislava (SK)

(73) Assignee: Institute of Virology Slovak Academy of Sciences, Bratislava (SK)

( * ) Notice: Subject to any disclaimer, the term of this patent is extended or adjusted under 35 U.S.C. 154(b) by 1739 days.

This patent is subject to a terminal disclaimer.

(21) Appl. No.: 11/930,041

(22) Filed: Oct. 30, 2007

(65) Prior Publication Data

US 2011/0319599 A1    Dec. 29, 2011

Related U.S. Application Data

(63) Continuation of application No. 10/795,933, filed on Mar. 8, 2004, now abandoned, which is a continuation of application No. 08/260,190, filed on Jun. 15, 1994, now Pat. No. 6,774,117, which is a continuation-in-part of application No. 08/177,093, filed on Dec. 30, 1993, now Pat. No. 6,051,226, which is a continuation-in-part of application No. 07/964,589, filed on Oct. 21, 1992, now Pat. No. 5,387,676.

(30) Foreign Application Priority Data

Mar. 11, 1992   (CZ) .......................................  709-92

(51) Int. Cl.
*C07K 14/00*   (2006.01)
*C07K 16/00*   (2006.01)
*C07K 17/00*   (2006.01)
*A61K 35/14*   (2006.01)
*C12P 21/08*   (2006.01)
*C12N 5/00*    (2006.01)
*C12N 5/02*    (2006.01)

(52) U.S. Cl.
USPC ........ 530/387.9; 530/350; 530/380; 530/386; 530/387.1; 530/387.3; 530/388.1; 435/320.1

(58) Field of Classification Search
None
See application file for complete search history.

(56) References Cited

U.S. PATENT DOCUMENTS 5,348,880 A * 9/1994 Hanna et al. ............... 435/344.1

FOREIGN PATENT DOCUMENTS

WO   WO 88/08854   11/1988
WO   WO 93/18152    9/1993

OTHER PUBLICATIONS

Huse et al. (Science 246: 1275-1281, Dec. 8, 1989).*

Divgi et al., "Scintgraphy of Renal Carcinoma with 1-131 Labelled Monoclonal Antibody (MAB) G250, "*European Journal of Nuclear Medicine*, 19(8): 578 (Abstact 121-3) (Aug. 23, 1992).
Frohman et al., "Rapid production of full-length cDNAs from rare transcripts: Amplification using a single gene-specific oligonucleotide primer, "*PNAS* (USA), 85: 8998-9002 (Dec. 1988).
Frosch et al, "Cloning and Characterisation of an Immunodominant Major Surface Antigen of *Echinococcus multilocularis*", *Molecular and Biochemical Parasitology*, 48: 121-130 (1991).
Kurth et al., "Characterization of Human Renal Cell Carcinoma Tumor Lines by Means of Monoclonal Antibodies," *Prostate*, 6(4): 451 (Abstract) (1985).
Oosterwijk et al., "The Expression of Renal Antigens in Renal Cell Carcinoma," World Journal of Urology, 2(2):156-158 (1984).
Oosterwijk et al., "Monoclonal Antibodies that Discriminate Between Renal Cell Carcinomas (RCC) and Other Malignancies," *Prostate*, 6(4): 451-452 (1985).
Oosterwijk et al., "Immunohistochemical Analysis of Monoclonal Antibodies to Renal Antigens—Application in the Diagnosis of Renal Cell Carcinoma," *American Journal of Pathology*, 123(2): 301-309 (May 1986).
Oosterwijk et al., "Monoclonal Antibody G250 Recognizes a Determinant Present in Renal-Cell Carcinoma and Absent from Normal Kidney," *Int. J. Cancer*, 38: 489-494 (1986).
Oosterwijk et al., "Relationship Between DNA Ploidy, Antigen Expression and Survival in Renal Cell Carcinoma,"*Int. J. Cancer*, 42: 703-708 (1988).
Oosterwijk et al., "Expression of Intermediate-sized Filaments in Developing and Adult Human Kidney and Renal Cell Carcinoma," *The Journal of Histochemistry and Cytochemistry*, 38(3): 385-392 (1990).
Oosterwijk et al., "Antibody Localization in Human Renal Cell Carcinoma: A Phase I Study of Monoclonal Antibody G250," *Journal of Clinical Oncology*, 11(4): 738-750 (Apr. 1993).
Oosterwijk et 21., "Molecular characterization of the Renal Cell Carcinoma-Associated Antigen G250," *Proceedings of the American Association for Cancer Research*, 37: 461 (Mar. 1996).
Pastorekova et al "A Novel Quasi-viral Agent, MaTU, Is a Two -Component System," *Virology*, 187: 620-626 (1992).
Stanbridge et al., "Specific Chromosome Loss Associated with the Expression of Tumorigenicity in Human Cell Hybrids," *Somatic Cell Genetics*, 7(6): 699-712 (1981).

(Continued)

*Primary Examiner* — Alana Harris Dent
(74) *Attorney, Agent, or Firm* — Millen, White, Zelano, Branigan, P.C.

(57) ABSTRACT

A new gene —MN— and proteins/polypeptides encoded therefrom are disclosed. Recombinant nucleic acid molecules for expressing MN proteins/polypeptides and recombinant proteins are provided. Expression of the MN gene is disclosed as being associated with tumorigenicity, and the invention concerns methods and compositions for detecting and/or quantitating MN antigen and/or MN-specific antibodies in vertebrate samples that are diagnostic/prognostic for neoplastic and pre-neoplastic disease. MN-specific antibodies are disclosed that can be used diagnostically/prognostically, therapeutically, for imaging, and/or for affinity purification of MN proteins/polypeptides. The invention still further concerns antisense nucleic acid sequences that can be used to inhibit MN gene expression.

29 Claims, 26 Drawing Sheets

(56) References Cited

OTHER PUBLICATIONS

Stanbridge et al, "Human Cell Hybrids: Analysis of transformation and Tumorigenicity", *Science.* 215: 252-259 (Jan. 15, 1982).

Tweedie and Edwards, "Mouse Carbonic Anhydrase III:Nucleotide Sequence and Expression Studies", *Biochemical Genetics.* 27(1/2): 17-30 (1989)

Uemura et al. "Internal Image Anti-Idiotype Antibodies Related to Renal-Cell Carcinoma-Associated Antigen G250,"*Int. J. Cancer,* 56: 609-614 (1994).

Uemura et al. "Expression of Tumor-Associated Antigen MN/G250 in Urologic Carcinoma: Potential Therapeutic Target," *Journal Urology,* 157 (4 Supp.): 377 (Apr. 16, 1997).

Van Dijk et al., "Therapeutic Effects of Monoclonal Antibody G250, Interferons and Tumor Necrosis Factor, in Mice with Renal-Cell Carcinoma Xenografts," *Int. J. Cancer,* 56: 262-268 (1994).

Young and Davis, "Efficient Isolation of Genes by Using Antibody Probes", *PNAS* (USA) 80: 1194-1198 (Mar. 1983).

Zavada, "The Pseudotypic Paradox", *J. gen. Virol.*; 63: 15-24 (1982).

Zavada and Zavadova, "A Transmissible Antigen Detected in Two Cell Lines Derived front Human Tumours", *J. gen. Virol.,* 24: 327-337 (1974).

Zavada and Zavadova, "An unusual transmissible agent—MaTu",*Arch. Virol.,* 118: 189-197 (1991).

Zavada et al., "VSV Pseudotvpe Produced in Cell Line derived from Human Mammary Carcinoma", *Nature New Biology,* 240: 124-125 (Nov. 22, 1972).

Zavada et al., "Tumorigenicity-Related Expression of MaTu Proteins in HeLa x Fibroblast Hybrids", Abstract presented at the XIX Meeting of the European Tumor Virus Group (May 1-4, 1991).

Zavada et al., "Expression of MaTu-MN Protein in Human Tumor Cultures and in Clinical Specimens" *Int. J. Cancer,* 54: 268-274 (1993).

* cited by examiner

```
  1  Gln Arg Leu Pro Arg Met Gln Glu Asp Ser Pro Leu Gly Gly Gly
  1  CAG AGG TTG CCC CGG ATG CAG GAG GAT TCC CCC TTG GGA GGA GGC

16  Ser Ser Gly Glu Asp Asp Pro Leu Gly Glu Glu Asp Leu Pro Ser
 46  TCT TCT GGG GAA GAT GAC CCA CTG GGC GAG GAG GAT CTG CCC AGT

31  Glu Glu Asp Ser Pro Arg Glu Glu Asp Pro Pro Gly Glu Glu Asp
 91  GAA GAG GAT TCA CCC AGA GAG GAG GAT CCA CCC GGA GAG GAG GAT

46  Leu Pro Gly Glu Glu Asp Leu Pro Gly Glu Glu Asp Leu Pro Glu
136  CTA CCT GGA GAG GAG GAT CTA CCT GGA GAG GAG GAT CTA CCT GAA

61  Val Lys Pro Lys Ser Glu Glu Glu Gly Ser Leu Lys Leu Glu Asp
181  GTT AAG CCT AAA TCA GAA GAA GAG GGC TCC CTG AAG TTA GAG GAT

76  Leu Pro Thr Val Glu Ala Pro Gly Asp Pro Gln Glu Pro Gln Asn
226  CTA CCT ACT GTT GAG GCT CCT GGA GAT CCT CAA GAA CCC CAG AAT

91  Asn Ala His Arg Asp Lys Glu Gly Asp Asp Gln Ser His Trp Arg
271  AAT GCC CAC AGG GAC AAA GAA GGG GAT GAC CAG AGT CAT TGG CGC

106  Tyr Gly Gly Asp Pro Pro Trp Pro Arg Val Ser Pro Ala Cys Ala
316  TAT GGA GGC GAC CCG CCC TGG CCC CGG GTG TCC CCA GCC TGC GCG

121  Gly Arg Phe Gln Ser Pro Val Asp Ile Arg Pro Gln Leu Ala Ala
361  GGC CGC TTC CAG TCC CCG GTG GAT ATC CGC CCC CAG CTC GCC GCC

136  Phe Cys Pro Ala Leu Arg Pro Leu Glu Leu Leu Gly Phe Gln Leu
406  TTC TGC CCG GCC CTG CGC CCC CTG GAA CTC CTG GGC TTC CAG CTC

151  Pro Pro Leu Pro Glu Leu Arg Leu Arg Asn Asn Gly His Ser Val
451  CCG CCG CTC CCA GAA CTG CGC CTG CGC AAC AAT GGC CAC AGT GTG

166  Gln Leu Thr Leu Pro Pro Gly Leu Glu Met Ala Leu Gly Pro Gly
496  CAA CTG ACC CTG CCT CCT GGG CTA GAG ATG GCT CTG GGT CCC GGG

191  Arg Glu Tyr Arg Ala Leu Gln Leu His Leu His Trp Gly Ala Ala
541  CGG GAG TAC CGG GCT CTG CAG CTG CAT CTG CAC TGG GGG GCT GCA

196  Gly Arg Pro Gly Ser Glu His Thr Val Glu Gly His Arg Phe Pro
586  GGT CGT CCG GGC TCG GAG CAC ACT GTG GAA GGC CAC CGT TTC CCT

211  Ala Glu Ile His Val Val His Leu Ser Thr Ala Phe Ala Arg Val
631  GCC GAG ATC CAC GTG GTT CAC CTC AGC ACC GCC TTT GCC AGA GTT
```

FIG. 1A

```
226  Asp Glu Ala Leu Gly Arg Pro Gly Gly Leu Ala Val Leu Ala Ala
676  GAC GAG GCC TTG GGG CGC CCG GGA GGC CTG GCC GTG TTG GCC GCC

241  Phe Leu Glu Glu Gly Pro Glu Glu Asn Ser Ala Tyr Glu Gln Leu
721  TTT CTG GAG GAG GGC CCG GAA GAA AAC AGT GCC TAT GAG CAG TTG

256  Leu Ser Arg Leu Glu Glu Ile Ala Glu Glu Gly Ser Glu Thr Gln
766  CTG TCT CGC TTG GAA GAA ATC GCT GAG GAA GGC TCA GAG ACT CAG

271  Val Pro Gly Leu Asp Ile Ser Ala Leu Leu Pro Ser Asp Phe Ser
811  GTC CCA GGA CTG GAC ATA TCT GCA CTC CTG CCC TCT GAC TTC AGC

286  Arg Tyr Phe Gln Tyr Glu Gly Ser Leu Thr Thr Pro Pro Cys Ala
856  CGC TAC TTC CAA TAT GAG GGG TCT CTG ACT ACA CCG CCC TGT GCC

301  Gln Gly Val Ile Trp Thr Val Phe Asn Gln Thr Val Met Leu Ser
901  CAG GGT GTC ATC TGG ACT GTG TTT AAC CAG ACA GTG ATG CTG AGT

316  Ala Lys Gln Leu His Thr Leu Ser Asp Thr Leu Trp Gly Pro Gly
946  GCT AAG CAG CTC CAC ACC CTC TCT GAC ACC CTG TGG GGA CCT GGT

331  Asp Ser Arg Leu Gln Leu Asn Phe Arg Ala Thr Gln Pro Leu Asn
991  GAC TCT CGG CTA CAG CTG AAC TTC CGA GCG ACG CAG CCT TTG AAT

346  Gly Arg Val Ile Glu Ala Ser Phe Pro Ala Gly Val Asp Ser Ser
1046 GGG CGA GTG ATT GAG GCC TCC TTC CCT GCT GGA GTG GAC AGC AGT

361  Pro Arg Ala Ala Glu Pro Val Gln Leu Asn Ser Cys Leu Ala Ala
1081 CCT CGG GCT GCT GAG CCA GTC CAG CTG AAT TCC TGC CTG GCT GCT

376  Gly Asp Ile Leu Ala Leu Val Phe Gly Leu Leu Phe Ala Val Thr
1126 GGT GAC ATC CTA GCC CTG GTT TTT GGC CTC CTT TTT GCT GTC ACC

391  Ser Val Ala Phe Leu Val Gln Met Arg Arg Gln His Arg Arg Gly
1171 AGC GTC GCG TTC CTT GTG CAG ATG AGA AGG CAG CAC AGA AGG GGA

406  Thr Lys Gly Gly Val Ser Tyr Arg Pro Ala Glu Val Ala Glu Thr
1216 ACC AAA GGG GGT GTG AGC TAC CGC CCA GCA GAG GTA GCC GAG ACT

421  Gly Ala
1261 GGA GCC TAG AGG CTG GAT CTT GGA GAA TGT GAG AAG CCA GCC AGA

1306 GGC ATC TGA GGG GGA GCC GGT AAC TGT CCT GTC CTG CTC ATT ATG

1351 CCA CTT CCT TTT AAC TGC AAA GAA ATT TTT TAA AAT AAA TAT TTA

1396 TAA T
```

FIG. 1B

| | | | | | | | | | | | | | | | | |
|---|---|---|---|---|---|---|---|---|---|---|---|---|---|---|---|---|
| 349 | V | M | L | S | A | K | Q | L | H | T | L | S | D | T | L | W | 364 |
| 1057 | GTG | ATG | CTG | AGT | GCT | AAG | CAG | CTC | CAC | ACC | CTC | TCT | GAC | ACC | CTG | TGG | 1104 |
| 365 | G | P | G | D | S | R | L | Q | L | N | F | R | A | T | Q | P | 380 |
| 1105 | GGA | CCT | GGT | GAC | TCT | CGG | CTA | CAG | CTG | AAC | TTC | CGA | GCG | ACG | CAG | CCT | 1152 |
| 381 | L | N | G | R | V | I | E | A | S | F | P | A | G | V | D | S | 396 |
| 1153 | TTG | AAT | GGG | CGA | GTG | ATT | GAG | GCC | TCC | TTC | CCT | GCT | GGA | GTG | GAC | AGC | 1200 |
| 397 | S | P | R | A | A | E | P | V | Q | L | N | S | C | L | A | A | 412 |
| 1201 | AGT | CCT | CGG | GCT | GCT | GAG | CCA | GTC | CAG | CTG | AAT | TCC | TGC | CTG | GCT | GCT | 1248 |
| 413 | G | D | I | L | A | L | V | F | G | L | F | A | V | T | S | 428 |
| 1249 | GGT | GAC | ATC | CTA | GCC | CTG | GTT | TTT | GGC | CTC | TTT | GCT | GTC | ACC | AGC | 1296 |
| 429 | V | A | F | L | V | Q | M | R | R | Q | H | R | R | G | T | K | 444 |
| 1297 | GTC | GCG | TTC | CTT | GTG | CAG | ATG | AGA | AGG | CAG | CAC | AGA | AGG | GGA | ACC | AAA | 1344 |
| 445 | G | G | V | S | Y | R | P | A | E | V | A | E | T | G | A | * | 460 |
| 1345 | GGG | GGT | GTG | AGC | TAC | CGC | CCA | GCA | GAG | GTA | GCC | GAG | ACT | GGA | GCC | TAG | 1392 |
| 1393 | AGG | CTG | GAT | CTT | GGA | GAA | TGT | CCT | GTC | CTG | CTC | ATT | ATG | CCA | CTT | TGA | GGG | 1440 |
| 1441 | GGA | GCC | GGT | AAC | TGT | CCT | GTC | CTG | CTC | ATT | ATG | CCA | CTT | CCT | TTT | AAC | 1488 |
| 1489 | TGC | CAA | GAA | ATT | TTT | TAA | AAT | AAA | TAT | TTA | TAA | T | | | | | 1522 |

| | | | | | | | | | | | | |
|---|---|---|---|---|---|---|---|---|---|---|---|---|
| 1 1 | ACA | | | M ATG | A GCT | P CCC | L CTG | C TGC | P CCC | S AGC | P CCC | W TGG | L CTC | P CCT | L CTG | 12 48 |
| 13 49 | L TTG | I ATC | P CCG | A GCC | P CCT | A GCT | P CCA | G GGC | L CTC | T ACT | V GTG | Q CAA | L CTG | L CTG | S TCA | 28 96 |
| 29 97 | L CTG | L CTG | L CTT | M ATG | L CTG | M ATG | P CCT | V GTC | H CAT | P CCC | Q CAG | R AGG | L CTG | R CGG | M ATG | Q CAG | 44 144 |
| 45 145 | E GAG | D GAT | S TCC | P CCC | P CCT | V GTC | G GGC | G GGA | S TCT | S TCT | G GGG | E GAA | E GAG | D GAC | P CCA | L CTG | 60 192 |
| 61 193 | G GGC | E GAG | E GAG | D GAT | P CCC | L CTG | P CCC | S AGT | D GAT | E GAG | E GAG | E GAG | R AGA | E GAG | E GAG | D GAT | 76 240 |
| 77 241 | P CCA | G GGA | E GAG | E GAG | D GAT | L CTA | P CCT | K AAG | V GTT | P CCT | K AAA | S TCA | E GAG | G GGA | L CTA | E GAG | 92 288 |
| 93 289 | E GAG | L CTA | P CCT | E GAA | V GTT | K AAG | P CCT | T ACT | V GTT | E GAG | A GCT | S TCA | E GAA | E GAA | G GGA | L CTG | 108 336 |
| 109 337 | K AAG | L CTA | E GAG | D GAT | L CTA | D GAT | H CAC | R AGG | D GAC | K AAA | A GAA | E GAG | P CCT | D GAT | D GAT | E GAA | 124 384 |
| 125 385 | P CCC | Q CAG | N AAT | N AAT | A GCC | D GAC | P CCC | P CCC | W TGG | E GAA | P CCC | D GAT | D GAC | S TCC | Q CAG | H CAT | 140 432 |
| 141 433 | W TGG | R CGC | Y TAT | G GGA | G GGC | D GAC | R CGG | P CCC | V GTG | R CGG | V GTG | S TCC | P CCA | R CGG | A GCC | C TGC | 156 480 |
| 157 481 | A GCG | G GGC | R CGC | F TTC | Q CAG | S TCC | F TTC | V GTG | D GAT | I ATC | R CGC | P CCC | Q CAG | L CTC | A GCC | A GCC | 172 528 |

FIG. 15A

| | | | | | | | | | | | | | | | | |
|---|---|---|---|---|---|---|---|---|---|---|---|---|---|---|---|---|
| 173 | F | C | P | A | L | R | P | L | E | L | L | G | F | Q | L | P | 188 |
| 529 | TTC | TGC | CCG | GCC | CTG | CGC | CCC | CTG | GAA | CTC | CTG | GGC | TTC | CAG | CTC | CCG | 576 |
| 189 | P | L | P | E | L | R | L | R | N | N | A | H | S | V | Q | L | 204 |
| 577 | CCG | CTC | CCA | GAA | CTG | CGC | CTG | CGC | AAC | AAT | GCC | CAC | AGT | GTG | CAA | CTG | 624 |
| 205 | T | L | P | P | G | L | E | M | A | L | G | P | A | R | E | Y | 220 |
| 625 | ACC | CTG | CCT | CCT | GGG | CTA | GAG | ATG | GCT | CTG | GGT | CCC | GCA | CGG | GAG | TAC | 672 |
| 221 | R | A | L | Q | H | L | H | L | H | W | G | A | A | G | R | P | G | 236 |
| 673 | CGG | GCT | CTG | CAG | CAT | CTG | CAC | TGG | GGG | GCT | GCA | GGT | CGT | CCG | GGC | 720 |
| 237 | S | E | H | T | V | T | V | E | G | H | R | F | P | A | E | I | H | V | 252 |
| 721 | TCG | GAG | CAC | ACT | GTG | ACT | GTG | GAA | GGC | CAC | CGT | TTC | CCT | GCC | GAG | ATC | CAC | GTG | 768 |
| 253 | V | H | L | S | T | A | F | A | R | V | D | E | A | L | G | R | 268 |
| 769 | GTT | CAC | CTC | AGC | ACC | GCC | TTT | GCC | AGA | GTT | GAC | GAG | GCC | TTG | GGG | CGC | 816 |
| 269 | P | G | G | L | A | V | L | A | A | F | L | E | E | G | P | E | 284 |
| 817 | CCG | GGA | GGC | CTG | GCC | GTG | TTG | GCC | GCC | TTT | CTG | GAG | GAG | GGC | CCG | GAA | 864 |
| 285 | E | N | S | A | Y | E | Q | L | L | S | R | L | E | E | I | A | 300 |
| 865 | GAA | AAC | AGT | GCC | TAT | GAG | CAG | TTG | CTG | TCT | CGC | CTG | GAA | GAA | ATC | GCT | 912 |
| 301 | E | G | S | E | T | Q | V | P | G | L | D | I | S | A | L | 316 |
| 913 | GAG | GAA | GGC | TCA | GAG | ACT | CAG | GTC | CCA | GGA | CTG | GAC | ATA | TCT | GCA | CTC | 960 |
| 317 | L | P | S | D | F | S | R | Y | F | Q | Y | E | G | S | L | T | 332 |
| 961 | CTG | CCC | TCT | GAC | TTC | AGC | CGC | TAC | TTC | CAA | TAT | GAG | GGG | TCT | CTG | ACT | 1008 |
| 333 | T | P | P | C | A | Q | G | V | I | W | T | V | F | N | Q | T | 348 |
| 1009 | ACA | CCG | CCC | TGT | GCC | CAG | GGT | GTC | ATC | TGG | ACT | GTG | TTT | AAC | CAG | ACA | 1056 |

FIG. 15B

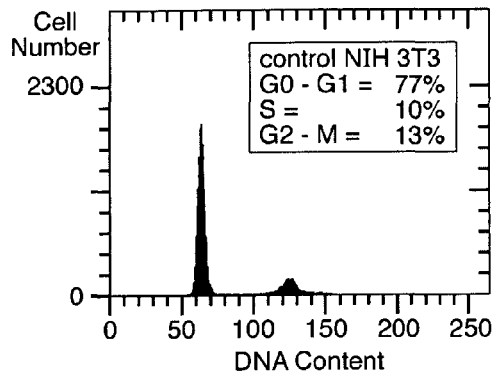
FIG._24A-1
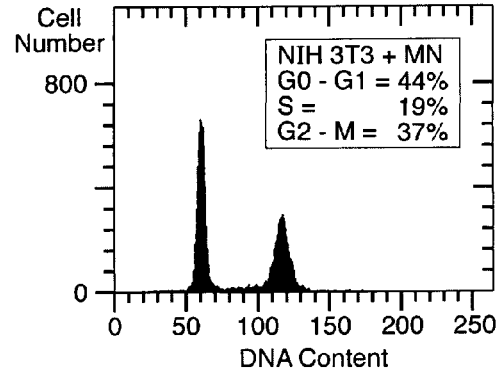
FIG._24A-2
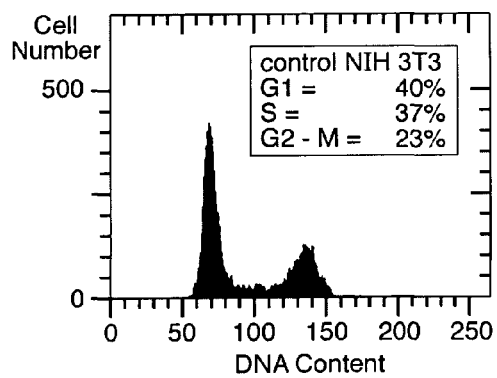
FIG._24B-1
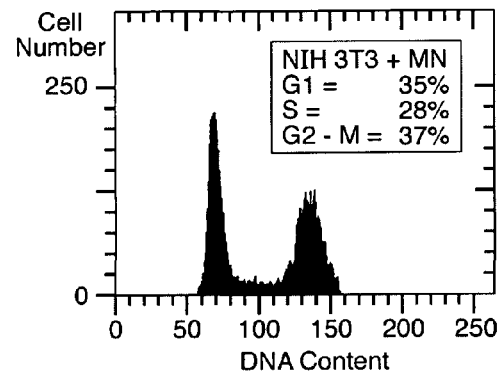
FIG._24B-2
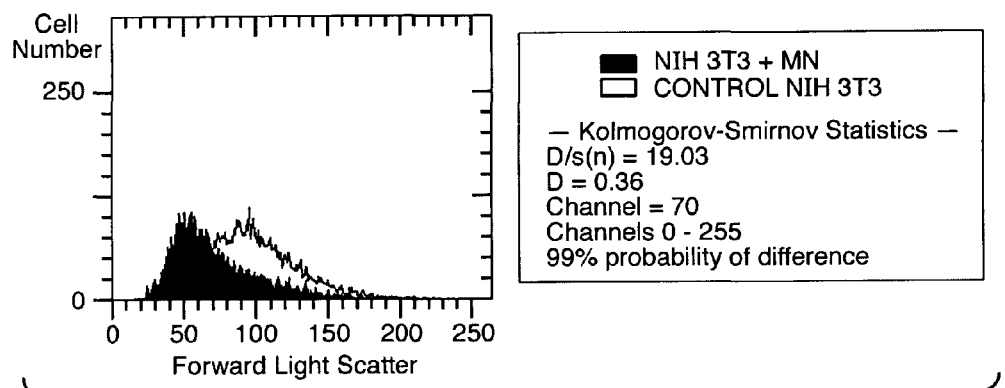
FIG. 24C

SQ Sequence 5052 BP: 1201 A; 1249 C; 1201 G; 1399 T.

```
GGATCCTGTT GACTCGTGAC CTTACCCCCA ACCCTGTGCT CTCTGAAACA TGAGCTGTGT
CCACTCAGGG TTAAATGGAT TAAGGGCGGT GCAAGATGTG CTTTGTTAAA CAGATGCTTG
AAGGCAGCAT GCTCGTTAAG AGTCATCACC AATCCCTAAT CTCAAGTAAT CAGGGACACA
AACACTGCGG AAGGCCGCAG GGTCCTCTGC CTAGGAAAAC CAGAGACCTT TGTTCACTTG
TTTATCTGAC CTTCCCTCCA CTATTGTCCA TGACCCTGCC AAATCCCCCT CTGTGAGAAA
CACCCAAGAA TTATCAATAA AAAATAAAT TTAAAAAAAA AATACAAAAA AAAAAAAAAA
AAAAAAAAAA GACTTACGAA TAGTTATTGA TAAATGAATA GCTATTGGTA AAGCCAAGTA
AATGATCATA TTCAAAACCA GACGGCCATC ATCACAGCTC AAGTCTACCT GATTTGATCT
CTTTATCATT GTCATTCTTT GGATTCACTA GATTAGTCAT CATCCTCAAA ATTCTCCCCC
AAGTTCTAAT TACGTTCCAA ACATTAGGG GTTACATGAA GCTTGAACCT ACTACCTTCT
TTGCTTTTGA GCCATGAGTT GTAGGAATGA TGAGTTTACA CCTTACATGC TGGGGATTAA
TTTAAACTTT ACCTCTAAGT CAGTTGGGTA GCCTTTGGCT TATTTTTGTA GCTAATTTTG
TAGTTAATGG ATGCACTGTG AATCTTGCTA TGATAGTTTT CCTCCACACT TTGCCACTAG
GGGTAGGTAG GTACTCAGTT TTCAGTAATT GCTTACCTAA GACCCTAAGC CCTATTTCTC
TTGTACTGGC CTTTATCTGT AATATGGCA TATTTAATAC AATATAATTT TTGGAGTTTT
TTTGTTTGTT TGTTTGTTTG TTTTTTTGAG ACGGAGTCTT GCATCTGTCA TGCCCAGGCT
GGAGTAGCAG TGGTGCCATC TCGGCTCACT GCAAGCTCCA CCTCCCGAGT TCACGCCATT
TTCCTGCCTC AGCCTCCCGA GTAGCTGGGA CTACAGGCGC CCGCCACCAT GCCCGGCTAA
TTTTTTGTAT TTTTGGTAGA GACGGGGTTT CACCGTGTTA GCCAGAATGG TCTCGATCTC
CTGACTTCGT GATCCACCCG CCTCGGCCTC CCAAAGTTCT GGGATTACAG GTGTGAGCCA
CCGCACCTGG CCAATTTTTT GAGTCTTTTA AAGTAAAAAT ATGTCTTGTA AGCTGGTAAC
TATGGTACAT TTCCTTTTAT TAATGTGGTG CTGACGGTCA TATAGGTTCT TTTGAGTTTG
GCATGCATAT GCTACTTTTT GCAGTCCTTT CATTACATTT TTCTCTCTTC ATTTGAAGAG
CATGTTATAT CTTTTAGCTT CACTTGGCTT AAAAGGTTCT CTCATTAGCC TAACACAGTG
TCATTGTTGG TACCACTTGG ATCATAAGTG GAAAAACAGT CAAGAAATTG CACAGTAATA
CTTGTTTGTA AGAGGGATGA TTCAGGTGAA TCTGACACTA AGAAACTCCC CTACCTGAGG
TCTGAGATTC CTCTGACATT GCTGTATATA GGCTTTTCCT TTGACAGCCT GTGACTGCGG
ACTATTTTTC TTAAGCAAGA TATGCTAAAG TTTTGTGAGC CTTTTTCCAG AGAGAGGTCT
CATATCTGCA TCAAGTGAGA ACATATAATG TCTGCATGTT TCCATATTTC AGGAATGTTT
GCTTGTGTTT TATGCTTTTA TATAGACAGG GAAACTTGTT CCTCAGTGAC CCAAAAGAGG
TGGGAATTGT TATTGGATAT CATCATTGGC CCACGCTTTC TGACCTTGGA AACAATTAAG
GGTTCATAAT CTCAATTCTG TCAGAATTGG TACAAGAAAT AGCTGCTATG TTTCTTGACA
TTCCACTTGG TAGGAAATAA GAATGTGAAA CTCTTCAGTT GGTGTGTGTC CCTNGTTTTT
TTGCAATTTC CTTCTTACTG TGTTAAAAAA AAGTATGATC TTGCTCTGAG AGGTGAGGCA
TTCTTAATCA TGATCTTTAA AGATCAATAA TATAATCCTT TCAAGGATTA TGTCTTTATT
ATAATAAAGA TAATTTGTCT TTAACAGAAT CAATAATATA ATCCCTTAAA GGATTATATC
TTTGCTGGGC GCAGTGGCTC ACACCTGTAA TCCCAGCACT TGGGTGGCC AAGGTGGAAG
GATCAAATTT GCCTACTTCT ATATTATCTT CTAAAGCAGA ATTCATCTCT CTTCCCTCAA
TATGATGATA TTGACAGGGT TTGCCCTCAC TCACTAGATT GTGAGCTCCT GCTCAGGGCA
GGTAGNGTTT TTTGTTTTTG TTTTTGTTTT TCTTTTTTGA GACAGGGTCT TGCTCTGTCA
CCCAGGCCAG AGTGCAATGG TACAGTCTCA GCTCACTGCA GCCTCAACGC CTCGGCTCAA
ACCATCATCC CATTTCAGCC TCCTGAGTAG CTGGGACTAC AGGCACATGC CATTACACCT
```

FIG. 25A

```
GGCTAATTTT TTTGTATTTC TAGTAGAGAC AGGGTTTGGC CATGTTGCCC GGGCTGGTCT
CGAACTCCTG GACTCAAGCA ATCCACCCAC CTCAGCCTCC CAAAATGAGG GACCGTGTCT
TATTCATTTC CATGTCCCTA GTCCATAGCC CAGTGCTGGA CCTATGGTAG TACTAAATAA
ATATTTGTTG AATGCAATAG TAAATAGCAT TTCAGGGAGC AAGAACTAGA TTAACAAAGG
TGGTAAAAGG TTTGGAGAAA AAAATAATAG TTTAATTTGG CTAGAGTATG AGGGAGAGTA
GTAGGAGACA AGATGGAAAG GTCTCTTGGG CAAGGTTTTG AAGGAAGTTG GAAGTCAGAA
GTACACAATG TGATATCGTG GCAGGCAGTG GGGAGCCAAT GAAGGCTTTT GAGCAGGAGA
GTAATGTGTT GAAAATAAA TATAGGTTAA ACCTATCAGA GCCCCTCTGA CACATACACT
TGCTTTTCAT TCAAGCTCAA GTTTGTCTCC CACATACCCA TTACTTAACT CACCCTCGGG
CTCCCCTAGC AGCCTGCCCT ACCTCTTTAC CTGCTTCCTG GTGGAGTCAG GGATGTATAC
ATGAGCTGCT TTCCCTCTCA GCCAGAGACA TGGGGGGCCC CAGCTCCCCT GCCTTTCCCC
TTCTGTGCCT GGAGCTGGGA AGCAGGCCAG GGTTAGCTGA GGCTGGCTGG CAAGCAGCTG
GGTGGTGCCA GGGAGAGCCT GCATAGTGCC AGGTGGTGCC TTGGGTTCCA AGCTAGTCCA
TGGCCCCGAT AACCTTCTGC CTGTGCACAC ACCTGCCCCT CACTCCACCC CCATCCTAGC
TTTGGTATGG GGGAGAGGGC ACAGGGCCAG ACAAACCTGT GAGACTTTGG CTCCATCTCT
GCAAAGGGC GCTCTGTGAG TCAGCCTGCT CCCCTCCAGG CTTGCTCCTC CCCCACCCAG
CTCTCGTTTC CAATGCACGT ACAGCCCGTA CACACCGTGT GCTGGGACAC CCCACAGTCA
GCGCATGGCT CCCCTGTGCC CCAGCCCCTG GCTCCCTCTG TTGATCCCGG CCCCTGCTCC
AGGCCTCACT GTGCAACTGC TGCTGTCACT GCTGCTTCTG ATGCCTGTCC ATCCCCAGAG
GTTGCCCCGG ATGCAGGAGG ATTCCCCCTT GGAGGAGGCT CTTCTGGGGA AGATGACCCA
CTGGGCGAGG AGGATCTGCC CAGTGAAGAG GATTCACCCA GAGAGGAGGA TCCACCCGGA
GAGGAGGATC TACCTGGAGA GGAGGATCTA CCTGGAGAGG AGGATCTACC TGAAGTTAAT
GCCTAAATCA GAAGAAGAGG GCTCCCTGAA GTTAGAGGAT CTACCTACTG TTGAGGCTCC
TGGAGATCCT CAAGAACCCC AGAATAATGC CCACAGGGAC AAAGAAGGGG ATGACCAGAG
TCATTGGCGC TATGGAGGCG ACCCGCCTGG CCCCGGGTGT CCCCAGCCTG CGCGGGCCGC
TTCCAGTCCC CGGTGGATAT CCGCCCCAG CTCGCCGCCT TCTGCCCGGC CCTGCGCCCC
CTGGAACTCC TGGGCTTCCA GCTCCCGCCG CTCCCAGAAC TGCGCCTGCA GACAATGGCC
ACAGTGTGCA ACTGACCCTG CCTCCTGGGC TAGAGATGGC TCTGGGTCCC GGGCGGGAGT
ACCGGCTCTG CAGCTGCATC TGCACTGGGG GGCTGCAGGT CGTCCGGGCT CGGAGCACAC
TGTGGAAGGC CACCGTTTCC CTGCCGAGAT CCACGTGGTT CACCTCAGCA CCGCCTTTGC
CAGAGTTGAC GAGGCCTTGG GGCGCCCGGG AGGCCTGGCC GTGTTGGCGC CTTTCTGGAG
GAGGGCCCGG AAGAAAACAG TGTCCTATGA GCAGTTGCTG TCTCGCTTGG AAGAAATCGC
TGAGGAAGGC TCAGAGACTC AGGTCCCAGG ACTGGACATA TCTGCACTCC TGCCCTCTGA
CTTCAGCCGC TACTTCAAT ATGAGGGGTC TCTGACTACA CCGCCCTGTG CCCAGGGTGT
CATCTGGACT GTGTTTAACC AGACAGTGAT GCTGAGTGCT AAGCAGCTCC ACACCCTCTC
TGACACCCTG TGGGGACCTG GTGACTCTCG GCTACAGCTG AACTTCCGAG CGACGCAGCC
TTTGAATGGG CGAGTGATTG AGGCCTCCTT CCCTGCTGGA GTGGACAGCA GTCCTCGGGC
TGCTGAGCCA GTCCAGCTGA ATTCTGCCT GGCTGCTGGT GACATCCTAG CCCTGGTTTT
TGGCCTCCTT TTTGCTGTCA CCAGCGTCGC GTTCCTTGTG CAGATGAGAA GGCAGCACAG
AAGGGGAACC AAAGGGGGTG TGAGCGTACC GCCCAGCAGA GGTAGCCGAG ACTGGAGCCT
AGAGGCTGGA TCTTGGAGAA TGTGAGAAGC CAGCCAGAGG CATCTGAGGG GGAGCCGGTA
ACTGTCCTGT CCTGCTCATT ATGCCACTTC CTTTTAACTG CCAAGAAATT TTTTAAAATA
AATATTTATA AT
//
```

FIG. 25B

SEQUENCE LISTING

```
<160> NUMBER OF SEQ ID NOS: 26

<210> SEQ ID NO 1
<211> LENGTH: 1399
<212> TYPE: DNA
<213> ORGANISM: HUMAN
<220> FEATURE:
<221> NAME/KEY: CDS
<222> LOCATION: (1)..(1266)

<400> SEQUENCE: 1 cag agg ttg ccc cgg atg cag gag gat tcc ccc ttg gga gga ggc tct       48
Gln Arg Leu Pro Arg Met Gln Glu Asp Ser Pro Leu Gly Gly Gly Ser
 1               5                  10                  15 tct ggg gaa gat gac cca ctg ggc gag gag gat ctg ccc agt gaa gag       96
Ser Gly Glu Asp Asp Pro Leu Gly Glu Glu Asp Leu Pro Ser Glu Glu
             20                  25                  30 gat tca ccc aga gag gag gat cca ccc gga gag gag gat cta cct gga      144
Asp Ser Pro Arg Glu Glu Asp Pro Pro Gly Glu Glu Asp Leu Pro Gly
         35                  40                  45 gag gag gat cta cct gga gag gag gat cta cct gaa gtt aag cct aaa      192
Glu Glu Asp Leu Pro Gly Glu Glu Asp Leu Pro Glu Val Lys Pro Lys
     50                  55                  60 tca gaa gaa gag ggc tcc ctg aag tta gag gat cta cct act gtt gag      240
Ser Glu Glu Glu Gly Ser Leu Lys Leu Glu Asp Leu Pro Thr Val Glu
 65                  70                  75                  80 gct cct gga gat cct caa gaa ccc cag aat aat gcc cac agg gac aaa      288
Ala Pro Gly Asp Pro Gln Glu Pro Gln Asn Asn Ala His Arg Asp Lys
                 85                  90                  95 gaa ggg gat gac cag agt cat tgg cgc tat gga ggc gac ccg ccc tgg      336
Glu Gly Asp Asp Gln Ser His Trp Arg Tyr Gly Gly Asp Pro Pro Trp
            100                 105                 110 ccc cgg gtg tcc cca gcc tgc gcg ggc cgc ttc cag tcc ccg gtg gat      384
Pro Arg Val Ser Pro Ala Cys Ala Gly Arg Phe Gln Ser Pro Val Asp
        115                 120                 125 atc cgc ccc cag ctc gcc gcc ttc tgc ccg gcc ctg cgc ccc ctg gaa      432
Ile Arg Pro Gln Leu Ala Ala Phe Cys Pro Ala Leu Arg Pro Leu Glu
    130                 135                 140 ctc ctg ggc ttc cag ctc ccg ccg ctc cca gaa ctg cgc ctg cgc aac      480
Leu Leu Gly Phe Gln Leu Pro Pro Leu Pro Glu Leu Arg Leu Arg Asn
145                 150                 155                 160 aat ggc cac agt gtg caa ctg acc ctg cct ggg cta gag atg gct           528
Asn Gly His Ser Val Gln Leu Thr Leu Pro Pro Gly Leu Glu Met Ala
                165                 170                 175 ctg ggt ccc ggg cgg gag tac cgg gct ctg cag ctg cat ctg cac tgg      576
Leu Gly Pro Gly Arg Glu Tyr Arg Ala Leu Gln Leu His Leu His Trp
            180                 185                 190 ggg gct gca ggt cgt ccg ggc tcg gag cac act gtg gaa ggc cac cgt      624
Gly Ala Ala Gly Arg Pro Gly Ser Glu His Thr Val Glu Gly His Arg
        195                 200                 205 ttc cct gcc gag atc cac gtg gtt cac ctc agc acc gcc ttt gcc aga      672
```

-continued

```
                Phe Pro Ala Glu Ile His Val Val His Leu Ser Thr Ala Phe Ala Arg
                    210                 215                 220 gtt gac gag gcc ttg ggg cgc ccg gga ggc ctg gcc gtg ttg gcc gcc                720
Val Asp Glu Ala Leu Gly Arg Pro Gly Gly Leu Ala Val Leu Ala Ala
225                 230                 235                 240 ttt ctg gag gag ggc ccg gaa gaa aac agt gcc tat gag cag ttg ctg                768
Phe Leu Glu Glu Gly Pro Glu Glu Asn Ser Ala Tyr Glu Gln Leu Leu
                245                 250                 255 tct cgc ttg gaa gaa atc gct gag gaa ggc tca gag act cag gtc cca                816
Ser Arg Leu Glu Glu Ile Ala Glu Glu Gly Ser Glu Thr Gln Val Pro
            260                 265                 270 gga ctg gac ata tct gca ctc ctg ccc tct gac ttc agc cgc tac ttc                864
Gly Leu Asp Ile Ser Ala Leu Leu Pro Ser Asp Phe Ser Arg Tyr Phe
        275                 280                 285 caa tat gag ggg tct ctg act aca ccg ccc tgt gcc cag ggt gtc atc                912
Gln Tyr Glu Gly Ser Leu Thr Thr Pro Pro Cys Ala Gln Gly Val Ile
    290                 295                 300 tgg act gtg ttt aac cag aca gtg atg ctg agt gct aag cag ctc cac                960
Trp Thr Val Phe Asn Gln Thr Val Met Leu Ser Ala Lys Gln Leu His
305                 310                 315                 320 acc ctc tct gac acc ctg tgg gga cct ggt gac tct cgg cta cag ctg               1008
Thr Leu Ser Asp Thr Leu Trp Gly Pro Gly Asp Ser Arg Leu Gln Leu
                325                 330                 335 aac ttc cga gcg acg cag cct ttg aat ggg cga gtg att gag gcc tcc               1056
Asn Phe Arg Ala Thr Gln Pro Leu Asn Gly Arg Val Ile Glu Ala Ser
            340                 345                 350 ttc cct gct gga gtg gac agc agt cct cgg gct gct gag cca gtc cag               1104
Phe Pro Ala Gly Val Asp Ser Ser Pro Arg Ala Ala Glu Pro Val Gln
        355                 360                 365 ctg aat tcc tgc ctg gct gct ggt gac atc cta gcc ctg gtt ttt ggc               1152
Leu Asn Ser Cys Leu Ala Ala Gly Asp Ile Leu Ala Leu Val Phe Gly
    370                 375                 380 ctc ctt ttt gct gtc acc agc gtc gcg ttc ctt gtg cag atg aga agg               1200
Leu Leu Phe Ala Val Thr Ser Val Ala Phe Leu Val Gln Met Arg Arg
385                 390                 395                 400 cag cac aga agg gga acc aaa ggg ggt gtg agc tac cgc cca gca gag               1248
Gln His Arg Arg Gly Thr Lys Gly Gly Val Ser Tyr Arg Pro Ala Glu
                405                 410                 415 gta gcc gag act gga gcc tagaggctgg atcttggaga atgtgagaag                      1296
Val Ala Glu Thr Gly Ala
                420 ccagccagag gcatctgagg gggagccggt aactgtcctg tcctgctcat tatgccactt             1356 ccttttaact gccaagaaat tttttaaaat aaatatttat aat                               1399

<210> SEQ ID NO 2
<211> LENGTH: 422
<212> TYPE: PRT
<213> ORGANISM: HUMAN

<400> SEQUENCE: 2

Gln Arg Leu Pro Arg Met Gln Glu Asp Ser Pro Leu Gly Gly Gly Ser
1               5                   10                  15

Ser Gly Glu Asp Asp Pro Leu Gly Glu Glu Asp Leu Pro Ser Glu Glu
                20                  25                  30

Asp Ser Pro Arg Glu Glu Asp Pro Pro Gly Glu Glu Asp Leu Pro Gly
            35                  40                  45

Glu Glu Asp Leu Pro Gly Glu Glu Asp Leu Pro Glu Val Lys Pro Lys
        50                  55                  60
```

```
Ser Glu Glu Glu Gly Ser Leu Lys Leu Glu Asp Leu Pro Thr Val Glu
 65                  70                  75                  80

Ala Pro Gly Asp Pro Gln Glu Pro Gln Asn Asn Ala His Arg Asp Lys
                 85                  90                  95

Glu Gly Asp Asp Gln Ser His Trp Arg Tyr Gly Gly Asp Pro Pro Trp
             100                 105                 110

Pro Arg Val Ser Pro Ala Cys Ala Gly Arg Phe Gln Ser Pro Val Asp
         115                 120                 125

Ile Arg Pro Gln Leu Ala Ala Phe Cys Pro Ala Leu Arg Pro Leu Glu
     130                 135                 140

Leu Leu Gly Phe Gln Leu Pro Pro Leu Pro Glu Leu Arg Leu Arg Asn
145                 150                 155                 160

Asn Gly His Ser Val Gln Leu Thr Leu Pro Pro Gly Leu Glu Met Ala
                165                 170                 175

Leu Gly Pro Gly Arg Glu Tyr Arg Ala Leu Gln Leu His Leu His Trp
            180                 185                 190

Gly Ala Ala Gly Arg Pro Gly Ser Glu His Thr Val Glu Gly His Arg
        195                 200                 205

Phe Pro Ala Glu Ile His Val Val His Leu Ser Thr Ala Phe Ala Arg
    210                 215                 220

Val Asp Glu Ala Leu Gly Arg Pro Gly Gly Leu Ala Val Leu Ala Ala
225                 230                 235                 240

Phe Leu Glu Glu Gly Pro Glu Glu Asn Ser Ala Tyr Glu Gln Leu Leu
                245                 250                 255

Ser Arg Leu Glu Glu Ile Ala Glu Glu Gly Ser Glu Thr Gln Val Pro
            260                 265                 270

Gly Leu Asp Ile Ser Ala Leu Leu Pro Ser Asp Phe Ser Arg Tyr Phe
        275                 280                 285

Gln Tyr Glu Gly Ser Leu Thr Thr Pro Pro Cys Ala Gln Gly Val Ile
    290                 295                 300

Trp Thr Val Phe Asn Gln Thr Val Met Leu Ser Ala Lys Gln Leu His
305                 310                 315                 320

Thr Leu Ser Asp Thr Leu Trp Gly Pro Gly Asp Ser Arg Leu Gln Leu
                325                 330                 335

Asn Phe Arg Ala Thr Gln Pro Leu Asn Gly Arg Val Ile Glu Ala Ser
            340                 345                 350

Phe Pro Ala Gly Val Asp Ser Ser Pro Arg Ala Ala Glu Pro Val Gln
        355                 360                 365

Leu Asn Ser Cys Leu Ala Ala Gly Asp Ile Leu Ala Leu Val Phe Gly
    370                 375                 380

Leu Leu Phe Ala Val Thr Ser Val Ala Phe Leu Val Gln Met Arg Arg
385                 390                 395                 400

Gln His Arg Arg Gly Thr Lys Gly Gly Val Ser Tyr Arg Pro Ala Glu
                405                 410                 415

Val Ala Glu Thr Gly Ala
            420

<210> SEQ ID NO 3
<211> LENGTH: 29
<212> TYPE: DNA
<213> ORGANISM: HUMAN

<400> SEQUENCE: 3
cgcccagtgg gtcatcttcc ccagaagag                               29
```

```
<210> SEQ ID NO 4
<211> LENGTH: 19
<212> TYPE: DNA
<213> ORGANISM: HUMAN

<400> SEQUENCE: 4
ggaatcctcc tgcatccgg                                                  19

<210> SEQ ID NO 5
<211> LENGTH: 1522
<212> TYPE: DNA
<213> ORGANISM: HUMAN
<220> FEATURE:
<221> NAME/KEY: CDS
<222> LOCATION: (13)..(1389)
<220> FEATURE:
<221> NAME/KEY: mat_peptide
<222> LOCATION: (124)..(1389)

<400> SEQUENCE: 5
acagtcagcc gc atg gct ccc ctg tgc ccc agc ccc tgg ctc cct ctg ttg         51
          Met Ala Pro Leu Cys Pro Ser Pro Trp Leu Pro Leu Leu
               -35              -30              -25 atc ccg gcc cct gct cca ggc ctc act gtg caa ctg ctg ctg tca ctg           99
Ile Pro Ala Pro Ala Pro Gly Leu Thr Val Gln Leu Leu Leu Ser Leu
         -20              -15              -10 ctg ctt ctg atg cct gtc cat ccc cag agg ttg ccc cgg atg cag gag          147
Leu Leu Leu Met Pro Val His Pro Gln Arg Leu Pro Arg Met Gln Glu
             -5              -1  1               5 gat tcc ccc ttg gga gga ggc tct tct ggg gaa gat gac cca ctg ggc          195
Asp Ser Pro Leu Gly Gly Gly Ser Ser Gly Glu Asp Asp Pro Leu Gly
     10                  15                  20 gag gag gat ctg ccc agt gaa gag gat tca ccc aga gag gag gat cca          243
Glu Glu Asp Leu Pro Ser Glu Glu Asp Ser Pro Arg Glu Glu Asp Pro
 25                  30                  35                  40 ccc gga gag gag gat cta cct gga gag gag gat cta cct gga gag gag          291
Pro Gly Glu Glu Asp Leu Pro Gly Glu Glu Asp Leu Pro Gly Glu Glu
                 45                  50                  55 gat cta cct gaa gtt aag cct aaa tca gaa gaa gag ggc tcc ctg aag          339
Asp Leu Pro Glu Val Lys Pro Lys Ser Glu Glu Glu Gly Ser Leu Lys
             60                  65                  70 tta gag gat cta cct act gtt gag gct cct gga gat cct caa gaa ccc          387
Leu Glu Asp Leu Pro Thr Val Glu Ala Pro Gly Asp Pro Gln Glu Pro
         75                  80                  85 cag aat aat gcc cac agg gac aaa gaa ggg gat gac cag agt cat tgg          435
Gln Asn Asn Ala His Arg Asp Lys Glu Gly Asp Asp Gln Ser His Trp
     90                  95                 100 cgc tat gga ggc gac ccg ccc tgg ccc cgg gtg tcc cca gcc tgc gcg          483
Arg Tyr Gly Gly Asp Pro Pro Trp Pro Arg Val Ser Pro Ala Cys Ala
105                 110                 115                 120 ggc cgc ttc cag tcc ccg gtg gat atc cgc ccc cag ctc gcc gcc ttc          531
Gly Arg Phe Gln Ser Pro Val Asp Ile Arg Pro Gln Leu Ala Ala Phe
                125                 130                 135 tgc ccg gcc ctg cgc ccc ctg gaa ctc ctg ggc ttc cag ctc ccg ccg          579
Cys Pro Ala Leu Arg Pro Leu Glu Leu Leu Gly Phe Gln Leu Pro Pro
            140                 145                 150 ctc cca gaa ctg cgc ctg cgc aac aat ggc cac agt gtg caa ctg acc          627
Leu Pro Glu Leu Arg Leu Arg Asn Asn Gly His Ser Val Gln Leu Thr
        155                 160                 165 ctg cct cct ggg cta gag atg gct ctg ggt ccc ggg cgg gag tac cgg          675
Leu Pro Pro Gly Leu Glu Met Ala Leu Gly Pro Gly Arg Glu Tyr Arg
    170                 175                 180
```

```
gct ctg cag ctg cat ctg cac tgg ggg gct gca ggt cgt ccg ggc tcg    723
Ala Leu Gln Leu His Leu His Trp Gly Ala Ala Gly Arg Pro Gly Ser
185                 190                 195                 200 gag cac act gtg gaa ggc cac cgt ttc cct gcc gag atc cac gtg gtt    771
Glu His Thr Val Glu Gly His Arg Phe Pro Ala Glu Ile His Val Val
                205                 210                 215 cac ctc agc acc gcc ttt gcc aga gtt gac gag gcc ttg ggg cgc ccg    819
His Leu Ser Thr Ala Phe Ala Arg Val Asp Glu Ala Leu Gly Arg Pro
                220                 225                 230 gga ggc ctg gcc gtg ttg gcc gcc ttt ctg gag gag ggc ccg gaa gaa    867
Gly Gly Leu Ala Val Leu Ala Ala Phe Leu Glu Glu Gly Pro Glu Glu
                235                 240                 245 aac agt gcc tat gag cag ttg ctg tct cgc ttg gaa gaa atc gct gag    915
Asn Ser Ala Tyr Glu Gln Leu Leu Ser Arg Leu Glu Glu Ile Ala Glu
            250                 255                 260 gaa ggc tca gag act cag gtc cca gga ctg gac ata tct gca ctc ctg    963
Glu Gly Ser Glu Thr Gln Val Pro Gly Leu Asp Ile Ser Ala Leu Leu
265                 270                 275                 280 ccc tct gac ttc agc cgc tac ttc caa tat gag ggg tct ctg act aca   1011
Pro Ser Asp Phe Ser Arg Tyr Phe Gln Tyr Glu Gly Ser Leu Thr Thr
                285                 290                 295 ccg ccc tgt gcc cag ggt gtc atc tgg act gtg ttt aac cag aca gtg   1059
Pro Pro Cys Ala Gln Gly Val Ile Trp Thr Val Phe Asn Gln Thr Val
                300                 305                 310 atg ctg agt gct aag cag ctc cac acc ctc tct gac acc ctg tgg gga   1107
Met Leu Ser Ala Lys Gln Leu His Thr Leu Ser Asp Thr Leu Trp Gly
                315                 320                 325 cct ggt gac tct cgg cta cag ctg aac ttc cga gcg acg cag cct ttg   1155
Pro Gly Asp Ser Arg Leu Gln Leu Asn Phe Arg Ala Thr Gln Pro Leu
                330                 335                 340 aat ggg cga gtg att gag gcc tcc ttc cct gct gga gtg gac agc agt   1203
Asn Gly Arg Val Ile Glu Ala Ser Phe Pro Ala Gly Val Asp Ser Ser
345                 350                 355                 360 cct cgg gct gct gag cca gtc cag ctg aat tcc tgc ctg gct gct ggt   1251
Pro Arg Ala Ala Glu Pro Val Gln Leu Asn Ser Cys Leu Ala Ala Gly
                365                 370                 375 gac atc cta gcc ctg gtt ttt ggc ctc ctt ttt gct gtc acc agc gtc   1299
Asp Ile Leu Ala Leu Val Phe Gly Leu Leu Phe Ala Val Thr Ser Val
                380                 385                 390 gcg ttc ctt gtg cag atg aga agg cag cac aga agg gga acc aaa ggg   1347
Ala Phe Leu Val Gln Met Arg Arg Gln His Arg Arg Gly Thr Lys Gly
                395                 400                 405 ggt gtg agc tac cgc cca gca gag gta gcc gag act gga gcc              1389
Gly Val Ser Tyr Arg Pro Ala Glu Val Ala Glu Thr Gly Ala
            410                 415                 420 tagaggctgg atcttggaga atgtgagaag ccagccagag gcatctgagg gggagccggt    1449
aactgtcctg tcctgctcat tatgccactt ccttttaact gccaagaaat ttttaaaat     1509 aaatatttat aat                                                      1522

<210> SEQ ID NO 6
<211> LENGTH: 459
<212> TYPE: PRT
<213> ORGANISM: HUMAN

<400> SEQUENCE: 6

Met Ala Pro Leu Cys Pro Ser Pro Trp Leu Pro Leu Leu Ile Pro Ala
            -35                 -30                 -25

Pro Ala Pro Gly Leu Thr Val Gln Leu Leu Leu Ser Leu Leu Leu Leu
```

```
            -20                -15                -10
Met Pro Val His Pro Gln Arg Leu Pro Arg Met Gln Glu Asp Ser Pro
 -5              -1   1                 5                      10

Leu Gly Gly Gly Ser Ser Gly Glu Asp Asp Pro Leu Gly Glu Glu Asp
             15                  20                  25

Leu Pro Ser Glu Glu Asp Ser Pro Arg Glu Glu Asp Pro Pro Gly Glu
         30                  35                  40

Glu Asp Leu Pro Gly Glu Glu Asp Leu Pro Gly Glu Glu Asp Leu Pro
         45                  50                  55

Glu Val Lys Pro Lys Ser Glu Glu Gly Ser Leu Lys Leu Glu Asp
     60              65                  70                  75

Leu Pro Thr Val Glu Ala Pro Gly Asp Pro Gln Glu Pro Gln Asn Asn
                 80                  85                  90

Ala His Arg Asp Lys Glu Gly Asp Asp Gln Ser His Trp Arg Tyr Gly
             95                 100                 105

Gly Asp Pro Pro Trp Pro Arg Val Ser Pro Ala Cys Ala Gly Arg Phe
            110                 115                 120

Gln Ser Pro Val Asp Ile Arg Pro Gln Leu Ala Ala Phe Cys Pro Ala
        125                 130                 135

Leu Arg Pro Leu Glu Leu Leu Gly Phe Gln Leu Pro Pro Leu Pro Glu
140                 145                 150                 155

Leu Arg Leu Arg Asn Asn Gly His Ser Val Gln Leu Thr Leu Pro Pro
                160                 165                 170

Gly Leu Glu Met Ala Leu Gly Pro Gly Arg Glu Tyr Arg Ala Leu Gln
            175                 180                 185

Leu His Leu His Trp Gly Ala Ala Gly Arg Pro Gly Ser Glu His Thr
        190                 195                 200

Val Glu Gly His Arg Phe Pro Ala Glu Ile His Val Val His Leu Ser
        205                 210                 215

Thr Ala Phe Ala Arg Val Asp Glu Ala Leu Gly Arg Pro Gly Gly Leu
220                 225                 230                 235

Ala Val Leu Ala Ala Phe Leu Glu Glu Gly Pro Glu Glu Asn Ser Ala
                240                 245                 250

Tyr Glu Gln Leu Leu Ser Arg Leu Glu Glu Ile Ala Glu Glu Gly Ser
            255                 260                 265

Glu Thr Gln Val Pro Gly Leu Asp Ile Ser Ala Leu Leu Pro Ser Asp
        270                 275                 280

Phe Ser Arg Tyr Phe Gln Tyr Glu Gly Ser Leu Thr Thr Pro Pro Cys
        285                 290                 295

Ala Gln Gly Val Ile Trp Thr Val Phe Asn Gln Thr Val Met Leu Ser
300                 305                 310                 315

Ala Lys Gln Leu His Thr Leu Ser Asp Thr Leu Trp Gly Pro Gly Asp
                320                 325                 330

Ser Arg Leu Gln Leu Asn Phe Arg Ala Thr Gln Pro Leu Asn Gly Arg
            335                 340                 345

Val Ile Glu Ala Ser Phe Pro Ala Gly Val Asp Ser Ser Pro Arg Ala
        350                 355                 360

Ala Glu Pro Val Gln Leu Asn Ser Cys Leu Ala Ala Gly Asp Ile Leu
        365                 370                 375

Ala Leu Val Phe Gly Leu Leu Phe Ala Val Thr Ser Val Ala Phe Leu
380                 385                 390                 395

Val Gln Met Arg Arg Gln His Arg Arg Gly Thr Lys Gly Gly Val Ser
                400                 405                 410
```

Tyr Arg Pro Ala Glu Val Ala Glu Thr Gly Ala
            415                 420

<210> SEQ ID NO 7
<211> LENGTH: 25
<212> TYPE: DNA
<213> ORGANISM: HUMAN

<400> SEQUENCE: 7
tggggttctt gaggatctcc aggag                                           25

<210> SEQ ID NO 8
<211> LENGTH: 26
<212> TYPE: DNA
<213> ORGANISM: HUMAN

<400> SEQUENCE: 8
ctctaacttc agggagccct cttctt                                          26

<210> SEQ ID NO 9
<211> LENGTH: 48
<212> TYPE: DNA
<213> ORGANISM: HUMAN
<220> FEATURE:
<221> NAME/KEY: primer_bind
<222> LOCATION: (1)..(48)

<400> SEQUENCE: 9
cuacuacuac uaggccacgc gtcgactagt acgggnnggg nngggnng                  48

<210> SEQ ID NO 10
<211> LENGTH: 6
<212> TYPE: PRT
<213> ORGANISM: HUMAN

<400> SEQUENCE: 10

Glu Glu Asp Leu Pro Ser
  1               5

<210> SEQ ID NO 11
<211> LENGTH: 6
<212> TYPE: PRT
<213> ORGANISM: HUMAN

<400> SEQUENCE: 11

Gly Glu Asp Asp Pro Leu
  1               5

<210> SEQ ID NO 12
<211> LENGTH: 21
<212> TYPE: PRT
<213> ORGANISM: HUMAN

<400> SEQUENCE: 12

Asn Asn Ala His Arg Asp Lys Glu Gly Asp Asp Gln Ser His Trp Arg
  1               5                  10                  15

Tyr Gly Gly Asp Pro
             20

<210> SEQ ID NO 13
<211> LENGTH: 16
<212> TYPE: PRT
<213> ORGANISM: HUMAN

<400> SEQUENCE: 13

His Pro Gln Arg Leu Pro Arg Met Gln Glu Asp Ser Pro Leu Gly Gly
1               5                   10                  15

<210> SEQ ID NO 14
<211> LENGTH: 24
<212> TYPE: PRT
<213> ORGANISM: HUMAN

<400> SEQUENCE: 14

Glu Glu Asp Ser Pro Arg Glu Glu Asp Pro Pro Gly Glu Glu Asp Leu
1               5                   10                  15

Pro Gly Glu Glu Asp Leu Pro Gly
            20

<210> SEQ ID NO 15
<211> LENGTH: 13
<212> TYPE: PRT
<213> ORGANISM: HUMAN

<400> SEQUENCE: 15

Leu Glu Glu Gly Pro Glu Glu Asn Ser Ala Tyr Glu Gln
1               5                   10

<210> SEQ ID NO 16
<211> LENGTH: 16
<212> TYPE: PRT
<213> ORGANISM: HUMAN

<400> SEQUENCE: 16

Met Arg Arg Gln His Arg Arg Gly Thr Lys Gly Gly Val Ser Tyr Arg
1               5                   10                  15

<210> SEQ ID NO 17
<211> LENGTH: 45
<212> TYPE: DNA
<213> ORGANISM: HUMAN

<400> SEQUENCE: 17
gtcgctagct ccatgggtca tatgcagagg ttgccccgga tgcag            45

<210> SEQ ID NO 18
<211> LENGTH: 43
<212> TYPE: DNA
<213> ORGANISM: HUMAN

<400> SEQUENCE: 18
gaagatctct tactcgagca ttctccaaga tccagcctct agg              43

<210> SEQ ID NO 19
<211> LENGTH: 10
<212> TYPE: DNA
<213> ORGANISM: HUMAN
<220> FEATURE:
<221> NAME/KEY: misc_feature
<222> LOCATION: (1)..(10)

<400> SEQUENCE: 19 yssccmnsss                                                   10

<210> SEQ ID NO 20
<211> LENGTH: 10
<212> TYPE: DNA
<213> ORGANISM: HUMAN

```
<220> FEATURE:
<221> NAME/KEY: misc_feature
<222> LOCATION: (1)..(10)

<400> SEQUENCE: 20 kmggcckrry                                                                      10

<210> SEQ ID NO 21
<211> LENGTH: 10
<212> TYPE: DNA
<213> ORGANISM: HUMAN
<220> FEATURE:
<221> NAME/KEY: misc_feature
<222> LOCATION: (1)..(10)

<400> SEQUENCE: 21 rrrcwwgyyy                                                                      10

<210> SEQ ID NO 22
<211> LENGTH: 8
<212> TYPE: PRT
<213> ORGANISM: HUMAN

<400> SEQUENCE: 22

Leu Glu His His His His His His
 1               5

<210> SEQ ID NO 23
<211> LENGTH: 5052
<212> TYPE: DNA
<213> ORGANISM: HUMAN
<220> FEATURE:
<221> NAME/KEY: misc_feature
<222> LOCATION: (1)..(5052)

<400> SEQUENCE: 23
ggatcctgtt gactcgtgac cttaccccca accctgtgct ctctgaaaca tgagctgtgt       60
ccactcaggg ttaaatggat taagggcggt gcaagatgtg ctttgttaaa cagatgcttg      120
aaggcagcat gctcgttaag agtcatcacc aatccctaat ctcaagtaat cagggacaca      180
aacactgcgg aaggccgcag ggtcctctgc ctaggaaaac cagagacctt tgttcacttg      240
tttatctgac cttccctcca ctattgtcca tgaccctgcc aaatccccct ctgtgagaaa      300
cacccaagaa ttatcaataa aaaataaatt taaaaaaaa aatacaaaaa aaaaaaaaa       360 aaaaaaaaaa gacttacgaa tagttattga taaatgaata gctattggta aagccaagta      420
aatgatcata ttcaaaacca gacggccatc atcacagctc aagtctacct gatttgatct      480
ctttatcatt gtcattcttt ggattcacta gattagtcat catcctcaaa attctccccc      540
aagttctaat tacgttccaa acatttaggg gttacatgaa gcttgaacct actaccttct      600
ttgcttttga gccatgagtt gtaggaatga tgagtttaca ccttacatgc tggggattaa      660
tttaaacttt acctctaagt cagttgggta gcctttggct tattttttgta gctaattttg      720 tagttaatgg atgcactgtg aatcttgcta tgatagtttt cctccacact ttgccactag      780
gggtaggtag gtactcagtt ttcagtaatt gcttacctaa gaccctaagc cctatttctc      840
ttgtactggc ctttatctgt aatatgggca tatttaatac aatataattt ttggagtttt      900
tttgtttgtt tgtttgtttg tttttttgag acggagtctt gcatctgtca tgcccaggct      960
ggagtagcag tggtgccatc tcggctcact gcaagctcca cctcccgagt tcacgccatt     1020
ttcctgcctc agcctcccga gtagctggga ctacaggcgc cgccaccat gcccggctaa     1080
```

```
tttttttgtat ttttggtaga gacggggttt caccgtgtta gccagaatgg tctcgatctc    1140
ctgacttcgt gatccacccg cctcggcctc ccaaagttct gggattacag gtgtgagcca    1200
ccgcacctgg ccaattttt  gagtctttta aagtaaaaat atgtcttgta agctggtaac    1260
tatggtacat ttcctttat  taatgtggtg ctgacggtca tataggttct tttgagtttg    1320
gcatgcatat gctactttt  gcagtccttt cattacattt ttctctcttc atttgaagag    1380
catgttatat cttttagctt cacttggctt aaaaggttct ctcattagcc taacacagtg    1440
tcattgttgg taccacttgg atcataagtg aaaaacagt  caagaaattg cacagtaata    1500
cttgtttgta agagggatga ttcaggtgaa tctgacacta agaaactccc ctacctgagg    1560
tctgagattc ctctgacatt gctgtatata ggcttttcct ttgacagcct gtgactgcgg    1620 actattttc  ttaagcaaga tatgctaaag ttttgtgagc ctttttccag agagaggtct    1680
catatctgca tcaagtgaga acatataatg tctgcatgtt tccatatttc aggaatgttt    1740
gcttgtgttt tatgctttta tatagacagg gaaacttgtt cctcagtgac ccaaaagagg    1800
tgggaattgt tattggatat catcattggc ccacgctttc tgaccttgga aacaattaag    1860
ggttcataat ctcaattctg tcagaattgg tacaagaaat agctgctatg tttcttgaca    1920
ttccacttgg taggaaataa gaatgtgaaa ctcttcagtt ggtgtgtgtc cctngttttt    1980
ttgcaatttc cttcttactg tgttaaaaaa aagtatgatc ttgctctgag aggtgaggca    2040
ttcttaatca tgatctttaa agatcaataa tataatcctt tcaaggatta tgtctttatt    2100
ataataaaga taatttgtct ttaacagaat caataatata atcccttaaa ggattatatc    2160
tttgctgggc gcagtggctc acacctgtaa tcccagcact tgggtggcc  aaggtggaag    2220 gatcaaattt gcctacttct atattatctt ctaaagcaga attcatctct cttccctcaa    2280
tatgatgata ttgacagggt ttgccctcac tcactagatt gtgagctcct gctcagggca    2340
ggtagngttt tttgttttg  ttttgtttt  tcttttttga cagggtct  tgctctgtca    2400 cccaggccag agtgcaatgg tacagtctca gctcactgca gcctcaacgc ctcggctcaa    2460
accatcatcc catttcagcc tcctgagtag ctgggactac aggcacatgc cattacacct    2520
ggctaatttt tttgtatttc tagtagagac agggtttggc catgttgccc gggctggtct    2580
cgaactcctg gactcaagca atccacccac ctcagcctcc caaaatgagg gaccgtgtct    2640
tattcatttc catgtcccta gtccatagcc cagtgctgga cctatggtag tactaaataa    2700
atatttgttg aatgcaatag taaatagcat ttcagggagc aagaactaga ttaacaaagg    2760
tggtaaaagg tttggagaaa aaaataatag tttaatttgg ctagagtatg agggagagta    2820
gtaggagaca agatggaaag gtctcttggg caaggttttg aaggaagttg aagtcagaa     2880 gtacacaatg tgatatcgtg gcaggcagtg gggagccaat gaaggctttt gagcaggaga    2940
gtaatgtgtt gaaaaataaa tataggttaa acctatcaga gcccctctga cacatacact    3000
tgcttttcat tcaagctcaa gtttgtctcc cacatcccca ttacttaact caccctcggg    3060
ctcccctagc agcctgccct acctctttac ctgcttcctg gtggagtcag ggatgtatac    3120
atgagctgct ttccctctca gccagagaca tggggggccc cagctcccct gcctttcccc    3180
ttctgtgcct ggagctggga agcaggccag ggttagctga ggctggctgg caagcagctg    3240
ggtggtgcca gggagagcct gcatagtgcc aggtggtgcc ttgggttcca agctagtcca    3300 tggcccccgat aaccttctgc ctgtgcacac acctgcccct cactccaccc ccatcctagc    3360
tttggtatgg gggagagggc acagggccag acaaacctgt gagactttgg ctccatctct    3420
gcaaaagggc gctctgtgag tcagcctgct cccctccagg cttgctcctc ccccacccag    3480
```

```
ctctcgtttc caatgcacgt acagcccgta cacaccgtgt gctgggacac cccacagtca    3540
gcgcatggct cccctgtgcc ccagcccctg gctccctctg ttgatcccgg ccctgctcc     3600
aggcctcact gtgcaactgc tgctgtcact gctgcttctg atgcctgtcc atccccagag    3660
gttgccccgg atgcaggagg attccccctt ggaggaggct cttctgggga agatgaccca    3720
ctgggcgagg aggatctgcc cagtgaagag gattcaccca gagaggagga tccacccgga    3780
gaggaggatc tacctggaga ggaggatcta cctggagagg aggatctacc tgaagttaat    3840
gcctaaatca gaagaagagg gctccctgaa gttagaggat ctacctactg ttgaggctcc    3900
tggagatcct caagaacccc agaataatgc ccacagggac aaagaagggg atgaccagag    3960
tcattggcgc tatggaggcg acccgcctgg ccccgggtgt ccccagcctg cgcgggccgc    4020
ttccagtccc cggtggatat ccgccccag ctcgccgcct tctgcccggc cctgcgcccc     4080
ctggaactcc tgggcttcca gctcccgccg ctcccagaac tgcgcctgca gacaatggcc    4140
acagtgtgca actgaccctg cctcctgggc tagagatggc tctgggtccc gggcgggagt    4200
accggctctg cagctgcatc tgcactgggg ggctgcaggt cgtccgggct cggagcacac    4260
tgtggaaggc caccgtttcc ctgccgagat ccacgtggtt cacctcagca ccgccttgc     4320
cagagttgac gaggccttgg ggcgcccggg aggcctggcc gtgttggcgc ctttctggag    4380
gagggccccgg aagaaaacag tgtcctatga gcagttgctg tctcgcttgg aagaaatcgc   4440
tgaggaaggc tcagagactc aggtcccagg actggacata tctgcactcc tgccctctga    4500
cttcagccgc tacttccaat atgagggggtc tctgactaca ccgccctgtg cccagggtgt   4560
catctggact gtgtttaacc agacagtgat gctgagtgct aagcagctcc acccctctc    4620
tgacaccctg tggggacctg gtgactctcg gctacagctg aacttccgag cgacgcagcc    4680
tttgaatggg cgagtgattg aggcctcctt ccctgctgga gtggacagca gtcctcgggc   4740
tgctgagcca gtccagctga attcctgcct ggctgctggt gacatcctag ccctggtttt    4800
tggcctcctt tttgctgtca ccagcgtcgc gttccttgtg cagatgagaa ggcagcacag    4860
aaggggaacc aaaggggtg tgagcgtacc gcccagcaga ggtagccgag actgagcct    4920
agaggctgga tcttggagaa tgtgagaagc cagccagagg catctgaggg ggagccggta    4980
actgtcctgt cctgctcatt atgccacttc cttttaactg ccaagaaatt ttttaaaata    5040
aatatttata at                                                       5052
```

<210> SEQ ID NO 24
<211> LENGTH: 6
<212> TYPE: PRT
<213> ORGANISM: HUMAN

<400> SEQUENCE: 24

Arg Arg Ala Arg Lys Lys
 1               5

<210> SEQ ID NO 25
<211> LENGTH: 4
<212> TYPE: PRT
<213> ORGANISM: HUMAN
<220> FEATURE:
<221> NAME/KEY: SITE
<222> LOCATION: (1)..(4)

<400> SEQUENCE: 25

Ser Pro Xaa Xaa
 1

```
<210> SEQ ID NO 26
<211> LENGTH: 4
<212> TYPE: PRT
<213> ORGANISM: HUMAN
<220> FEATURE:
<221> NAME/KEY: SITE
<222> LOCATION: (1)..(4)

<400> SEQUENCE: 26

Thr Pro Xaa Xaa
  1
```

MN GENE AND PROTEIN

This application is a continuation application of U.S. Ser. No. 10/795,933 (filed Mar. 8, 2004), now abandoned, which is a continuation application of U.S. Ser. No. 08/260,190 (filed Jun. 15, 1994) which issued on Aug. 10, 2004 as U.S. Pat. No. 6,774,117, which is a continuation-in-part of U.S. Ser. No. 08/177,093 (filed Dec. 30, 1993) which issued on Apr. 18, 2000 as U.S. Pat. No. 6,051,226, which is in turn a continuation-in-part of U.S. Ser. No. 07/964,589 (filed Oct. 21, 1992) which issued on Feb. 7, 1995 as U.S. Pat. No. 5,387,676. This application declares priority under 35 USC §120 from those U.S. applications, and also under 35 USC §119 from Czechoslovakian patent application PV-709-92 (filed Mar. 11, 1992).

FIELD OF THE INVENTION

The present invention is in the general area of medical genetics and in the fields of biochemical engineering and immunochemistry. More specifically, it relates to the identification of a new gene—the MN gene—a cellular gene coding for the MN protein. The inventors hereof found MN proteins to be associated with tumorigenicity. Evidence indicates that the MN protein appears to represent a potentially novel type of oncoprotein. Identification of MN antigen as well as antibodies specific therefor in patient samples provides the basis for diagnostic/prognostic assays for cancer.

BACKGROUND OF THE INVENTION

A novel quasi-viral agent having rather unusual properties was detected by its capacity to complement mutants of vesicular stomatitis virus (VSV) with heat-labile surface G protein in HeLa cells (cell line derived from human cervical adenocarcinoma), which had been cocultivated with human breast carcinoma cells. [Zavada et al., *Nature New Biol.*, 240: 124 (1972); Zavada et al., *J. Gen. Virol.*, 24: 327 (1974); Zavada, J., *Arch. Virol.*, 50: 1 (1976); Zavada, J., *J. Gen. Virol.*, 63: 15-24 (1982); Zavada and Zavadova, *Arch, Virol.*, 118: 189 (1991).] The quasi viral agent was called MaTu as it was presumably derived from a human mammary tumor.

There was significant medical interest in studying and characterizing MaTu as it appeared to be an entirely new type of molecular parasite of living cells, and possibly originated from a human tumor. Described herein is the elucidation of the biological and molecular nature of MaTu which resulted in the discovery of the MN gene and protein. MaTu was found by the inventors to be a two-component system, having an exogenous transmissible component, MX, and an endogenous cellular component, MN. As described herein, the MN component was found to be a cellular gene, showing only very little homology with known DNA sequences. The MN gene was found to be present in the chromosomal DNA of all vertebrates tested, and its expression was found to be strongly correlated with tumorigenicity.

The exogenous MaTu-MX transmissible agent was identified as lymphocytic choriomeningitis virus (LCMV) which persistently infects HeLa cells. The inventors discovered that the MN expression in HeLa cells is positively regulated by cell density, and also its expression level is increased by persistent infection with LCMV.

Research results provided herein show that cells transfected with MN cDNA undergo changes indicative of malignant transformation. Further research findings described herein indicate that the disruption of cell cycle control is one of the mechanisms by which MN may contribute to the complex process of tumor development.

Described herein is the cloning and sequencing of the MN gene and the recombinant production of MN proteins. Also described are antibodies prepared against MN proteins/polypeptides. MN proteins/polypeptides can be used in serological assays according to this invention to detect MN-specific antibodies. Further, MN proteins/polypeptides and/or antibodies reactive with MN antigen can be used in immunoassays according to this invention to detect and/or quantitate MN antigen. Such assays may be diagnostic and/or prognostic for neoplastic/pre-neoplastic disease.

SUMMARY OF THE INVENTION

Herein disclosed is the MN gene, a cellular gene which is the endogenous component of the MaTu agent. cDNA sequences for the MN gene are shown in FIGS. 1A-B [SEQ. ID. NO.: 1] and FIG. 15 [SEQ. ID. NO.: 5]. FIG. 25 provides the sequence of a MN genomic clone containing a promoter region [SEQ. ID. NO.: 23].

This invention is directed to said MN gene, fragments thereof and the related cDNA which are useful, for example, as follows: 1) to produce MN proteins/polypeptides by biochemical engineering; 2) to prepare nucleic acid probes to test for the presence of the MN gene in cells of a subject; 3) to prepare appropriate polymerase chain reaction (PCR) primers for use, for example, in PCR-based assays or to produce nucleic acid probes; 4) to identify MN proteins and polypeptides as well as homologs or near homologs thereto; 5) to identify various mRNAs transcribed from MN genes in various tissues and cell lines, preferably human; and 6) to identify mutations in MN genes. The invention further concerns purified and isolated DNA molecules comprising the MN gene or fragments thereof, or the related cDNA or fragments thereof.

Thus, this invention in one aspect concerns isolated nucleic acid sequences that encode MN proteins or polypeptides wherein the nucleotide sequences for said nucleic acids are selected from the group consisting of:

(a) SEQ. ID. NO.: 1;
(b) SEQ. ID. NO.: 5;
(c) nucleotide sequences that hybridize under stringent conditions to SEQ. ID. NO.: 1 or to its complement;
(d) nucleotide sequences that hybridize under stringent conditions to SEQ. ID. NO.: 5 or to its complement; and
(e) nucleotide sequences that differ from SEQ. ID. NO.: 1 or SEQ. ID NO.: 5, or from the nucleotide sequences of (c) and (d) in codon sequence because of the degeneracy of the genetic code, that is, sequences that are degenerate variants of those sequences. Further, such nucleic acid sequences are selected from nucleotide sequences that but for the degeneracy of the genetic code would hybridize to either SEQ. ID. NO.: 1 or SEQ. ID. NO.: 5 under stringent hybridization conditions.

Further, such isolated nucleic acids that encode MN proteins or polypeptides can also include the MN nucleic acid of the genomic clone shown in FIG. 25a-b, that is, SEQ. ID. NO.: 23, as well as sequences that hybridize to it or its complement under stringent conditions, or would hybridize to SEQ. ID. NO.: 23 or its complement under such conditions, but for the degeneracy of the genetic code.

Further, this invention concerns nucleic acid probes which are fragments of the isolated nucleic acids that encode MN proteins or polypeptides as described above. Preferably said nucleic acid probes are comprised of at least 50 nucleotides, more preferably at least 100 nucleotides, and still more preferably at least 150 nucleotides.

Still further, this invention is directed to isolated nucleic acids selected from the group consisting of:

(a) a nucleic acid having the nucleotide sequence shown in FIG. 25 [SEQ. ID. NO.: 23] and its complement;

(b) nucleic acids that hybridize under standard stringent hybridization conditions to the nucleic acid of (a) or to its complement; and (c) nucleic acids that differ from the nucleic acids of (a) and (b) in codon sequence because of the degeneracy of the genetic code. The invention also concerns nucleic acids that but for the degeneracy of the genetic code would hybridize to the nucleic acid of (a) or to its complement under standard stringent hybridization conditions. The nucleic acids of (b) and (c) that hybridize to the coding region of SEQ. ID. NO.: 23 preferably have a length of at least 50 nucleotides, whereas the nucleic acids of (b) and (c) that hybridize partially or wholly to the non-coding region of SEQ. ID. NO.: 23 or its complement are those that function as nucleic acid probes to identify MN nucleic acid sequences. Conventional technology can be used to determine whether the nucleic acids of (b) and (c) or of fragments of SEQ. ID. NO.: 23 are useful to identify MN nucleic acid sequences, for example, as outlined in Benton and Davis, *Science,* 196: 180 (1977) and Fuscoe et al. *Genomics,* 5: 100 (1989). In general, the nucleic acids of (b) and (c) are preferably at least 50 nucleotides, more preferably at least 100 nucleotides, and still more preferably at least 150 nucleotides.

Test kits of this invention can comprise the nucleic acid probes of the invention which are useful diagnostically/prognostically for neoplastic and/or pre-neoplastic disease. Preferred test kits comprise means for detecting or measuring the hybridization of said probes to the MN gene or to the mRNA product of the MN gene, such as a visualizing means.

Fragments of the isolated nucleic acids of the invention, can also be used as PCR primers to amplify segments of MN genes, and may be useful in identifying mutations in MN genes. Typically, said PCR primers are oligonucleotides, preferably at least 16 nucleotides, but they may be considerably longer. Exemplary primers may be from about 16 nucleotides to about 50 nucleotides, preferably from about 19 nucleotides to about 45 nucleotides.

This invention also concerns nucleic acids which encode MN proteins or polypeptides that are specifically bound by monoclonal antibodies designated M75 that are produced by the hybridoma VU-M75 deposited at the American Type Culture Collection (ATCC) 10801 University Blvd., Manassas, Va. 20110-2209 (USA) under ATCC No. HB 11128, and/or by monoclonal antibodies designated MN12 produced by the hybridoma MN 12.2.2 deposited at the ATCC under ATCC No. HB 11647.

The invention further concerns the discovery of a hitherto unknown protein—MN, encoded by the MN gene. The expression of MN proteins is inducible by growing cells in dense cultures, and such expression was discovered to be associated with tumorigenic cells.

MN proteins were found to be produced by some human tumor cell lines in vitro, for example, by HeLa (cervical carcinoma), T24 (bladder carcinoma) and T47D (mammary carcinoma) and SK-Mel 1477 (melanoma) cell lines, by tumorigenic hybrid cells and by cells of some human cancers in vivo, for example, by cells of uterine cervical, ovarian and endometrial carcinomas as well as cells of some benign neoplasias such as mammary papillomas. MN proteins were not found in non-tumorigenic hybrid cells, and are generally not found in the cells of normal tissues, although they have been found in a few normal tissues, most notably and abundantly in normal stomach tissues. MN antigen was found by immunohistochemical staining to be prevalent in tumor cells and to be present sometimes in morphologically normal appearing areas of tissue specimens exhibiting dysplasia and/or malignancy. Thus, the MN gene is strongly correlated with tumorigenesis and is considered to be a putative oncogene.

In HeLa and in tumorigenic HeLa×fibroblast hybrid (H/F-T) cells, MN protein is manifested as a "twin" protein p54/58N; it is glycosylated and forms disulfide-linked oligomers. As determined by electrophoresis upon reducing gels, MN proteins have molecular weights in the range of from about 40 kd to about 70 kd, preferably from about 45 kd to about 65 kd, more preferably from about 48 kd to about 58 kd. Upon non-reducing gels, MN proteins in the form of oligomers have molecular weights in the range of from about 145 kd to about 160 kd, preferably from about 150 to about 155 kd, still more preferably from about 152 to about 154 kd. The predicted amino acid sequences for preferred MN proteins of this invention are shown in FIG. 1A-1B [SEQ. ID. NO. 2] and in FIG. 15 [SEQ. ID. NO.: 6].

The discovery of the MN gene and protein and thus, of substantially complementary MN genes and proteins encoded thereby, led to the finding that the expression of MN proteins was associated with tumorigenicity. That finding resulted in the creation of methods that are diagnostic/prognostic for cancer and precancerous conditions. Methods and compositions are provided for identifying the onset and presence of neoplastic disease by detecting and/or quantitating MN antigen in patient samples, including tissue sections and smears, cell and tissue extracts from vertebrates, preferably mammals and more preferably humans. Such MN antigen may also be found in body fluids.

MN proteins and genes are of use in research concerning the molecular mechanisms of oncogenesis, in cancer diagnostics/prognostics, and may be of use in cancer immunotherapy. The present invention is useful for detecting a wide variety of neoplastic and/or pre-neoplastic diseases. Exemplary neoplastic diseases include carcinomas, such as mammary, bladder, ovarian, uterine, cervical, endometrial, squamous cell and adenosquamous carcinomas; and head and neck cancers; mesodermal tumors, such as neuroblastomas and retinoblastomas; sarcomas, such as osteosarcomas and Ewing's sarcoma; and melanomas. Of particular interest are head and neck cancers, gynecologic cancers including ovarian, cervical, vaginal, endometrial and vulval cancers; gastrointestinal cancer, such as, stomach, colon and esophageal cancers; urinary tract cancer, such as, bladder and kidney cancers; skin cancer; liver cancer; prostate cancer; lung cancer; and breast cancer. Of still further particular interest are gynecologic cancers; breast cancer; urinary tract cancers, especially bladder cancer; lung cancer; and liver cancer. Even further of particular interest are gynecologic cancers and breast cancer. Gynecologic cancers of particular interest are carcinomas of the uterine cervix, endometrium and ovaries; more particularly such gynecologic cancers include cervical squamous cell carcinomas, adenosquamous carcinomas, adenocarcinomas as well as gynecologic precancerous conditions, such as metaplastic cervical tissues and condylomas.

The invention further relates to the biochemical engineering of the MN gene, fragments thereof or related cDNA. For example, said gene or a fragment thereof or related cDNA can be inserted into a suitable expression vector; host cells can be transformed with such an expression vector; and an MN protein/polypeptide, preferably an MN protein, is expressed therein. Such a recombinant protein or polypeptide can be glycosylated or nonglycosylated, preferably glycosylated, and can be purified to substantial purity. The invention further concerns MN proteins/polypeptides which are synthetically or otherwise biologically prepared.

Said MN proteins/polypeptides can be used in assays to detect MN antigen in patient samples and in serological assays to test for MN-specific antibodies. MN proteins/polypeptides of this invention are serologically active, immunogenic and/or antigenic. They can further be used as immunogens to produce MN-specific antibodies, polyclonal and/or monoclonal, as well as an immune T-cell response.

The invention further is directed to MN-specific antibodies, which can be used diagnostically/prognostically and may be used therapeutically. Preferred according to this invention are MN-specific antibodies reactive with the epitopes represented respectively by the amino acid sequences of the MN protein shown in FIG. 15 as follows: from AA 62 to AA 67 [SEQ. ID. NO.: 10]; from AA 55 to AA 60 [SEQ. ID. NO.: 11]; from AA 127 to AA 147 [SEQ. ID. NO.: 12]; from AA 36 to AA 51 [SEQ. ID. NO.: 13]; from AA 69 to AA 83 [SEQ. ID. NO.: 14]; from AA 279 to AA 291 [SEQ. ID. NO.: 15]; and from AA 450 to AA 462 [SEQ. ID. NO.: 16]. More preferred are antibodies reactive with epitopes represented by SEQ. ID. NOS.: 10, 11 and 12. Still more preferred are antibodies reactive with the epitopes represented by SEQ. ID NOS: 10 and 11, as for example, respectively Mabs M75 and MN12. Most preferred are monoclonal antibodies reactive with the epitope represented by SEQ. ID. NO.: 10.

Also preferred according to this invention are antibodies prepared against recombinantly produced MN proteins as, for example, GEX-3X-MN and MN 20-19. Also preferred are MN-specific antibodies prepared against glycosylated MN proteins, such as, MN 20-19 expressed in baculovirus infected Sf9 cells.

A hybridoma that produces a representative MN-specific antibody, the monoclonal antibody M75 (Mab M75), was deposited the ATCC under Number HB 11128 as indicated above. The M75 antibody was used to discover and identify the MN protein and can be used to identify readily MN antigen in Western blots, in radioimmunoassays and immunohistochemically, for example, in tissue samples that are fresh, frozen, or formalin-, alcohol-, acetone- or otherwise fixed and/or paraffin-embedded and deparaffinized. Another representative MN-specific antibody, Mab MN12, is secreted by the hybridoma MN 12.2.2, which was deposited at the ATCC under the designation HB 11647.

MN-specific antibodies can be used, for example, in laboratory diagnostics, using immunofluorescence microscopy or immunohistochemical staining; as a component in immunoassays for detecting and/or quantitating MN antigen in, for example, clinical samples; as probes for immunoblotting to detect MN antigen; in immunoelectron microscopy with colloid gold beads for localization of MN proteins and/or polypeptides in cells; and in genetic engineering for cloning the MN gene or fragments thereof, or related cDNA. Such MN-specific antibodies can be used as components of diagnostic/prognostic kits, for example, for in vitro use on histological sections; such antibodies can also and used for in vivo diagnostics/prognostics, for example, such antibodies can be labeled appropriately, as with a suitable radioactive isotope, and used in vivo to locate metastases by scintigraphy. Further such antibodies may be used in vivo therapeutically to treat cancer patients with or without toxic and/or cytostatic agents attached thereto. Further, such antibodies can be used in vivo to detect the presence of neoplastic and/or pre-neoplastic disease. Still further, such antibodies can be used to affinity purify MN proteins and polypeptides.

This invention also concerns recombinant DNA molecules comprising a DNA sequence that encodes for an MN protein or polypeptide, and also recombinant DNA molecules that encode not only for an MN protein or polypeptide but also for an amino acid sequence of a non-MN protein or polypeptide. Said non-MN protein or polypeptide may preferably be non-immunogenic to humans and not typically reactive to antibodies in human body fluids. Examples of such a DNA sequence is the alpha-peptide coding region of beta-galactosidase and a sequence coding for glutathione S-transferase or a fragment thereof. However, in some instances, a non-MN protein or polypeptide that is serologically active, immunogenic and/or antigenic may be preferred as a fusion partner to a MN antigen. Further, claimed herein are such recombinant fusion proteins/polypeptides which are substantially pure and non-naturally occurring. An exemplary fusion protein of this invention is GEX-3X-MN.

This invention also concerns methods of treating neoplastic disease and/or pre-neoplastic disease comprising inhibiting the expression of MN genes by administering antisense nucleic acid sequences that are substantially complementary to mRNA transcribed from MN genes. Said antisense nucleic acid sequences are those that hybridize to such mRNA under stringent hybridization conditions. Preferred are antisense nucleic acid sequences that are substantially complementary to sequences at the 5' end of the MN cDNA sequences shown in FIG. 1A-1B and/or in FIG. 15. Preferably said antisense nucleic acid sequences are oligonucleotides.

This invention also concerns vaccines comprising an immunogenic amount of one or more substantially pure MN proteins and/or polypeptides dispersed in a physiologically acceptable, nontoxic vehicle, which amount is effective to immunize a vertebrate, preferably a mammal, more preferably a human, against a neoplastic disease associated with the expression of MN proteins. Said proteins can be recombinantly, synthetically or otherwise biologically produced. Recombinant MN proteins include GEX-3X-MN and MN 20-19. A particular use of said vaccine would be to prevent recidivism and/or metastasis. For example, it could be administered to a patient who has had an MN-carrying tumor surgically removed, to prevent recurrence of the tumor.

The immunoassays of this invention can be embodied in test kits which comprise MN proteins/polypeptides and/or MN-specific antibodies. Such test kits can be in solid phase formats, but are not limited thereto, and can also be in liquid phase format, and can be based on immunohistochemical assays, ELISAs, particle assays, radiometric or fluorometric assays either unamplified or amplified, using, for example, avidin/biotin technology.

ABBREVIATIONS

The following abbreviations are used herein;
AA—amino acid
ATCC—American Type Culture Collection
by—base pairs
BSA—bovine serum albumin
BRL—Bethesda Research Laboratories
CA—carbonic anhydrase
Ci—curie
cm—centimeter
cpm—counts per minute
C-terminus—carboxyl-terminus
° C.—degrees centigrade
DAB—diaminobenzidine
dH$_2$O—deionized water
DMEM—Dulbecco modified Eagle medium
DTT—dithiothreitol
EDTA—ethylenediaminetetracetate EIA—enzyme immunoassay
ELISA—enzyme-linked immunosorbent assay
EtOH—ethanol
F—fibroblasts
FCS—fetal calf serum
FIBR—fibroblasts
FITC—fluorescein isothiocyanate
GEX-3X-MN—fusion protein MN glutathione S-transferase
H—HeLa cells
$H_2O_2$ hydrogen peroxide
HCA—Hydrophobic Cluster Analysis
HEF—human embryo fibroblasts
HeLa K—standard type of HeLa cells
HeLa S—Stanbridge's mutant HeLa D98/AH.2
H/F-T—hybrid HeLa fibroblast cells that are tumorigenic; derived from HeLa D98/AH.2
H/F-N—hybrid HeLa fibroblast cells that are nontumorigenic; derived from HeLa D98/AH.2
HGPRT⁻—hypoxanthine guanine phosphoribosyl transferase-deficient
HLH—helix-loop-helix
HRP—horseradish peroxidase
IPTG—isopropyl-beta-D-thiogalacto-pyranoside
kb—kilobase
kbp—kilobase pairs
kd—kilodaltons
KPL—Kirkegaard & Perry Laboratories, Inc.
LCMV—lymphocytic choriomeningitis virus
LTR—long terminal repeat
M—molar
mA—milliampere.
MAb—monoclonal antibody
ME—mercaptoethanol
MEM—minimal essential medium
min.—minute(s)
mg—milligram
ml—milliliter
mM—millimolar
MMC—mitomycin C
MTV—mammary tumor virus
N—normal concentration
ng—nanogram
NGS—normal goat serum
N-terminus—amino-terminus
ODN—oligodeoxynucleotide
PAGE—polyacrylamide gel electrophoresis
PBS—phosphate buffered saline
PCR—polymerase chain reaction
PEST—combination of one-letter abbreviations for proline, glutamic acid, serine, threonine
pI—isoelectric point
RIP—radioimmunoprecipitation
RIPA—radioimmunoprecipitation assay
SAC—protein A-*Staphylococcus aureus* cells
SDRE—serum dose response element
SDS—sodium dodecyl sulfate
SDS-PAGE—sodium dodecyl sulfate-polyacrylamide gel electrophoresis
SP-RIA—solid-phase radioimmunoassay
SSPE—NaCl (0.18 M), sodium phosphate (0.01 M), EDTA (0.001 M)
TBE—Tris-borate/EDTA electrophoresis buffer
TCA—trichloroacetic acid
TC media—tissue culture media
TMB—tetramethylbenzidine
Tris—tris (hydroxymethyl) aminomethane
µCi—microcurie
µg—microgram
µl—microliter
µM—micromolar
VSV—vesicular stomatitis virus
X-MLV—xenotropic murine leukemia virus Cell Lines The following cell lines were used in the experiments herein described:

HeLa K—standard type of HeLa cells; aneuploid, epithelial-like cell line isolated from a human cervical adenocarcinoma [Gey et al., *Cancer Res.*, 12: 264 (1952); Jones et al., *Obstet. Gynecol.*, 38: 945-949 (1971)] obtained from Professor B. Korych, [Institute of Medical Microbiology and Immunology, Charles University; Prague, Czech Republic]

HeLa D98/AH.2—Mutant HeLa clone that is hypoxanthine (also HeLa S) guanine phosphoribosyl transferase-deficient (HGPRT⁻) kindly provided by Eric J. Stanbridge [Department of Microbiology, College of Medicine, University of California, Irvine, Calif. (USA)] and reported in Stanbridge et al., *Science.* 215: 252-259 (15 Jan. 1982); parent of hybrid cells H/F-N and H/F-T, also obtained from E. J. Stanbridge.

NIH-3T3—murine fibroblast cell line reported in Aaronson, *Science,* 237: 178 (1987).

T47D—cell line derived from a human mammary carcinoma [Keydar et al., *Eur. J. Cancer.* 15: 659-670 (1979)]; kindly provided by J. Keydar [Haddasah Medical School; Jerusalem, Israel]

T24—cell line from urinary bladder carcinoma [Bubenik et al., *Int. J. Cancer,* 11: 765-773 (1973)] kindly provided by J. Bubenik [Institute of Molecular Genetics, Czechoslovak Academy of Sciences; Prague, Czech Republic]

HMB2—cell line from melanoma [Svec et al., *Neoplasma,* 35: 665-681 (1988)]

HEF—human embryo fibroblasts [Zavada et al., *Nature New Biology,* 240: 124-125 (1972)]

SIRC—cell line from rabbit cornea (control and X-MLV-infected) [Zavada et al., *Virology,* 82: 221-231 (1977)]

Vero cells—African green monkey cell line [Zavada et al. (1977)]

myeloma cell line NS-0—myeloma cell line used as a fusion parent in production of monoclonal antibodies [Galfre and Milstein, *Methods Enzmmol.,* 73: 3-46 (1981)]

SK-Mel 1477—human melanoma cell line kindly provided by K. E. Hellstrom [Division of Tumor Immunology, Fred Hutchins Cancer Research Center; Seattle, Wash. (USA)]

XC—cells derived from a rat rhabdomyosarcoma induced with Rous sarcoma virus-induced rat sarcoma [Svoboda, J., *Natl. Cancer Center Institute Monograph No. 17,* IN: "International Conference on Avian Tumor Viruses" (J. W. Beard ed.), pp. 277-298 (1964)], kindly provided by Jan Svoboda [Institute of Molecular Genetics, Czechoslovak Academy of Sciences; Prague, Czech Republic]; and Rat 2-Tk⁻—a thymidine kinase deficient cell line, kindly provided by L. Kutinova [Institute of Sera and Vaccines; Prague, Czech Republic]

CGL1—H/F-N hybrid cells (HeLa D98/AH.2 derivative)
CGL2—H/F-N hybrid cells (HeLa D98/AH.2 derivative)
CGL3—H/F-T hybrid cells (HeLa D98/AH.2 derivative)
CGL4—H/F-T hybrid cells (HeLa D98/Ah.2 derivative)

Nucleotide and Amino Acid Sequence Symbols

The following symbols are used to represent nucleotides herein:

| Base Symbol | Meaning |
| --- | --- |
| A | adenine |
| C | cytosine |
| G | guanine |
| T | thymine |
| U | uracil |
| I | inosine |
| M | A or C |
| R | A or G |
| W | A or T/U |
| S | C or G |
| Y | C or T/U |
| K | G or T/U |
| V | A or C or G |
| H | A or C or T/U |
| D | A or G or T/U |
| B | C or G or T/U |
| N/X | A or C or G or T/U |

There are twenty main amino acids, each of which is specified by a different arrangement of three adjacent nucleotides (triplet code or codon), and which are linked together in a specific order to form a characteristic protein. A three-letter or one-letter convention is used herein to identify said amino acids, as, for example, in FIGS. 1A-B and FIG. 15, respectively, as follows:

| Amino acid name | 3 Ltr. Abbrev. | 1 Ltr. Abbrev. |
| --- | --- | --- |
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Unknown or other | | X |

BRIEF DESCRIPTION OF THE FIGURES

FIG. 1A-1B provides the nucleotide sequence for a MN cDNA [SEQ. ID. NO.: 1] clone isolated as described herein and the predicted amino acid sequence [SEQ. ID. NO.: 2] encoded by the cDNA. That sequence data has been sent to the EMBL Data Library in Heidelberg, Germany and is available under Accession No. X66839.

FIG. 15A-C shows a complete nucleotide sequence of a MN cDNA [SEQ. ID. NO.: 5]. Also shown is the deduced amino acid sequence [SEQ. ID. NO.: 6]. The polyadenylation signal (AATAAA) and the mRNA instability motif (ATTTA) are located at nucleotides (nts) 1507-1512 and at nts 1513-1518, respectively. The amino acid residues of the putative signal peptide as well as the membrane-spanning segment are located at amino acids (aa) 1-37 and at as 415-433, respectively. The N-glycosylation site is located at aa 346. The S/TPXX elements are located at amino acids 7-10, 47-50, 71-74, 153-156, 162-165, 333-336, and 397-400.

FIG. 24 illustrates flow cytometric analyses of asynchronous cell populations of control and MN cDNA-transfected NIH 3T3 cells.

FIG. 25a-b is the complete sequence of an MN genomic clone of this invention [SEQ. ID. NO.: 23]. It is 5052 nucleotides long with the transcription start site at position 3534 (starting with ACAGTCA . . . ). The presumed promoter region is about 300 to 400 nucleotides upstream of the transcription start site.

DETAILED DESCRIPTION

Figure 2:
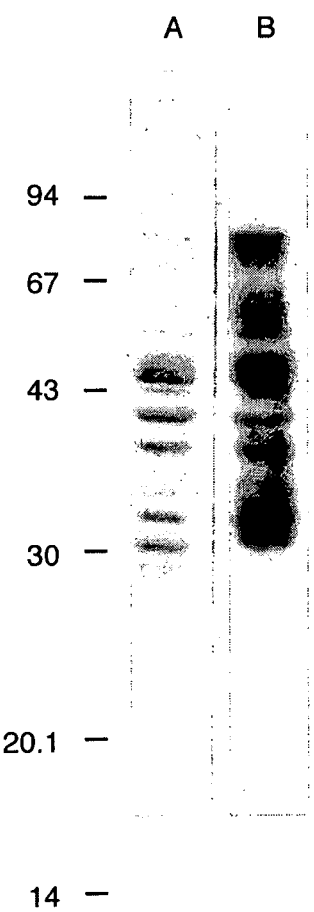
FIG. 2 provides SDS-PAGE and immunoblotting analyses of recombinant MN protein expressed from a pGEX-3X bacterial expression vector. Two parallel samples of purified recombinant MN protein (twenty μg in each sample) were separated by SDS-PAGE on a 10% gel. One sample (A in FIG. 2) was stained with Coomassie brilliant blue; whereas the other sample (B) was blotted onto a Hybond C membrane [Amersham; Aylesbury, Bucks, England]. The blot was developed by autoradiography with $^{125}$I-labeled Mab M75.

As demonstrated herein MaTu was found to be a two-component system. One part of the complex, exogenous MX, is transmissible, and is manifested by a protein, p58X, which is a cytoplasmic antigen which reacts with some natural sera, of humans and of various animals. The other component, MN, is endogenous to human cells. The level of MN expression has been found to be considerably increased in the presence of the MaTu-MX transmissible agent, which has been now identified as lymphocytic choriomeningitis virus (LCMV) which persistently infects HeLa cells.

MN is a cellular gene, showing only very little homology with known DNA sequences. It is rather conservative and is present as a single copy gene in the chromosomal DNA of various vertebrates. Described herein is the cloning and sequencing of the MN cDNA, and the genetic engineering of MN proteins—such as the GEX-3X-MN and MN 20-19 proteins. The recombinant MN proteins can be conveniently purified by affinity chromatography.

MN is manifested in HeLa cells by a twin protein, p54/58N, that is localized on the cell surface and in the nucleus. Immunoblots using a monoclonal antibody reactive with p54/58N (MAb M75) revealed two bands at 54 kd and 58 kd. Those two bands may correspond to one type of protein that differs by glycosylation pattern or by how it is processed. (Both p54N and p58N are glycosylated with oligosaccharidic residues containing mannose, but only p58N also contains glucosamine.) Herein, the phrase "twin protein" indicates p54/58N.

MN is absent in rapidly growing, sparse cultures of HeLa, but is inducible either by keeping the cells in dense cultures or, more efficiently, by infecting them with MX (LCMV). Those inducing factors are synergistic. p54/58N and not p58X is associated with virions of vesicular stomatitis virus (VSV), reproduced in MaTu-infected HeLa. Whereas the twin protein p54/58N is glycosylated and forms oligomers linked by disulfidic bonds, p58X is not glycosylated and does not form S-S-linked oligomers.

VSV assembles p54/58N into virions in HeLa cells, indicating that the twin protein is responsible for complementation of VSV G-protein mutants and for formation of VSV (MaTu) pseudotypes. As only enveloped viruses provide surface glycoproteins for the formation of infectious, functioning pseudotypes, which can perform such specific functions as adsorption and penetration of virions into cells [Zavada, J., *J. Gen. Virol.,* 63: 15-24 (1982)], that observation implies that the MN gene behaves as a quasi-viral sequence.

The surface proteins of enveloped viruses, which participate in the formation of VSV pseudotypes, are glycosylated as is the MN twin protein, p54/58N. MN proteins also resemble viral glycoproteins in the formation of oligomers (preferably tri- or tetramers); such oligomerization, although not necessarily involving S-S bonds (disulfidic bonds), is essential for the assembly of virions [Kreis and Lodish, *Cell,* 46: 929-937 (1986)]. The disulfidic bonds can be disrupted by reduction with 2-mercaptoethanol.

As reported in Pastorekova et al., *Virology,* 187: 620-626 (1992), after reduction with mercaptoethanol, p54/58N from cell extracts or from VSV looks very similar on immunoblot. Without reduction, in cell extracts, it gives several bands around 150 kd, suggesting that the cells may contain several different oligomers (probably with a different p54:p58 ratio), but VSV selectively assembles only one of them, with a molecular weight of about 153 kd. That oligomer might be a trimer, or rather a tetramer, consisting of 54 kd and 58 kd proteins. The equimolar ratio of p54:p58 in VSV virions is indicated by approximately the same strength of 54 kd and 58 kd bands in a VSV sample analyzed under reducing conditions.

The expression of MN proteins appears to be diagnostic/prognostic for neoplastic disease. The MN twin protein, p54/58N, was found to be expressed in HeLa cells and in Stanbridge's tumorigenic (H/F-T) hybrid cells [Stanbridge et al., *Somatic Cell Genet,* 7: 699-712 (1981); and Stanbridge et al., *Science,* 215: 252-259 (1982)] but not in fibroblasts or in non-tumorigenic (H/F-N) hybrid cells (Stanbridge et al., id.). In early studies, MN proteins were found in immunoblots prepared from human ovarian, endometrial and uterine cervical carcinomas, and in some benign neoplasias (as mammary papilloma) but not from normal ovarian, endometrial, uterine or placental tissues. Example 13 details further research on MN gene expression wherein MN antigen, as detected by immunohistochemical staining, was found to be prevalent in tumor cells of a number of cancers, including cervical, bladder, head and neck, and renal cell carcinomas among others. Further, the immunohistochemical staining experiments of Example 13 show that among normal tissues tested, only normal stomach tissues showed routinely and extensively the presence of MN antigen. MN antigen is further shown herein to be present sometimes in morphologically normal-appearing areas of tissue specimens exhibiting dysplasia and/or malignancy.

In HeLa cells infected with MX, observed were conspicuous ultrastructural alterations, that is, the formation of abundant filaments on cell surfaces and the amplification of mitochondria. Using an immunogold technique, p54/58N was visualized on the surface filaments and in the nucleus, particularly in the nucleoli. Thus MN proteins appear to be strongly correlated with tumorigenicity, and do not appear to be produced in general by normal non-tumor cells.

Figure 6A:
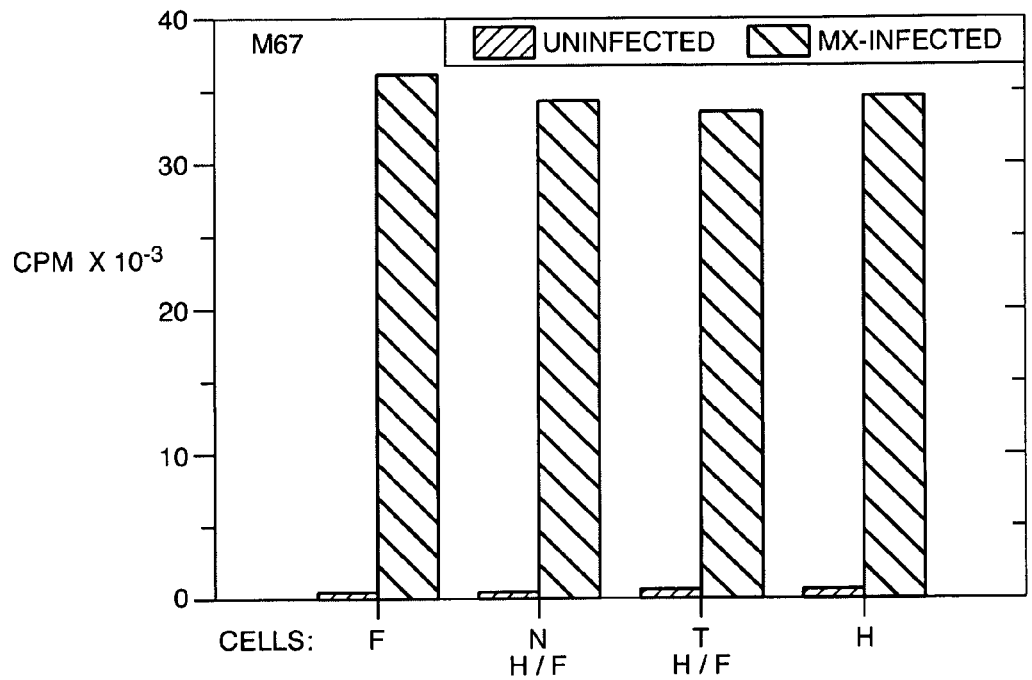
FIG. 6 graphically illustrates the expression of MN- and MX-specific proteins in human fibroblasts (F), in HeLa cells (H) and in H/F-N and H/F-T hybrid cells and contrasts the expression in MX-infected and MX-uninfected cells. Example 5 details the procedures and results.
Figure 6B:
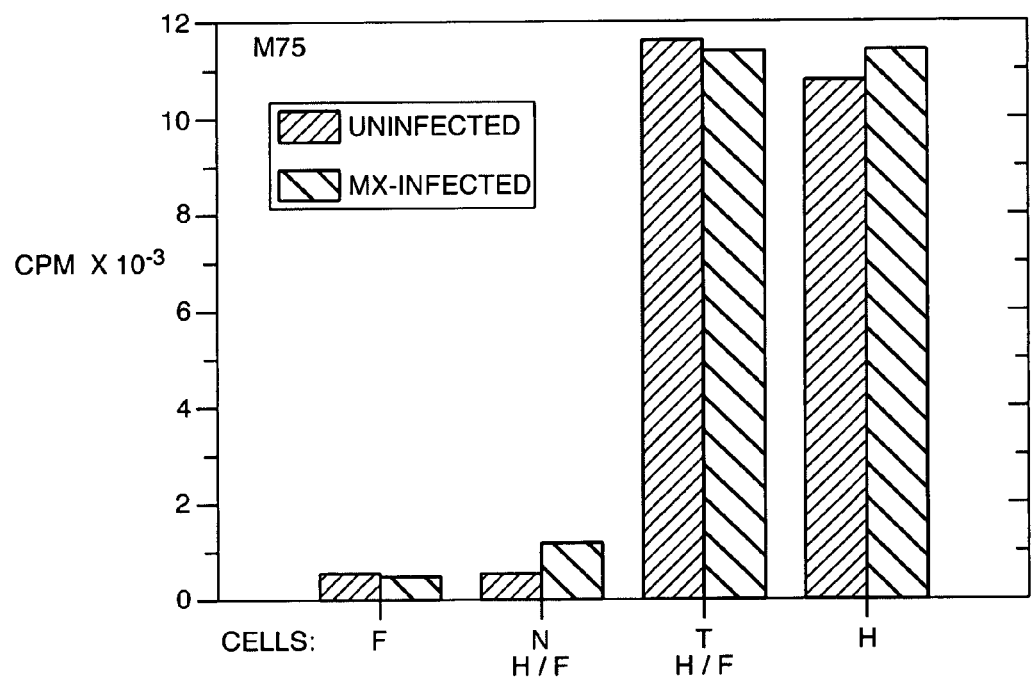
Figure 7:
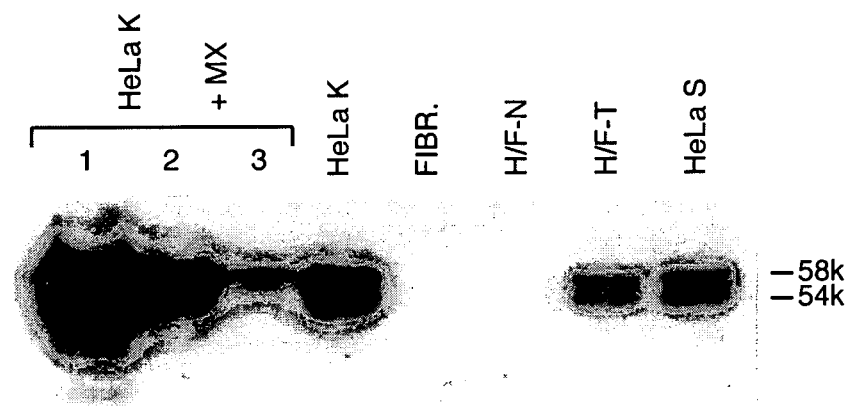
FIG. 7 (discussed in Example 5) provides immunoblots of MN proteins in fibroblasts (FIBR) and in HeLa K, HeLa S, H/F-N and H/F-T hybrid cells.
Figure 12:
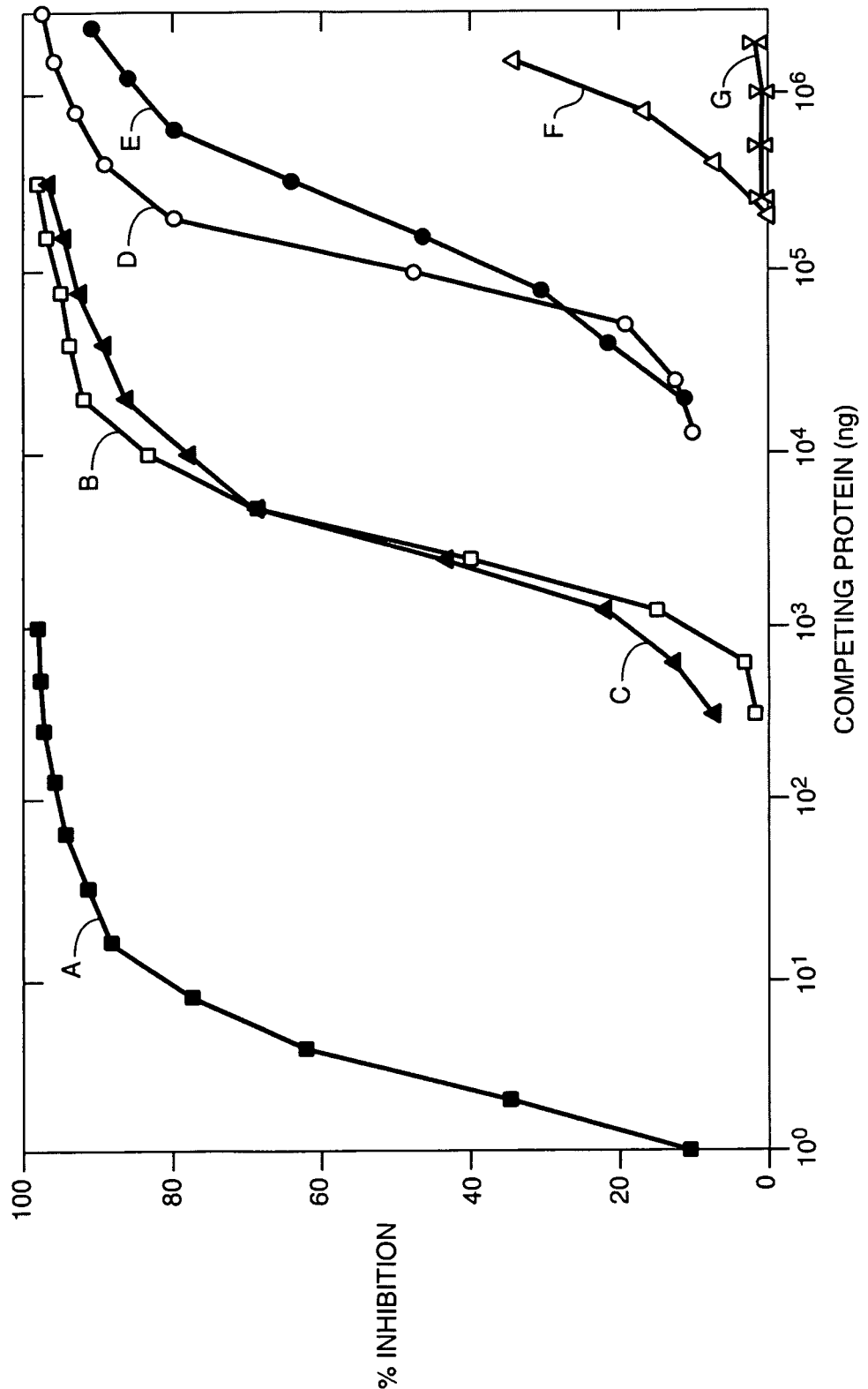
FIG. 12 (discussed in Example 8) shows the results from radioimmunoassays for MN antigen. Ascitic fluid (dilution precipitating 50% radioactivity) was allowed to react for 2 hours with (A) "cold" (unlabeled) protein GEX-3X-MN, or with extracts from cells as follows: (B) HeLa+MX; (C) Rat-2Tk$^-$; (D) HeLa; (E) rat XC; (F) T24; and (G) HEF. Subsequently $^{125}$I-labeled GEX-3X-MN protein ($25 \times 10^3$ cpm/tube) was added and incubated for an additional 2 hours. Finally, the radioactivity to MAb M75 was adsorbed to SAC and measured.

Examples herein show that MX and MN are two different entities, that can exist independently of each other. MX (LCMV) as an exogenous, transmissible agent can multiply in fibroblasts and in H/F-N hybrid cells which are not expressing MN-related proteins (FIG. 6). In such cells, MX does not induce the production of MN protein. MN protein can be produced in HeLa and other tumor cells even in the absence of MX as shown in FIGS. 6-9. However, MX is a potent inducer of MN-related protein in HeLa cells; it increases its production thirty times over the concentration observed in uninfected cells (FIGS. 7 and 12, Table 1 in Example 8, below).

MN Gene-Cloning and Sequencing

FIGS. 1A-1B and 15 provide the nucleotide sequences for MN cDNA clones isolated as described below, respectively SEQ. ID. NOS.: 1 and 5. FIG. 25*a-b* provides the sequence of a MN genomic clone containing a promoter region [SEQ. ID. NO.: 23].

It is understood that because of the degeneracy of the genetic code, that is, that more than one codon will code for one amino acid [for example, the codons TTA, TTG, CTT, CTC, CTA and CTG each code for the amino acid leucine (leu)], that variations of the nucleotide sequences in, for example, SEQ. ID. NOS.: 1, 5, and 23 wherein one codon is substituted for another, would produce a substantially equivalent protein or polypeptide according to this invention. All such variations in the nucleotide sequences' of the MN cDNA and complementary nucleic acid sequences are included within the scope of this invention.

It is further understood that the nucleotide sequences herein described and shown in FIGS. 1A-1B, 15 and 25, represent only the precise structures of the cDNA and genomic nucleotide sequences isolated and described herein. It is expected that slightly modified nucleotide sequences will be found or can be modified by techniques known in the art to code for substantially similar or homologous MN proteins and polypeptides, for example, those having similar epitopes, and such nucleotide sequences and proteins/polypeptides are considered to be equivalents for the purpose of this invention. DNA or RNA having equivalent codons is considered within the scope of the invention, as are synthetic nucleic acid sequences that encode proteins/polypeptides homologous or substantially homologous to MN proteins/polypeptides, as well as those nucleic acid sequences that would hybridize to said exemplary sequences [SEQ. ID. NOS. 1, 5 and 23] under stringent conditions or that but for the degeneracy of the genetic code would hybridize to said cDNA nucleotide sequences under stringent hybridization conditions. Modifications and variations of nucleic acid sequences as indicated herein are considered to result in sequences that are substantially the same as the exemplary MN sequences and fragments thereof.

Partial cDNA Clone

To find the MN gene, a lambda gt11 cDNA library from MX-infected HeLa cells was prepared. Total RNA from MX-infected HeLa cells was isolated by a guanidinium-thiocyanate-CsCl method [Chirgwin et al., *Biochemistry.* 18: 5249 (1979)], and the mRNA was affinity separated on oligo dT-cellulose [Ausubel et al., *Short Protocols in Molecular Biology*, (Greene Publishing Assocs. and Wiley-Interscience; NY, USA, 1989]. The synthesis of the cDNA and its cloning into lambda gt11 was carried out using kits from Amersham, except that the EcoRI-NotI adaptor was from Stratagene [La Jolla, Calif. (USA)]. The library was subjected to immuno-screening with Mab M75 in combination with goat anti-mouse antibodies conjugated with alkaline phosphatase. That immunoscreening method is described in Young and Davis, *PNAS (USA)*, 80: 1194-1198 (1983). About $4 \times 10^5$ primary plaques on *E. coli* Y1090 cells, representing about one-half of the whole library, were screened using Hybond N+ membrane [Amersham] saturated with 10 mM IPTG and blocked with 5% FCS. Fusion proteins were detected with Mab M75 in combination with goat anti-mouse antibodies conjugated with alkaline phosphatase. One positive clone was picked.

pBluescript-MN. The positive clone was subcloned into the NotI site of pBluescript KS [Stratagene] thereby creating pBluescript-MN. Two oppositely oriented nested deletions were made using Erase-a-Base™ kit [Promega; Madison, Wis. (USA)] and sequenced by dideoxy method with a T7 sequencing kit [Pharmacia; Piscataway, N.J. (USA)]. The sequencing showed a partial cDNA clone, the insert being 1397 bp long. That sequence is shown in FIG. 1A-1B. The sequence comprises a large 1290 bp open reading frame and 107 bp 3' untranslated region containing a polyadenylation signal (AATAAA). Another interesting feature of the sequence is the presence of a region contributing to instability of the mRNA (AUUUA at position 1389) which is characteristic for mRNAs of some oncogenes and lymphokines [Shaw and Kamen, *Cell,* 46: 659-667 (1986)]. However, the sequence surrounding the first ATG codon in the open reading frame (ORF) did not fit the definition of a translational start site. In addition, as follows from a comparison of the size of the MN clone with that of the corresponding mRNA in a Northern blot (FIG. 4), the cDNA was missing about 100 bp from the 5' end of its sequence.

Full-Length cDNA Clone

Attempts to isolate a full-length clone from the original cDNA library failed. Therefore, we performed a rapid amplification of cDNA ends (RACE) using MN-specific primers, R1 and R2, derived from the 5' region of the original cDNA clone. The RACE product was inserted into pBluescript, and the entire population of recombinant plasmids was sequenced with an MN-specific primer ODN1. In that way, we obtained a reliable sequence at the very 5' end of the MN cDNA as shown in FIG. 15 [SEQ. ID. NO.: 5].

Specifically, RACE was performed using 5' RACE System [GIBCO BRL; Gaithersburg, Md. (USA)] as follows. 1 µg of mRNA (the same as above) was used as a template for the first strand cDNA synthesis which was primed by the MN-specific antisense oligonucleotide, R1 (5'-TGGGGTTCTTGAG-GATCTCCAGGAG-3') [SEQ. ID. NO.: 7]. The first strand product was precipitated twice in the presence of ammonium acetate and a homopolymeric C tail was attached to its 3' end by TdT. Tailed cDNA was then amplified by PCR using a nested primer, R2 (5'-CTCTAACTTCAGGGAGCCCTCT-TCTT-3') [SEQ. ID. NO.: 8] and an anchor primer that anneals to the homopolymeric tail (5'-CUACUACUACUAG-GCCACGCGTCGACTAGTACGGGI IGGGIIGGGIIG-3') [SEQ. ID. NO.: 9]. Amplified product was digested with BamHI and SalI restriction enzymes and cloned into pBluescript II KS plasmid. After transformation, plasmid DNA was purified from the whole population of transformed cells and used as a template for the sequencing with the MN-specific primer ODN1 [SEQ. ID. NO.: 3; a 29-mer, the sequence for which is shown in Example 10].

The full-length MN cDNA sequence is 1519 base pairs (bp) long (FIG. 15). It contains a single ORF of 1400 bp, starting at position 12, with an ATG codon that is in a good context (GCGCATGG) with the rule proposed for translation initiation [Kozak, *J. Cell. Biol.* 108: 229-241 (1989)]. The AT rich 3' untranslated region contains, as indicated above, a polyadenylation signal (AATAAA) preceding the end of the cDNA by 10 bp. Surprisingly, the sequence from the original clone as well as from four additional clones obtained from the same cDNA library did not reveal any poly(A) tail. Moreover, also as indicated above, just downstream of the poly(A) signal we found an ATTTA motif that is thought to contribute to mRNA instability (Shaw and Kamen, supra). This fact raised possibility that the poly (A) tail is missing due to the specific degradation of the MN mRNA.

Genomic Clone

To study MN regulation, an MN genomic clone was isolated from a human cosmid library prepared from fetal brain using both the MN cDNA probe and the MN-specific primers derived from the 5' end of the cDNA [SEQ. ID. NOS.: 3 and 4; ODN1 AND ODN2; see Example 10]. The sequence for that genomic clone is shown in FIG. 25 [SEQ. ID. NO.: 23]. Sequence analysis revealed that the genomic clone covers a region upstream from the MN transcription start site and ending with the BamHI restriction site localized inside the MN cDNA. Other MN genomic clones can be similarly isolated.

Figure 20:
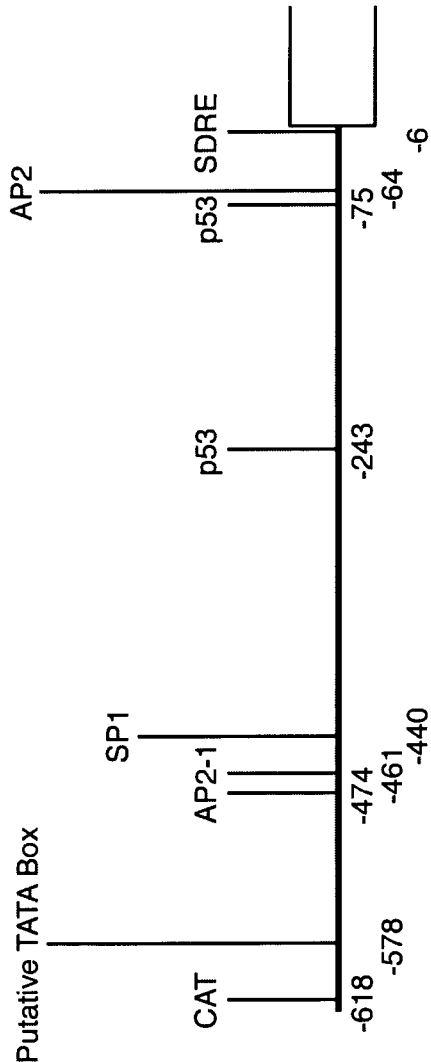
FIG. 20 schematically represents an MN promoter region. The consensus sequences are as follows: CAT-CCAAT; TATA-ATAAATATA; AP2-1-GSSWSCC; AP2-YSSCC-MNSSS [SEQ. ID. NO.: 19]; SP1-KMGGCCKRRY [SEQ. ID. NO.: 20]; p53-RRRCWWGYYY [SEQ. ID. NO.: 21]; and SDRE-CACCSCAC.
Figure 21:
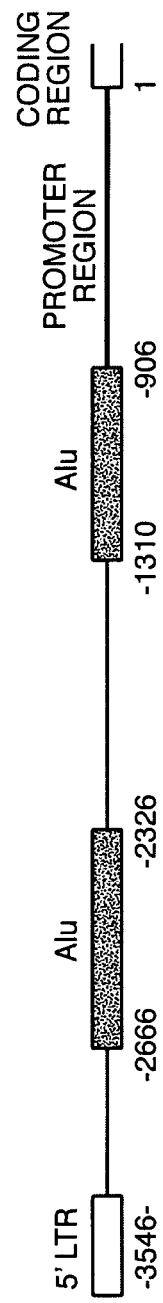
FIG. 21 schematically represents the 5' MN genomic region of an MN genomic clone.

The promoter region is GC-rich and contains one putative TATA-box 578 bp upstream from the transcription start. The promoter contains several consensus sequences for binding sites of regulatory elements, including two p53 sites, two AP-2 sites, an AP-1 site, a SP-1 site, and a SDRE site. FIG. 20 provides a schematic of the MN promoter region, and FIG. 21 provides a schematic of the 5' MN genomic region.

Interestingly, the 5' end region of the isolated genomic clone is strongly homologous to the 5' long terminal repeat (LTR) of human endogenous retroviruses HERV K. As shown in FIG. 21, there is no coding sequence, only two Alu repeats, between the LTR-like region and the promoter. That fact suggests that the LTR, although not necessarily belonging to MN, may provide an enhancer for MN transcription.

Deduced Amino Acid Sequences

The open reading frame of the MN cDNA clone shown in FIG. 1A-1B encodes a putative protein of 422 amino acids with a calculated molecular weight of about 48 kd. The hydrophilicity profile reveals a hydrophobic sequence of amino acids (at positions 371-395) probably representing the region spanning the plasma membrane and containing also a potential cleavage signal. The profile fits well with the observation that p54/58N proteins are localized on the cell membrane. There are no PEST regions in the MN amino acid sequence, suggesting that the product of the MN gene is a stable long-lived protein [Rogers et al., *Science,* 234: 364-368 (1986)]. Such a feature explains our experience with inefficient metabolic labeling of p54/58N. The deduced amino acid sequence displays also other features namely, 10 potential phosphorylation and 7 myristylation sites, and 3 antigenic determinants.

The deduced amino acid sequence from the partial cDNA sequence shown in FIG. 1A-1B can be compared to that shown in FIG. 15A-C from the full-length cDNA. The partial sequence is missing the N-terminal 37 amino acids—the putative signal peptide. The ORF of the MN cDNA shown in FIG. 15A-C has the coding capacity for a 459 amino acid protein with a calculated molecular weight of 51.5 kd. As assessed by amino acid sequence analysis, the deduced primary structure of the MN protein can be divided into four distinct regions. The initial hydrophobic region of 37 amino acids (AA) corresponds to a signal peptide. The mature protein has an N-terminal part of 377 AA, a hydrophobic transmembrane segment of 20 AA and a C-terminal region of 25 AA. The overall amino acid composition is rather basic, with a predicted isoelectric point of 8.92. The MN protein is rich in leucine (11.16%), proline (10.3%), alanine (9.44%), arginine (9.23%), and serine (9.01%).

More detailed insight into MN protein primary structure disclosed the presence of several consensus sequences. One potential N-glycosylation site was found at position 345 of FIG. 15, and a putative nuclear localization signal composed of a stretch of basic amino acids RRARKK [Blank et al., *EMBO J.*, 10: 4159-4167 (1991); Wang and Reed, *Nature*, 364: 121-126 (1993)] was recognized in the middle of the protein, at position 279-284 of FIG. 15. These features, together with the predicted membrane-spanning region mentioned above, are consistent with the results, in which MN was shown to be an N-glycosylated protein localized both in the plasma membrane and in the nucleus. MN protein sequence deduced from cDNA was also found to contain six S/TPXX sequence elements [SEQ. ID. NOS.: 25 AND 26] (one of them is in the signal peptide) defined by Suzuki, *J. Mol. Biol.*, 207: 61-84 (1989) as motifs frequently found in gene regulatory proteins. However, only two of them are composed of the suggested consensus amino acids.

Sequence Similarities and HCA

Computer analysis of the MN cDNA sequence was carried out using DNASIS and PROSID (Pharmacia Software packages). GenBank, EMBL, Protein Identification Resource and SWISS-PROT databases were searched for all possible sequence similarities. In addition, a search for proteins sharing sequence similarities with MN was performed in the MIPS databank with the FastA program [Pearson and Lipman, *PNAS* (USA), 85: 2444 (1988)].

The MN gene was found to clearly be a novel sequence derived from the human genome. Searches for amino acid sequence similarities in protein databases revealed as the closest homology a level of sequence identity (44% of 170 AAs) between the central part of the MN protein [AAs 221-390 of FIG. 15 (SEQ. ID. NO.: 6)] and carbonic anhydrases (CA). However, the overall sequence homology between the cDNA MN sequence and cDNA sequences encoding different CA isoenzymes is in a homology range of 48-50% which is considered by ones in the art to be low. Therefore, the MN cDNA sequence is not closely related to any CA cDNA sequences.

Only very closely related sequences having a homology of at least 80-90% would hybridize to each other under stringent conditions. A sequence comparison of the MN cDNA sequence shown in FIG. 1A-1B and a corresponding cDNA of the human carbonic anhydrase II (CA II) showed that there are no stretches of identity between the two sequences that would be long enough to allow for a segment of the CA II cDNA sequence having 50 or more nucleotides to hybridize under stringent hybridization conditions to the MN cDNA or vice versa.

Although MN deduced amino acid sequences show some homology to known carbonic anhydrases, they differ from them in several respects. Seven carbonic anhydrases are known [Dodgson et al. (eds.), *The Carbonic Anhydrases*, (Plenum Press; New York/London (1991)]. All of the known carbonic anhydrases are proteins of about 30 kd, smaller than the p54/58N-related products of the MN gene. Further, the carbonic anhydrases do not form oligomers as do the MN-related proteins.

Figure 19D:
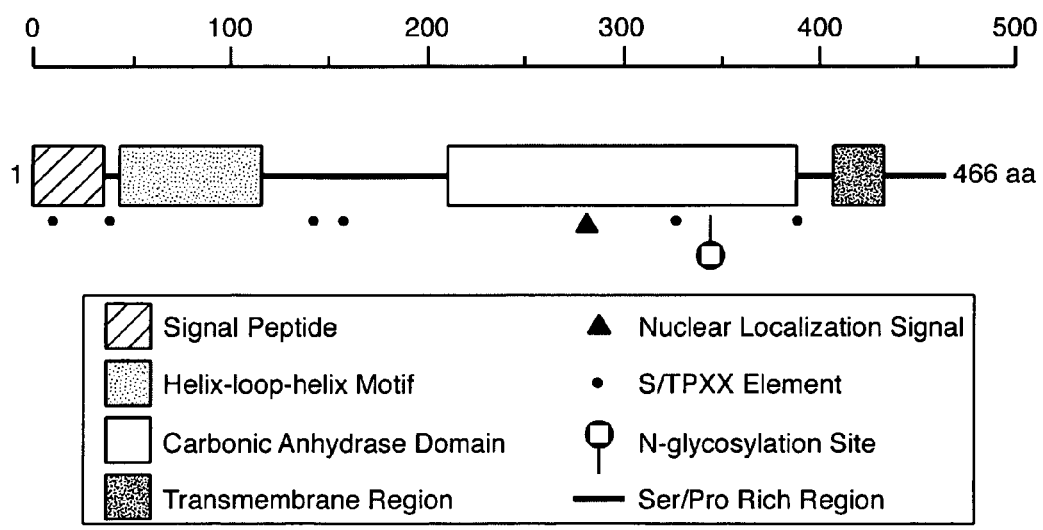
FIG. 19(d) schematically represents the sequence elements and structural domains predicted from the deduced amino acid sequence of MN.
Figure 19A:
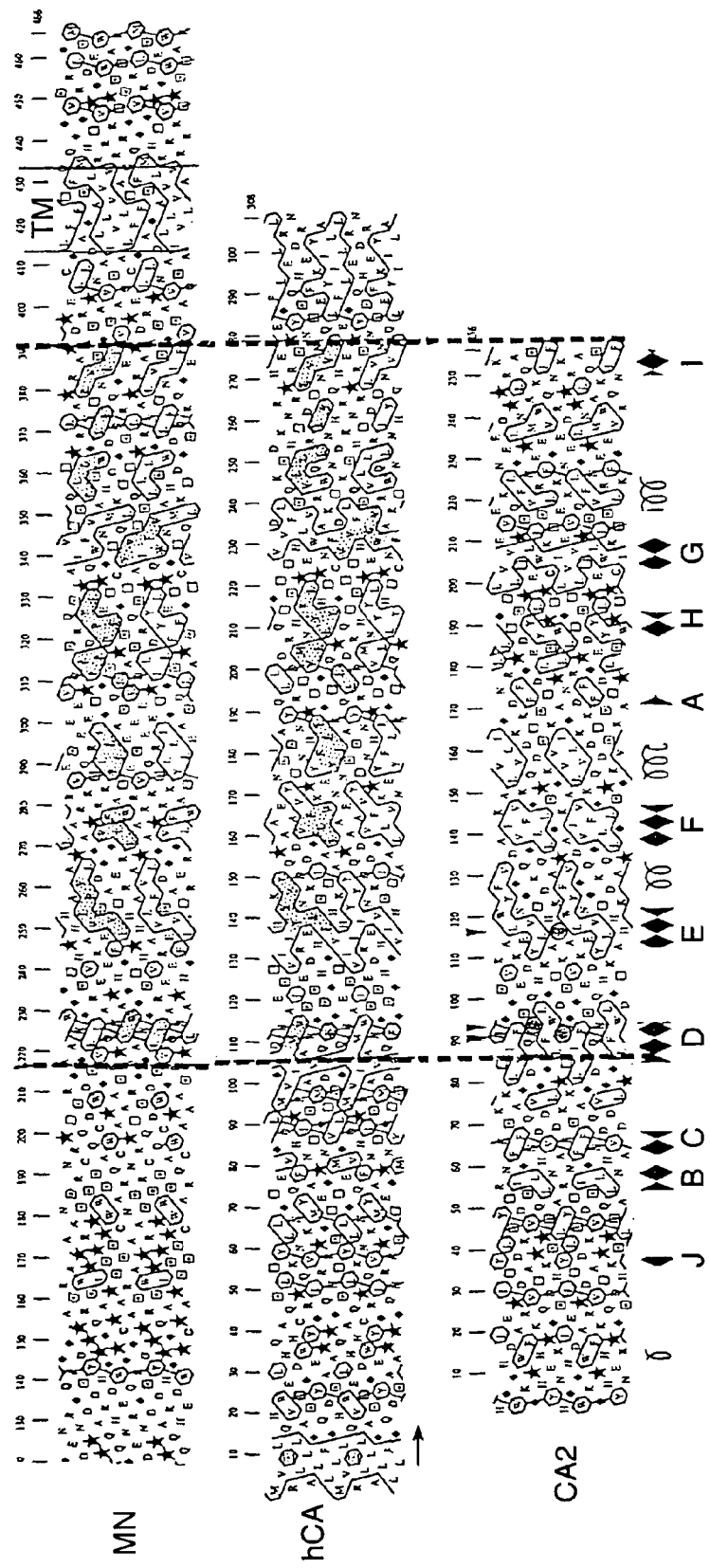
FIG. 19(a) shows an alignment of HCA plots derived from MN, human CA VI (hCA) and CA II (CA2). A one-letter code is used for all amino acids with exception of P (stars), G (diamond-shaped symbol), T and S (open and dotted squares, respectively). Strands D, E, F and G are essential for the structural core of CA. Topologically conserved hydrophobic amino acids are shaded (in hCA VI and MN). Ligands of the catalytic zinc ion (H is residues) are indicated by arrowheads.
Figure 19B:
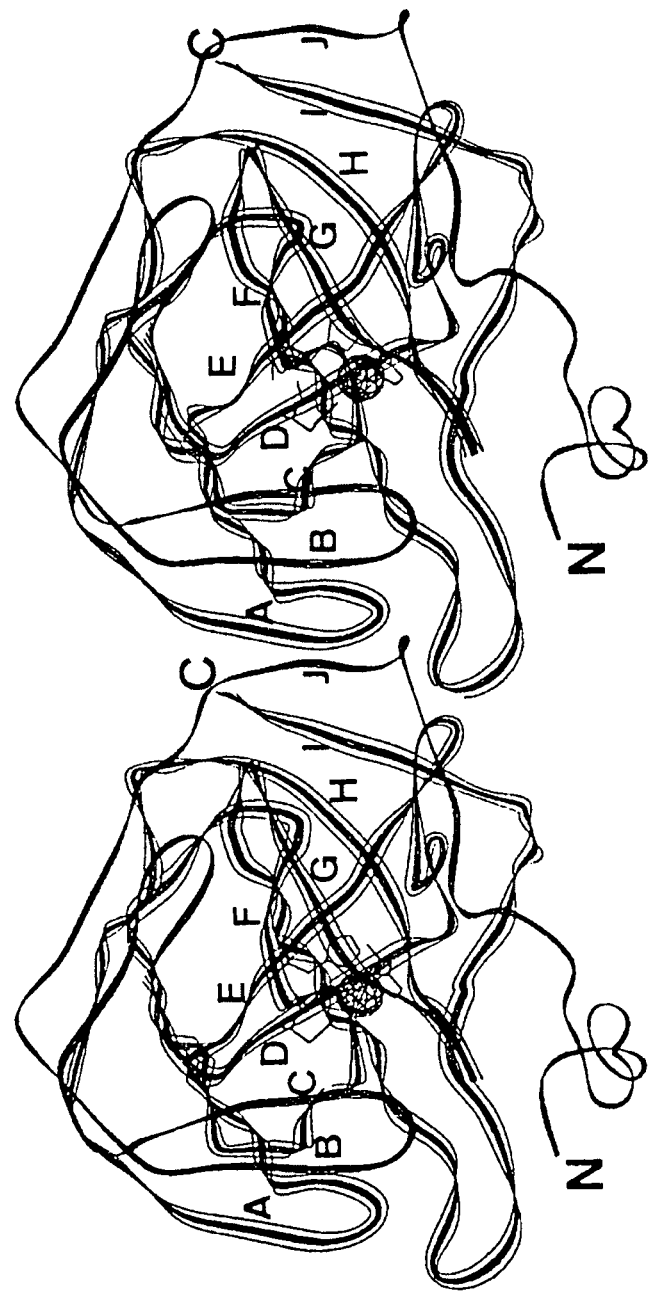
FIG. 19(b) presents a stereoview of the CA II three-dimensional structure illustrating a superposition of the complete CA II structure (thin ribbon) with the structure which is well conserved in MN (open thick ribbon).

HCA. Hydrophobic Cluster Analysis (HCA) was used as a very sensitive method to detect similarities in the secondary and tertiary folding of protein domains even if the sequence homology is low. [Lemesle-Varloot et al., *Biochimie.* 72: 555 (1990); Thoreau et al., *FEBS Lett.,* 282: 26 (1991); Gaboriaud et al., *FEBS Lett.,* 224: 189 (1987).] Comparison of the HCA plots for MN, human CA VI and CA II [FIG. 19(a)] showed that only the middle and C-terminal part of CA are highly conserved in MN with the conserved zinc binding site and the enzyme's active center. A 44% sequence identity and 87% HCA score was calculated between MN and CA VI isoenzyme. [Aldred et al., *Biochemistry.* 30: 569 (1991).] Those values are within the range of those observed for closely related structures [Lemesle-Varloot et al., supra].

Figure 19C:
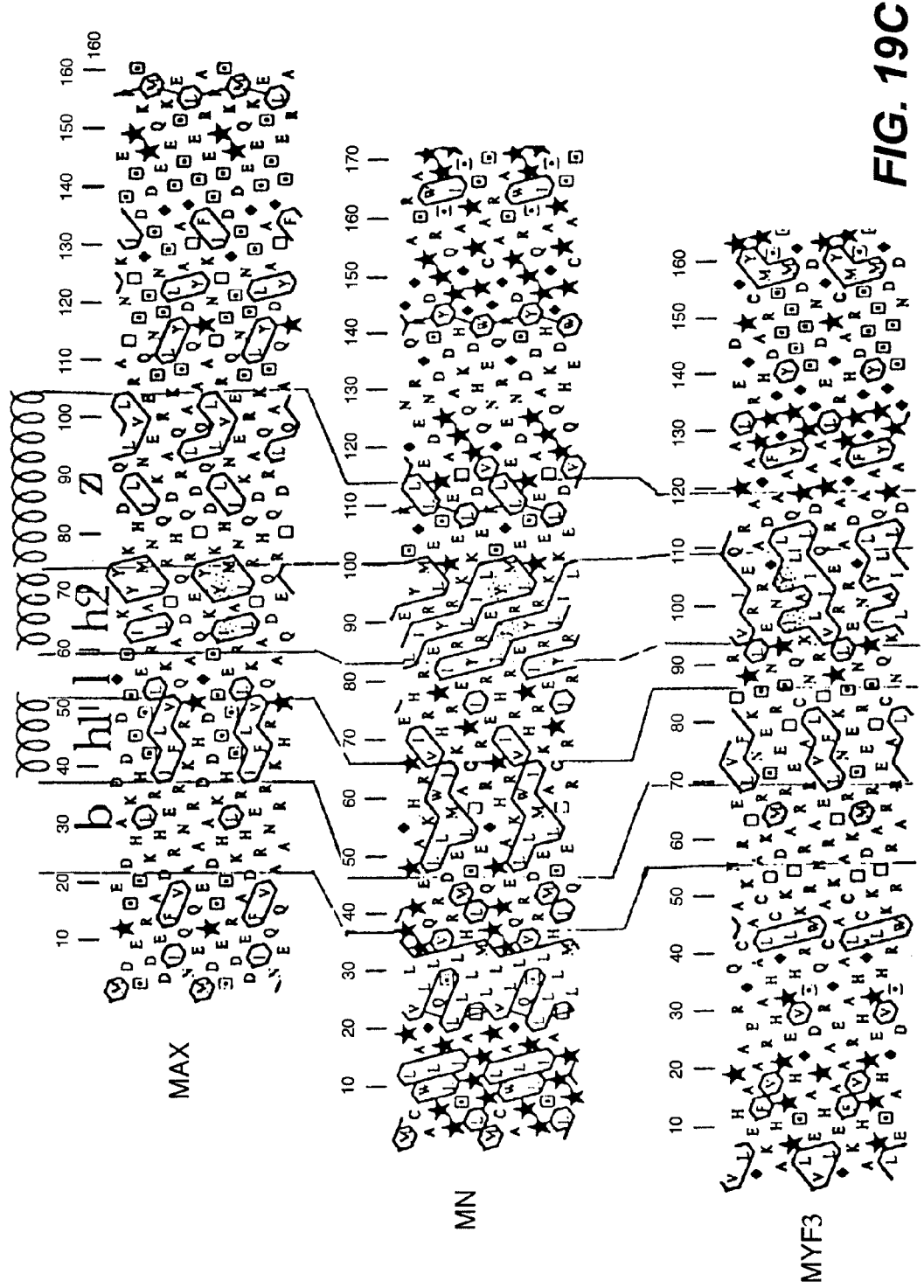
FIG. 19(c) presents an HCA comparison of the basic/helix-loop-helix/zipper domains of Max and Myf-3 with the N-terminal part of MN. The 3D structure of Max is indicated above its plot with delineation of the segments b: basic, h1: helix 1, L: loop, h2: helix 2, z: zipper. The I(6X)Y motif is shaded within helix 2.

HCA was also used in combination with the one-dimensional analysis programs, to analyze the N-terminal part of MN. When screened against the MIPS sequence databank using the FastA program [Pearson and Lipman, supra], the N-terminal segment of MN (AAs 38-114 of SEQ. ID. NO.: 6) repeatedly matched helical protein domains involved in the regulation of gene expression (i.e., transforming protein Myb, accession number S04897; myogenic determination factor Myf-3, accession number S06947; transcriptional activator YAB, accession number JE0416; translational activator PET127, accession number S17029, etc.). HCA suggested [FIG. 19(c)] that although those hits were of low level sequence identity, they might be structurally valid.

The most significant is a predicted structural similarity of MN to members of the HLH protein family—represented by Myf-3 and Max protein. The conserved I(6X)Y motif is revealed in FIG. 19(c), a motif that is a common characteristic of an HLH protein dimerization domain [Ferre-D'Amare et al., *Nature,* 363: 38 (1993)]. The region between the CA-like domain and the putative HLH (covering AAs 120-220 of SEQ. ID. NO.: 6) domain is rich in imperfect repeats of Ser (15%), Pro (16%), Gly and acidic residues with few hydrophobic amino acids, resembling, thus, an activation region of transcription factors. [Lautenberger et al., *Oncogene,* 7: 1713 (1992).]

Figure 22A:
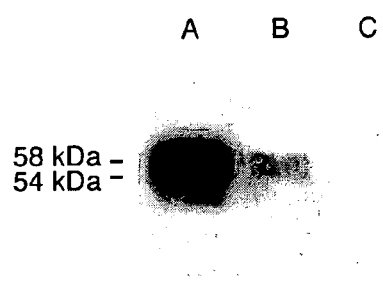
FIG. 22(a) shows the zinc-binding activity of MN protein extracted from HeLa cells persistently infected with LCMV. Samples were concentrated by immunoprecipitation with Mab M75 before loading (A), and after elution from $ZnCl_2$-saturated (B) or $ZnCl_2$-free Fast-Flow chelating Sepharase column (c). Immunoprecipitates were analyzed by Western blotting using iodinated M75 antibody.

In experiments, the results for which are shown in FIG. 22(a), it was determined that MN protein is able to bind zinc cations, as shown by affinity chromatography using Zn-charged chelating sepharose. MN protein immunoprecipitated from HeLa cells by Mab M75 was found to have weak catalytic activity of CA. The CA-like domain of MN has a structural predisposition to serve as a binding site for small soluble domains. Thus, MN protein could mediate some kind of signal transduction.

Figure 22B:
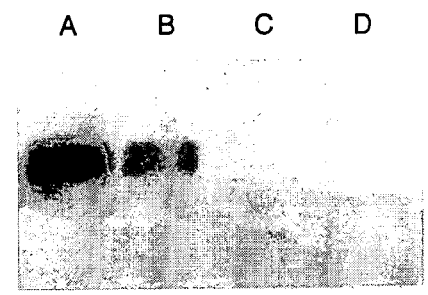
FIG. 22(b) shows MN protein binding to DNA-cellulose. Proteins extracted from LCMV-infected HeLa cells were incubated with DNA-cellulose (A). Proteins that bound to DNA-cellulose in the presence of $ZnCl_2$ and absence of DTT (B), in the presence of both $ZnCl_2$ and DTT (C), and in the absence of both $ZnCl_2$ and DTT (D) were eluted, and all samples were analyzed as above.
Figure 22C:
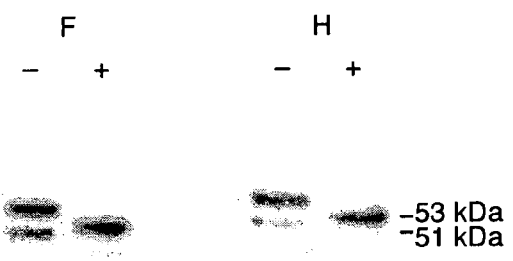
FIG. 22(c) shows the results of endoglycosidase H and F digestion. MN protein immunoprecipitated with Mab M75 was treated with Endo F (F) and Endo H (H). Treated (+) and control samples (-) were analyzed by Western blotting as above.

MN protein from LCMV-infected HeLA cells was shown by using DNA cellulose affinity chromatography [FIG. 22(b)] to bind to immobilized double-stranded salmon sperm DNA. The binding activity required both the presence of zinc cations and the absence of a reducing agent in the binding buffer.

MN Twin Protein

The possibility that the 4 kd difference between the molecular weights of the two MN proteins is caused by different glycosylation was ruled out, since after in vitro treatment with endoglycosidases H and F, respectively, both peptide portions lost about 3 kd in weight. This result indicates, in addition, that the molecular weight of the smaller 54 kd MN protein without its 3 kd sugar moiety, roughly corresponds to the molecular weight of MN calculated from the full-length cDNA. Western blot analysis of MN proteins from cervical carcinoma and normal stomach shows that in both tissues MN protein consists of two 54 and 58 kd peptide portions.

Figure 3:
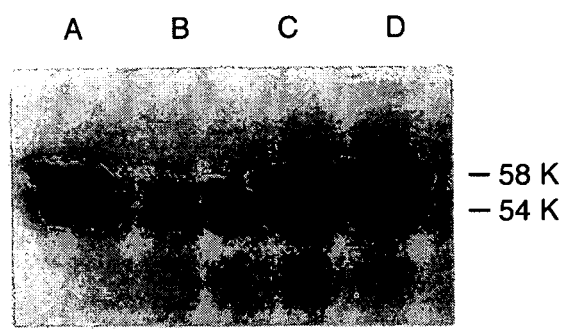
FIG. 3 illustrates inhibition of p54/58 expression by antisense oligodeoxynucleotides (ODNs). HeLa cells cultured in overcrowded conditions were incubated with (A) 29-mer ODN1 [SEQ. ID. NO.: 3]; (B) 19-mer ODN2 [SEQ. ID. NO.: 4]; (C) both ODN1 and ODN2; and (D) without ODNS. Example 10 provides details of the procedures used.

To determine whether both p54/58N proteins were encoded by one gene, antisense ODNs were used to inhibit specifically MN gene expression. [Such use of antisense ODNs is reviewed in Stein and Cohen, *Cancer Res.*, 48: 2659-2668 (1988).] Those experiments are detailed in Example 10. The findings indicated that cultivation of HeLa cells with ODNs resulted in a considerable inhibition of p54/58N synthesis, whereas the amount of different HeLa cell proteins produced remained approximately the same. Further, and importantly, on immunoblotting, the specific inhibition by ODNs affected both of the p54/58N proteins (FIG. 3). Thus, it was concluded that the MN gene that was cloned codes for both of the p54/58N proteins in HeLa cells.

MN Proteins and/or Polypeptides

The phrase "MN proteins and/or polypeptides" (MN proteins/polypeptides) is herein defined to mean proteins and/or polypeptides encoded by an MN gene or fragments thereof. Exemplary and preferred MN proteins according to this invention have the deduced amino acid sequences shown in FIGS. 1A-1B and 15. Preferred MN proteins/polypeptides are those proteins and/or polypeptides that have substantial homology with the MN proteins shown in FIGS. 1A-1B and 15. For example, such substantially homologous MN proteins/polypeptides are those that are reactive with the MN-specific antibodies of this invention, preferably the Mabs M75, MN12 and MN7 or their equivalents.

A "polypeptide" is a chain of amino acids covalently bound by peptide linkages and is herein considered to be composed of 50 or less amino acids. A "protein" is herein defined to be a polypeptide composed of more than 50 amino acids.

MN proteins exhibit several interesting features: cell membrane, and at the same time, nuclear localization (similar to E6 protein of HPV16), cell density dependent expression in HeLa cells, correlation with the tumorigenic phenotype of HeLa×fibroblast somatic cell hybrids, and expression in several human carcinomas among other tissues. As demonstrated herein, for example, in Example 13, MN protein can be found directly in tumor tissue sections but not in general in counterpart normal tissues (exceptions noted infra in Example 13 as in normal stomach tissues). MN is also expressed sometimes in morphologically normal appearing areas of tissue specimens exhibiting dysplasia and/or malignancy. Taken together, these features suggest a possible involvement of MN in the regulation of cell proliferation, differentiation and/or transformation.

It can be appreciated that a protein or polypeptide produced by a neoplastic cell in vivo could be altered in sequence from that produced by a tumor cell in cell culture or by a transformed cell. Thus, MN proteins and/or polypeptides which have varying amino acid sequences including without limitation, amino acid substitutions, extensions, deletions, truncations and combinations thereof, fall within the scope of this invention. It can also be appreciated that a protein extant within body fluids is subject to degradative processes, such as, proteolytic processes; thus, MN proteins that are significantly truncated and MN polypeptides may be found in body fluids, such as, sera. The phrase "MN antigen" is used herein to encompass MN proteins and/or polypeptides.

It will further be appreciated that the amino acid sequence of MN proteins and polypeptides can be modified by genetic techniques. One or more amino acids can be deleted or substituted. Such amino acid changes may not cause any measurable change in the biological activity of the protein or polypeptide and result in proteins or polypeptides which are within the scope of this invention.

The MN proteins and polypeptides of this invention can be prepared in a variety of ways according to this invention, for example, recombinantly, synthetically or otherwise biologically, that is, by cleaving longer proteins and polypeptides enzymatically and/or chemically. A preferred method to prepare MN proteins is by a recombinant means. Particularly preferred methods of recombinantly producing MN proteins are described below for the GEX-3X-MN and MN 20-19 proteins.

Recombinant Production of MN Proteins and Polypeptides

A representative method to prepare the MN proteins shown in FIGS. 1A-1B and 15 or fragments thereof would be to insert the appropriate fragment of MN cDNA into an appropriate expression vector as exemplified below. The fusion protein GEX-3X-MN expressed from XL1-Blue cells is nonglycosylated. Representative of a glycosylated, recombinantly produced MN protein is the MN 20-19 protein expressed from insect cells. The MN 20-19 protein was also expressed in a nonglycosylated form in *E. coli* using the expression plasmid pEt-22b [Novagen].

Baculovirus Expression Systems. Recombinant baculovirus express vectors have been developed for infection into several types of insect cells. For example, recombinant baculoviruses have been developed for among others: *Aedes aegypti, Autographa californica, Bombyx mor, Drosphila melanogaster, Heliothis zea, Spodoptera frugiperda*, and *Trichoplusia ni* [PCT Pub. No. WO 89/046699; Wright, *Nature*, 321: 718 (1986); Fraser et al., *In Vitro Cell Dev. Biol.*, 25: 225 (1989). Methods of introducing exogenous DNA into insect hosts are well-known in the art. DNA transfection and viral infection procedures usually vary with the insect genus to be transformed. See, for example, *Autographa* [Carstens et al., *Virology*, 101: 311 (1980)]; *Spodoptera* [Kang, "Baculovirus Vectors for Expression of Foreign Genes," in: *Advances in Virus Research*, 35 (1988)]; and *Heliothis* (*virescens*) [PCT Pub. No. WO 88/02030].

A wide variety of other host-cloning vector combinations may be usefully employed in cloning the MN DNA isolated as described herein. For example, useful cloning vehicles may include chromosomal, nonchromosomal and synthetic DNA sequences such as various known bacterial plasmids such as pBR322, other *E. coli* plasmids and their derivatives and wider host range plasmids such as RP4, phage DNA, such as, the numerous derivatives of phage lambda, e.g., NB989 and vectors derived from combinations of plasmids and phage DNAs such as plasmids which have been modified to employ phage DNA expression control sequences.

Useful hosts may be eukaryotic or prokaryotic and include bacterial hosts such as *E. coli* and other bacterial strains, yeasts and other fungi, animal or plant hosts such as animal or plant cells in culture, insect cells and other hosts. Of course, not all hosts may be equally efficient. The particular selection of host-cloning vehicle combination may be made by those of skill in the art after due consideration of the principles set forth herein without departing from the scope of this invention.

The particular site chosen for insertion of the selected DNA fragment into the cloning vehicle to form a recombinant DNA molecule is determined by a variety of factors. These include size and structure of the protein or polypeptide to be expressed, susceptibility of the desired protein or polypeptide to endoenzymatic degradation by the host cell components and contamination by its proteins, expression characteristics such as the location of start and stop codons, and other factors recognized by those of skill in the art.

The recombinant nucleic acid molecule containing the MN gene, fragment thereof, or cDNA therefrom, may be employed to transform a host so as to permit that host (transformant) to express the structural gene or fragment thereof and to produce the protein or polypeptide for which the hybrid DNA encodes. The recombinant nucleic acid molecule may also be employed to transform a host so as to permit that host on replication to produce additional recombinant nucleic acid molecules as a source of MN nucleic acid and fragments thereof. The selection of an appropriate host for either of those uses is controlled by a number of factors recognized in the art. These include, for example, compatibility with the chosen vector, toxicity of the co-products, ease of recovery of the desired protein or polypeptide, expression characteristics, biosafety and costs.

Where the host used is an eukaryote, transfection methods such as the use of a calcium phosphate-precipitate, electroporation, conventional mechanical procedures such as microinjection, insertion of a plasmid encapsulated in red blood cell ghosts or in liposomes, treatment of cells with agents such as lysophosphatidyl-choline or use of virus vectors, or the like may be used.

Where the host used is an eucaryote, transfection methods such as the use of a calcium phosphate-precipitate, electroporation, conventional mechanical procedures such as microinjection, insertion of a plasmid encapsulated in red blood cell ghosts or in liposomes, treatment of cells with agents such as lysophosphatidyl-choline or use of virus vectors, or the like may be used.

The level of production of a protein or polypeptide is governed by three major factors: (1) the number of copies of the gene or DNA sequence encoding for it within the cell; (2) the efficiency with which those gene and sequence copies are transcribed and translated; and (3) the stability of the mRNA. Efficiencies of transcription and translation (which together comprise expression) are in turn dependent upon nucleotide sequences, normally situated ahead of the desired coding sequence. Those nucleotide sequences or expression control sequences define, inter alia, the location at which an RNA polymerase interacts to initiate transcription (the promoter sequence) and at which ribosomes bind and interact with the mRNA (the product of transcription) to initiate translation. Not all such expression control sequences function with equal efficiency. It is thus of advantage to separate the specific coding sequences for the desired protein from their adjacent nucleotide sequences and fuse them instead to known expression control sequences so as to favor higher levels of expression. This having been achieved, the newly engineered DNA fragment may be inserted into a multicopy plasmid or a bacteriophage derivative in order to increase the number of gene or sequence copies within the cell and thereby further improve the yield of expressed protein.

Several expression control sequences may be employed. These include the operator, promoter and ribosome binding and interaction sequences (including sequences such as the Shine-Dalgarno sequences) of the lactose operon of $E.\ coli$ ("the lac system"), the corresponding sequences of the tryptophan synthetase system of $E.\ coli$ ("the trp system"), a fusion of the trp and lac promoter ("the tac system"), the major operator and promoter regions of phage lambda ($O_L P_L$ and $O_R P_R$,), and the control region of the phage fd coat protein. DNA fragments containing these sequences are excised by cleavage with restriction enzymes from the DNA isolated from transducing phages that carry the lac or trp operons, or from the DNA of phage lambda or fd. Those fragments are then manipulated in order to obtain a limited population of molecules such that the essential controlling sequences can be joined very close to, or in juxtaposition with, the initiation codon of the coding sequence.

The fusion product is then inserted into a cloning vehicle for transformation or transfection of the appropriate hosts and the level of antigen production is measured. Cells giving the most efficient expression may be thus selected. Alternatively, cloning vehicles carrying the lac, trp or lambda $P_L$ control system attached to an initiation codon may be employed and fused to a fragment containing a sequence coding for a MN protein or polypeptide such that the gene or sequence is correctly translated from the initiation codon of the cloning vehicle.

The phrase "recombinant nucleic acid molecule" is herein defined to mean a hybrid nucleotide sequence comprising at least two nucleotide sequences, the first sequence not normally being found together in nature with the second.

The phrase "expression control sequence" is herein defined to mean a sequence of nucleotides that controls and regulates expression of structural genes when operatively linked to those genes.

The following are representative examples of genetically engineering MN proteins of this invention. The descriptions are exemplary and not meant to limit the invention in any way.
Production of Fusion Protein GEX-3X-MN To confirm whether the partial cDNA clone codes for the p54/58N-specific protein, it was subcloned into the bacterial expression vector pGEX-3X [Pharmacia; Upsala, Sweden], constructed to express a fusion protein containing the C-terminus of glutathione S-transferase. The partial cDNA insert from the above-described pBluescript-MN was released by digesting the plasmid DNA by NotI. It was then treated with S1 nuclease to obtain blunt ends and then cloned into a dephosphorylated SmaI site of pGEX-3X (Pharmacia). After transformation of XL1-Blue cells [$E.\ coli$ strain; Stratagene] and induction with IPTG, a fusion protein was obtained.

The fusion protein—MN glutathione S-transferase (GEX-3X-MN) was purified by affinity chromatography on Glutathione-S-Sepharose 4B (Pharmacia). Twenty micrograms of the purified recombinant protein in each of two parallel samples were separated by SDS-PAGE on a 10% gel. One of the samples (A) was stained with Coomassie brilliant blue, whereas the other (B) was blotted onto a Hybond C membrane [Amersham]. The blot was developed by autoradiography with $^{125}$I-labeled MAb M75. The results are shown in FIG. 2.

SDS-PAGE analysis provided an interesting result: a number of protein bands with different molecular weights (FIG. 2A). A similar SDS-PAGE pattern was obtained with another representative fusion protein produced according to this invention, beta-galactosidase-MN that was expressed from lambda gt11 lysogens. It appears that those patterns are due to translation errors caused by the presence of 9 AGGAGG codon tandems in the MN sequence. The use of those codons is strongly avoided in bacterial genes because of the shortage of corresponding tRNAs. Thus, during the translation of AGGAGG tandems from foreign mRNA, +1 ribosomal frameshifts arise with a high frequency (about 50%) [Spanjaard et al., *Nuc. Acid Res.* 18: 5031-5036 (1990)].

By immunoblotting, a similar pattern was obtained: all the bands seen on stained SDS-PAGE gel reacted with the MN-specific MAb 75 (FIG. 2B), indicating that all the protein bands are MN-specific. Also, that result indicates that the binding site for MAb M75 is on the N-terminal part of the MN protein, which is not affected by frameshifts.

As shown in Example 8 below, the fusion protein GEX-3X-MN was used in radioimmunoassays for MN-specific antibodies and for MN antigen.

Expression of MN 20-19 Protein

Another representative, recombinantly produced MN protein of this invention is the MN 20-19 protein which, when produced in baculovirus-infected Sf9 cells [*Spodoptera frugiperda* cells; Clontech; Palo Alto, Calif. (USA)], is glycosylated. The MN 20-19 protein misses the putative signal peptide (AAs 1-37) of SEQ. ID. NO.: 6 (FIG. 15), has a methionine (Met) at the N-terminus for expression, and a Leu-Glu-His-His-His-His-His-His [SEQ. ID NO.: 22] added to the C-terminus for purification. In order to insert the portion of the MN coding sequence for the GEX-3X-MN fusion protein into alternate expression systems, a set of primers for PCR was designed. The primers were constructed to provide restriction sites at each end of the coding sequence, as well as in-frame start and stop codons. The sequences of the primers, indicating restriction enzyme cleavage sites and expression landmarks, are shown below.

```
Primer #20: N-terminus
                                          [SEQ. ID. NO. 17]
                       [Translation start
5'GTCGCTAGCTCCATGGGTCATATGCAGAGGTTGCCCCGGATGCAG 3'
    NheI   NcoI     NdeI  |MN cDNA #1

Primer #19: C-terminus
                                          [SEQ. ID. NO. 18]
            [Translation stop
5'GAAGATCTCTTACTCGAGCATTCTCCAAGATCCAGCCTCTAGG 3'
    BglII      XhoI  |MN cDNA
```

The SEQ. ID. NOS.: 17 and 18 primers were used to amplify the MN coding sequence present in the pGEX-3X-MN vector using standard PCR techniques. The resulting PCR product (termed MN 20-19) was electrophoresed on a 0.5% agarose/1×TBE gel; the 1.3 kb band was excised; and the DNA recovered using the Gene Clean II kit according to the manufacturer's instructions [Bio101; LaJolla, Calif. (USA)].

MN 20-19 and plasmid pET-22b [Novagen, Inc.; Madison, Wis. (USA)] were cleaved with the restriction enzymes NdeI and XhoI, phenol-chloroform extracted, and the appropriate bands recovered by agarose gel electrophoresis as above. The isolated fragments were ethanol co-precipitated at a vector:insert ratio of 1:4. After resuspension, the fragments were ligated using T4 DNA ligase. The resulting product was used to transform competent Novablue *E. coli* cells [Novagen, Inc.]. Plasmid mini-preps [Magic Minipreps; Promega] from the resultant ampicillin resistant colonies were screened for the presence of the correct insert by restriction mapping. Insertion of the gene fragment into the pET-22b plasmid using the NdeI and XhoI sites added a 6-histidine tail to the protein that could be used for affinity isolation.

To prepare MN 20-19 for insertion into the baculovirus expression system, the MN 20-19 gene fragment was excised from pET-22b using the restriction endonucleases XbaI and PvuI. The baculovirus shuttle vector pBacPAK8 [Clontech] was cleaved with XbaI and PacI. The desired fragments (1.3 kb for MN 20-19 and 5.5 kb for pBacPAK8) were isolated by agarose gel electrophoresis, recovered using Gene Clean II, and co-precipitated at an insert:vector ratio of 2.4:1.

After ligation with T4 DNA ligase, the DNA was used to transform competent NM522 *E. coli* cells (Stratagene). Plasmid mini-preps from resultant ampicillin resistant colonies were screened for the presence of the correct insert by restriction mapping. Plasmid DNA from an appropriate colony and linearized BacPAK6 baculovirus DNA [Clontech] were used to transform Sf9 cells by standard techniques. Recombination produced BacPAK viruses carrying the MN 20-19 sequence. Those viruses were plated onto Sf9 cells and overlaid with agar.

Plaques were picked and plated onto Sf9 cells. The conditioned media and cells were collected. A small aliquot of the conditioned media was set aside for testing. The cells were extracted with PBS with 1% Triton X100.

The conditioned media and the cell extracts were dot blotted onto nitrocellulose paper. The blot was blocked with 5% non-fat dried milk in PBS. Mab M75 were used to detect the MN 20-19 protein in the dot blots. A rabbit anti-mouse Ig-HRP was used to detect bound Mab M75. The blots were developed with TMB/$H_2O_2$ with a membrane enhancer [KPL; Gaithersburg, Md. (USA)]. Two clones producing the strongest reaction on the dot blots were selected for expansion. One was used to produce MN 20-19 protein in High Five cells [Invitrogen Corp., San Diego, Calif. (USA); BTI-TN-5BI-4; derived from *Trichoplusia ni* egg cell homogenate]. MN 20-19 protein was purified from the conditioned media from the virus infected High Five cells.

The MN 20-19 protein was purified from the conditioned media by immunoaffinity chromatography. 6.5 mg of Mab M75 was coupled to 1 g of Tresyl activated Toyopearl™ [solid support in bead form; Tosoh, Japan (#14471)]. Approximately 150 ml of the conditioned media was run through the M75-Toyopearl column. The column was washed with PBS, and the MN 20-19 protein was eluted with 1.5 M MgCl. The eluted protein was then dialyzed against PBS.

Synthetic and Biologic Production of MN Proteins and Polypeptides

MN proteins and polypeptides of this invention may be prepared not only by recombinant means but also by synthetic and by other biologic means. Synthetic formation of the polypeptide or protein requires chemically synthesizing the desired chain of amino acids by methods well known in the art. Exemplary of other biologic means to prepare the desired polypeptide or protein is to subject to selective proteolysis a longer MN polypeptide or protein containing the desired amino acid sequence; for example, the longer polypeptide or protein can be split with chemical reagents or with enzymes.

Chemical synthesis of a peptide is conventional in the art and can be accomplished, for example, by the Merrifield solid phase synthesis technique [Merrifield, J., *Am. Chem. Soc.*, 85: 2149-2154 (1963); Kent et al., *Synthetic Peptides in Biology and Medicine*, 29 f.f. eds. Alitalo et al., (Elsevier Science Publishers 1985); and Haug, J. D., "Peptide Synthesis and Protecting Group Strategy", *American Biotechnology Laboratory*, 5(1): 40-47 (January/February 1987)].

Techniques of chemical peptide synthesis include using automatic peptide synthesizers employing commercially available protected amino acids, for example, Biosearch [San Rafael, Calif. (USA)] Models 9500 and 9600; Applied Biosystems, Inc. [Foster City, Calif. (USA)] Model 430; Milligen [a division of Millipore Corp.; Bedford, Mass. (USA)] Model 9050; and Du Pont's RAMP (Rapid Automated Multiple Peptide Synthesis) [Du Pont Compass, Wilmington, Del. (USA)].

Regulation of MN Expression and MN Promoter

MN appears to be a novel regulatory protein that is directly involved in the control of cell proliferation and in cellular transformation. In HeLa cells, the expression of MN is positively regulated by cell density. Its level is increased by persistent infection with LCMV. In hybrid cells between HeLa and normal fibroblasts, MN expression correlates with tumorigenicity. The fact that MN is not present in nontumorigenic hybrid cells (CGL1), but is expressed in a tumorigenic segregant lacking chromosome 11, indicates that MN is negatively regulated by a putative suppressor in chromosome 11.

Evidence supporting the regulatory role of MN protein was found in the generation of stable transfectants of NIH 3T3 cells that constitutively express MN protein as described in Example 15. As a consequence of MN expression, the NIH 3T3 cells acquired features associated with a transformed phenotype: altered morphology, increased saturation density, proliferative advantage in serum-reduced media, enhanced DNA synthesis and capacity for anchorage-independent growth. Further, as shown in Example 16, flow cytometric analyses of asynchronous cell populations indicated that the expression of MN protein leads to accelerated progression of cells through G1 phase, reduction of cell size and the loss of capacity for growth arrest under inappropriate conditions. Also, Example 16 shows that MN expressing cells display a decreased sensitivity to the DNA damaging drug-mitomycin C.

Nontumorigenic human cells, CGL1 cells, were also transfected with the full-length MN cDNA. The same pSG5C-MN construct in combination with pSV2neo plasmid as used to transfect the NIH 3T3 cells (Example 15) was used. Also the protocol was the same except that the G418 concentration was increased to 1000 µg/ml.

Out of 15 MN-positive clones (tested by SP-RIA and Western blotting), 3 were chosen for further analysis. Two MN-negative clones isolated from CGL1 cells transfected with empty plasmid were added as controls. Initial analysis indicates that the morphology and growth habits of MN-transfected CGL1 cells are not changed dramatically, but their proliferation rate and plating efficiency is increased.

MN cDNA and promoter. When the promoter region from the MN genomic clone, isolated as described above, was linked to MN cDNA and transfected into CGL1 hybrid cells, expression of MN protein was detectable immediately after selection. However, then it gradually ceased, indicating thus an action of a feedback regulator. The putative regulatory element appeared to be acting via the MN promoter, because when the full-length cDNA (not containing the promoter) was used for transfection, no similar effect was observed.

An "antisense" MN cDNA/MN promoter construct was used to transfect CGL3 cells. The effect was the opposite of that of the CGL1 cells transfected with the "sense" construct. Whereas the transfected CGL1 cells formed colonies several times larger than the control CGL1, the transfected CGL3 cells formed colonies much smaller than the control CGL3 cells.

For those experiments, the part of the promoter region that was linked to the MN cDNA through BamHI site was derived from NcoI-BamHI fragment of the MN genomic clone and represents the region 233 bp upstream from the transcription initiation site. After the ligation, the joint DNA was inserted into a pBK-CMV expression vector [Stratagene]. The required orientation of the inserted sequence was ensured by directional cloning and subsequently verified by restriction analysis. The tranfection procedure was the same as used in transfecting the NIH 3T3 cells (Example 15), but co-transfection with the pSV2neo plasmid was not necessary since the neo selection marker was already included in the pBK-CMV vector.

After two weeks of selection in a medium containing G418, remarkable differences between the numbers and sizes of the colonies grown were evident as noted above. Immediately following the selection and cloning, the MN-transfected CGL1 and CGL3 cells were tested by SP-RIA for expression and repression of MN, respectively. The isolated transfected CGL1 clones were MN positive (although the level was lower than obtained with the full-length cDNA), whereas MN protein was almost absent from the transfected CGL3 clones. However, in subsequent passages, the expression of MN in transfected CGL1 cells started to cease, and was then blocked perhaps evidencing a control feedback mechanism.

As a result of the very much lowered proliferation of the transfected CGL3 cells, it was difficult to expand the majority of cloned cells (according to SP-RIA, those with the lowest levels of MN), and they were lost during passaging. However, some clones overcame that problem and again expressed MN. It is possible that once those cells reached a higher quantity, that the level of endogenously produced MN mRNA increased over the amount of ectopically expressed antisense mRNA.

Nucleic Acid Probes and Test Kits

Nucleic acid probes of this invention are those comprising sequences that are complementary or substantially complementary to the MN cDNA sequences shown in FIGS. 1A-1B and 15 or to other MN gene sequences, such as, the genomic clone sequence of FIG. 25 [SEQ. ID. NO.: 23]. The phrase "substantially complementary" is defined herein to have the meaning as it is well understood in the art and, thus, used in the context of standard hybridization conditions. The stringency of hybridization conditions can be adjusted to control the precision of complementarity. Exemplary are the stringent hybridization conditions used in Examples 11 and 12. Two nucleic acids are, for example, substantially complementary to each other, if they hybridize to each other under such stringent hybridization conditions.

Stringent hybridization conditions are considered herein to conform to standard hybridization conditions understood in the art to be stringent. For example, it is generally understood that stringent conditions encompass relatively low salt and/or high temperature conditions, such as provided by 0.02 M to 0.15 M NaCl at temperatures of 50° C. to 70° C. Less stringent conditions, such as, 0.15 M to 0.9 M salt at temperatures ranging from 20° C. to 55° C. can be made more stringent by adding increasing amounts of formamide, which serves to destabilize hybrid duplexes as does increased temperature.

Exemplary stringent hybridization conditions are described in Examples 11 and 12, infra; the hybridizations therein were carried out "in the presence of 50% formamide at 42° C." [See Sambrook et al., *Molecular Cloning: A Laboratory Manual*, pages 1.91 and 9.47-9.51 (Second Edition, Cold Spring Harbor Laboratory Press; Cold Spring Harbor, N.Y.; 1989); Maniatis et al., *Molecular Cloning: A Laboratory Manual*, pages 387-389 (Cold Spring Harbor Laboratory; Cold Spring Harbor, N.Y.; 1982); Tsuchiya et al., *Oral Surgery, Oral Medicine, Oral Pathology*, 71(6): 721-725 (June 1991).]

Preferred nucleic acid probes of this invention are fragments of the isolated nucleic acid sequences that encode MN proteins or polypeptides according to this invention. Preferably those probes are composed of at least fifty nucleotides.

However, nucleic acid probes of this invention need not hybridize to a coding region of MN. For example, nucleic acid probes of this invention may hybridize partially or wholly to a non-coding region of the genomic clone of FIG. 25a-b [SEQ. ID. NO.: 23]. Conventional technology can be used to determine whether fragments of SEQ. ID. NO.: 23 or related nucleic acids are useful to identify MN nucleic acid sequences. [See, for example, Benton and Davis, supra and Fuscoe et al., supra.]

Nucleic acid probes of this invention can be used to detect MN DNA and/or RNA, and thus can be used to test for the presence or absence of MN genes, and amplification(s), mutation(s) or genetic rearrangements of MN genes in the cells of a patient. For example, overexpression of an MN gene may be detected by Northern blotting using probes of this invention. Gene alterations, as amplifications, translocations, inversions, and deletions among others, can be detected by using probes of this invention for in situ hybridization to chromosomes from a patient's cells, whether in metaphase spreads or interphase nuclei. Southern blotting could also be used with the probes of this invention to detect amplifications or deletions of MN genes. Restriction Fragment Length Polymorphism (RFLP) analysis using said probes is a preferred method of detecting gene alterations, mutations and deletions. Said probes can also be used to identify MN proteins and/or polypeptides as well as homologs or near homologs thereto by their hybridization to various mRNAs transcribed from MN genes in different tissues.

Probes of this invention thus can be useful diagnostically/prognostically. Said probes can be embodied in test kits, preferably with appropriate means to enable said probes when hybridized to an appropriate MN gene or MN mRNA target to be visualized. Such samples include tissue specimens including smears, body fluids and tissue and cell extracts.

PCR Assays. To detect relatively large genetic rearrangements, hybridization tests can be used. To detect relatively small genetic rearrangements, as, for example, small deletions or amplifications, or point mutations, the polymerase chain reaction (PCR) would preferably be used. [U.S. Pat. Nos. 4,800,159; 4,683,195; 4,683,202; and Chapter 14 of Sambrook et al., *Molecular Cloning: A Laboratory Manual*, supra]

An exemplary assay would use cellular DNA from normal and cancerous cells, which DNA would be isolated and amplified employing appropriate PCR primers. The PCR products would be compared, preferably initially, on a sizing gel to detect size changes indicative of certain genetic rearrangements. If no differences in sizes are noted, further comparisons can be made, preferably using, for example, PCR-single-strand conformation polymorphism (PCR-SSCP) assay or a denaturing gradient gel electrophoretic assay. [See, for example, Hayashi, K., "PCR-SSCP: A Simple and Sensitive Method for Detection of Mutations in the Genomic DNA," in *PCR Methods and Applications*, 1: 34-38 (1991); and Meyers et al., "Detection and Localization of Single Base Changes by Denaturing Gradient Gel Electrophoresis," *Methods in Enzymology*, 155: 501 (1987).]

Assays

Assays according to this invention are provided to detect and/or quantitate MN antigen or MN-specific antibodies in vertebrate samples, preferably mammalian samples, more preferably human samples. Such samples include tissue specimens, body fluids, tissue extracts and cell extracts. MN antigen may be detected by immunoassay, immunohistochemical staining, immunoelectron and scanning microscopy using immunogold among other techniques.

Preferred tissue specimens to assay by immunohistochemical staining include cell smears, histological sections from biopsied tissues or organs, and imprint preparations among other tissue samples. Such tissue specimens can be variously maintained, for example, they can be fresh, frozen, or formalin-, alcohol- or acetone- or otherwise fixed and/or paraffin-embedded and deparaffinized. Biopsied tissue samples can be, for example, those samples removed by aspiration, bite, brush, cone, chorionic villus, endoscopic, excisional, incisional, needle, percutaneous punch, and surface biopsies, among other biopsy techniques.

Preferred cervical tissue specimens include cervical smears, conization specimens, histologic sections from hysterectomy specimens or other biopsied cervical tissue samples. Preferred means of obtaining cervical smears include routine swab, scraping or cytobrush techniques, among other means. More preferred are cytobrush or swab techniques. Preferably, cell smears are made on microscope slides, fixed, for example, with 55% EtOH or an alcohol based spray fixative and air-dried.

Papanicolaou-stained cervical smears (Pap smears) can be screened by the methods of this invention, for example, for retrospective studies. Preferably, Pap smears would be decolorized and re-stained with labeled antibodies against MN antigen. Also archival specimens, for example, matched smears and biopsy and/or tumor specimens, can be used for retrospective studies. Prospective studies can also be done with matched specimens from patients that have a higher than normal risk of exhibiting abnormal cervical cytopathology.

Preferred samples in which to assay MN antigen by, for example, Western blotting or radioimmunoassay, are tissue and/or cell extracts. However, MN antigen may be detected in body fluids, which can include among other fluids: blood, serum, plasma, semen, breast exudate, saliva, tears, sputum, mucous, urine, lymph, cytosols, ascites, pleural effusions, amniotic fluid, bladder washes, bronchioalveolar lavages and cerebrospinal fluid. It is preferred that the MN antigen be concentrated from a larger volume of body fluid before testing. Preferred body fluids to assay would depend on the type of cancer for which one was testing, but in general preferred body fluids would be breast exudate, pleural effusions and ascites.

MN-specific antibodies can be bound by serologically active MN proteins/polypeptides in samples of such body fluids as blood, plasma, serum, lymph, mucous, tears, urine, spinal fluid and saliva; however, such antibodies are found most usually in blood, plasma and serum, preferably in serum. A representative assay to detect MN-specific antibodies is shown in Example 8 below wherein the fusion protein GEX-3X-MN is used. Correlation of the results from the assays to detect and/or quantitate MN antigen and MN-specific antibodies reactive therewith, provides a preferred profile of the disease condition of a patient.

The assays of this invention are both diagnostic and/or prognostic, i.e., diagnostic/prognostic. The term "diagnostic/prognostic" is herein defined to encompass the following processes either individually or cumulatively depending upon the clinical context: determining the presence of disease, determining the nature of a disease, distinguishing one disease from another, forecasting as to the probable outcome of a disease state, determining the prospect as to recovery from a disease as indicated by the nature and symptoms of a case, monitoring the disease status of a patient, monitoring a patient for recurrence of disease, and/or determining the preferred therapeutic regimen for a patient. The diagnostic/prognostic methods of this invention are useful, for example, for screening populations for the presence of neoplastic or preneoplastic disease, determining the risk of developing neoplastic disease, diagnosing the presence of neoplastic and/or pre-neoplastic disease, monitoring the disease status of patients with neoplastic disease, and/or determining the prognosis for the course of neoplastic disease. For example, it appears that the intensity of the immunostaining with MN-specific antibodies may correlate with the severity of dysplasia present in samples tested.

The present invention is useful for screening for the presence of a wide variety of neoplastic diseases including carcinomas, such as, mammary, urinary tract, ovarian, uterine, cervical, endometrial, squamous cell and adenosquamous carcinomas; head and neck cancers; mesodermal tumors, such as, neuroblastomas and retinoblastomas; sarcomas, such as osteosarcomas and Ewing's sarcoma; and melanomas. Of particular interest are gynecological cancers including ovarian, uterine, cervical, vaginal, vulval and endometrial cancers, particularly ovarian, uterine cervical and endometrial cancers. Also of particular interest are cancers of the breast, of the stomach including esophagus, of the colon, of the kidney, of the prostate, of the liver, of the urinary tract including bladder, of the lung, and of the head and neck.

The invention provides methods and compositions for evaluating the probability of the presence of malignant or pre-malignant cells, for example, in a group of cells freshly removed from a host. Such an assay can be used to detect tumors, quantitate their growth, and help in the diagnosis and prognosis of disease. The assays can also be used to detect the presence of cancer metastasis, as well as confirm the absence or removal of all tumor tissue following surgery, cancer chemotherapy and/or radiation therapy. It can further be used to monitor cancer chemotherapy and tumor reappearance.

The presence of MN antigen or antibodies can be detected and/or quantitated using a number of well-defined diagnostic assays. Those in the art can adapt any of the conventional immunoassay formats to detect and/or quantitate MN antigen and/or antibodies. Example 8 details the format of a preferred diagnostic method of this invention—a radioimmunoassay. Immunohistochemical staining is another preferred assay format as exemplified in Example 13.

Many other formats for detection of MN antigen and MN-specific antibodies are, of course available. Those can be Western blots, ELISAs (enzyme-linked immunosorbent assays), RIAs (radioimmunoassay), competitive EIA or dual antibody sandwich assays, among other assays all commonly used in the diagnostic industry. In such immunoassays, the interpretation of the results is based on the assumption that the antibody or antibody combination will not cross-react with other proteins and protein fragments present in the sample that are unrelated to MN.

Representative of one type of ELISA test for MN antigen is a format wherein a microtiter plate is coated with antibodies made to MN proteins/polypeptides or antibodies made to whole cells expressing MN proteins, and to this is added a patient sample, for example, a tissue or cell extract. After a period of incubation permitting any antigen to bind to the antibodies, the plate is washed and another set of anti-MN antibodies which are linked to an enzyme is added, incubated to allow reaction to take place, and the plate is then rewashed. Thereafter, enzyme substrate is added to the microtiter plate and incubated for a period of time to allow the enzyme to work on the substrate, and the absorbance of the final preparation is measured. A large change in absorbance indicates a positive result.

It is also apparent to one skilled in the art of immunoassays that MN proteins and/or polypeptides can be used to detect and/or quantitate the presence of MN antigen in the body fluids, tissues and/or cells of patients. In one such embodiment, a competition immunoassay is used, wherein the MN protein/polypeptide is labeled and a body fluid is added to compete the binding of the labeled MN protein/polypeptide to antibodies specific to MN protein/polypeptide. Such an assay can be used to detect and/or quantitate MN antigen as described in Example 8.

In another embodiment, an immunometric assay may be used wherein a labeled antibody made to a MN protein or polypeptide is used. In such an assay, the amount of labeled antibody which complexes with the antigen-bound antibody is directly proportional to the amount of MN antigen in the sample.

A representative assay to detect MN-specific antibodies is a competition assay in which labeled MN protein/polypeptide is precipitated by antibodies in a sample, for example, in combination with monoclonal antibodies recognizing MN proteins/polypeptides. One skilled in the art could adapt any of the conventional immunoassay formats to detect and/or quantitate MN-specific antibodies. Detection of the binding of said antibodies to said MN protein/polypeptide could be by many ways known to those in the art, e.g., in humans, with the use of anti-human labeled IgG.

An exemplary immunoassay method of this invention to detect and/or quantitate MN antigen in a vertebrate sample comprises the steps of:

a) incubating said vertebrate sample with one or more sets of antibodies (an antibody or antibodies) that bind to MN antigen wherein one set is labeled or otherwise detectable;

b) examining the incubated sample for the presence of immune complexes comprising MN antigen and said antibodies.

Another exemplary immunoassay method according to this invention is that wherein a competition immunoassay is used to detect and/or quantitate MN antigen in a vertebrate sample and wherein said method comprises the steps of:

a) incubating a vertebrate sample with one or more sets of MN-specific antibodies and a certain amount of a labeled or otherwise detectable MN protein/polypeptide wherein said MN protein/polypeptide competes for binding to said antibodies with MN antigen present in the sample;

b) examining the incubated sample to determine the amount of labeled/detectable MN protein/polypeptide bound to said antibodies; and c) determining from the results of the examination in step b) whether MN antigen is present in said sample and/or the amount of MN antigen present in said sample.

Once antibodies (including biologically active antibody fragments) having suitable specificity have been prepared, a wide variety of immunological assay methods are available for determining the formation of specific antibody-antigen complexes. Numerous competitive and non-competitive protein binding assays have been described in the scientific and patent literature, and a large number of such assays are commercially available. Exemplary immunoassays which are suitable for detecting a serum antigen include those described in U.S. Pat. Nos. 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876.

Antibodies employed in assays may be labeled or unlabeled. Unlabeled antibodies may be employed in agglutination; labeled antibodies may be employed in a wide variety of assays, employing a wide variety of labels.

Suitable detection means include the use of labels such as radionuclides, enzymes, coenzymes, fluorescers, chemiluminescers, chromogens, enzyme substrates or co-factors, enzyme inhibitors, free radicals, particles, dyes and the like. Such labeled reagents may be used in a variety of well known assays, such as radioimmunoassays, enzyme immunoassays, e.g., ELISA, fluorescent immunoassays, and the like. See for example, U.S. Pat. Nos. 3,766,162; 3,791,932; 3,817,837; and 4,233,402.

Methods to prepare antibodies useful in the assays of the invention are described below. The examples below detail representative assays according to this invention.

Immunoassay Test Kits

The above outlined assays can be embodied in test kits to detect and/or quantitate MN antigen and/or MN-specific antibodies (including biologically active antibody fragments). Kits to detect and/or quantitate MN antigen can comprise MN protein(s)/polypeptides(s) and/or MN-specific antibodies, polyclonal and/or monoclonal. Such diagnostic/prognostic test kits can comprise one or more sets of antibodies, polyclonal and/or monoclonal, for a sandwich format wherein antibodies recognize epitopes on the MN antigen, and one set is appropriately labeled or is otherwise detectable.

Test kits for an assay format wherein there is competition between a labeled (or otherwise detectable) MN protein/polypeptide and MN antigen in the sample, for binding to an antibody, can comprise the combination of the labeled protein/polypeptide and the antibody in amounts which provide for optimum sensitivity and accuracy.

Test kits for MN-specific antibodies preferably comprise labeled/detectable MN proteins(s) and/or polypeptides(s), and may comprise other components as necessary, for example, to perform a preferred assay as outlined in Example 8 below, such as, controls, buffers, diluents and detergents. Such test kits can have other appropriate formats for conventional assays.

A kit for use in an enzyme-immunoassay typically includes an enzyme-labelled reagent and a substrate for the enzyme. The enzyme can, for example, bind either an MN-specific antibody of this invention or to an antibody to such an MN-specific antibody.

Preparation of MN-Specific Antibodies

The term "antibodies" is defined herein to include not only whole antibodies but also biologically active fragments of antibodies, preferably fragments containing the antigen binding regions. Such antibodies may be prepared by conventional methodology and/or by genetic engineering. Antibody fragments may be genetically engineered, preferably from the variable regions of the light and/or heavy chains ($V_H$ and $V_L$), including the hypervariable regions, and still more preferably from both the $V_H$ and $V_L$ regions. For example, the term "antibodies" as used herein comprehends polyclonal and monoclonal antibodies and biologically active fragments thereof including among other possibilities "univalent" antibodies [Glennie et al., Nature, 295: 712 (1982)]; Fab proteins including Fab' and F(ab')$_2$ fragments whether covalently or non-covalently aggregated; light or heavy chains alone, preferably variable heavy and light chain regions ($V_H$ and $V_L$ regions), and more preferably including the hypervariable regions [otherwise known as the complementarity determining regions (CDRs) of said $V_H$ and $V_L$ regions]; $F_c$ proteins; "hybrid" antibodies capable of binding more than one antigen; constant-variable region chimeras; "composite" immunoglobulins with heavy and light chains of different origins; "altered" antibodies with improved specificity and other characteristics as prepared by standard recombinant techniques and also by oligonucleotide-directed mutagenesis techniques [Dalbadie-McFarland et al., PNAS (USA), 79: 6409 (1982)].

It may be preferred for therapeutic and/or imaging uses that the antibodies be biologically active antibody fragments, preferably genetically engineered fragments, more preferably genetically engineered fragments from the $V_H$ and/or $V_L$ regions, and still more preferably comprising the hypervariable regions thereof.

There are conventional techniques for making polyclonal and monoclonal antibodies well-known in the immunoassay art. Immunogens to prepare MN-specific antibodies include MN proteins and/or polypeptides, preferably purified, and MX-infected tumor line cells, for example, MX-infected HeLa cells, among other immunogens.

Anti-peptide antibodies are also made by conventional methods in the art as described in European Patent Publication No. 44,710 (published Jan. 27, 1982). Briefly, such anti-peptide antibodies are prepared by selecting a peptide from an MN amino acid sequence as from FIG. 1A-B or 15, chemically synthesizing it, conjugating it to an appropriate immunogenic protein and injecting it into an appropriate animal, usually a rabbit or a mouse; then, either polyclonal or monoclonal antibodies are made, the latter by a Kohler-Milstein procedure, for example.

Besides conventional hybridoma technology, newer technologies can be used to produce antibodies according to this invention. For example, the use of the PCR to clone and express antibody V-genes and phage display technology to select antibody genes encoding fragments with binding activities has resulted in the isolation of antibody fragments from repertoires of PCR amplified V-genes using immunized mice or humans. [Marks et al., BioTechnology, 10: 779 (July 1992) for references; Chiang et al., BioTechniques, 7(4): 360 (1989); Ward et al., Nature, 341: 544 (Oct. 12, 1989); Marks et al., J. Mol. Biol., 222: 581 (1991); Clackson et al., Nature, 352: (15 Aug. 1991); and Mullinax et al., PNAS (USA), 87: 8095 (October 1990).]

Descriptions of preparing antibodies, which term is herein defined to include biologically active antibody fragments, by recombinant techniques can be found in U.S. Pat. No. 4,816,567 (issued Mar. 28, 1989); European Patent Application Publication Number (EP) 338,745 (published Oct. 25, 1989); EP 368,684 (published Jun. 16, 1990); EP 239,400 (published Sep. 30, 1987); WO 90/14424 (published Nov. 29, 1990); WO 90/14430 (published May 16, 1990); Huse et al., Science, 246: 1275 (Dec. 8, 1989); Marks et al., BioTechnology, 10: 779 (July 1992); La Sastry et al., PNAS (USA), 86: 5728 (August 1989); Chiang et al., BioTechniques, 7(40): 360 (1989); Orlandi et al., PNAS (USA), 86: 3833 (May 1989); Ward et al. Nature, 341: 544 (Oct. 12, 1989); Marks et al., J. Mol. Biol., 222: 581 (1991); and Hoogenboom et al., Nucleic Acids Res., 19(15): 4133 (1991).

Representative Mabs

Monoclonal antibodies for use in the assays of this invention may be obtained by methods well known in the art for example, Galfre and Milstein, "Preparation of Monoclonal Antibodies: Strategies and Procedures," in Methods in Enzymology: Immunochemical Techniques. 73: 1-46 [Langone and Vanatis (eds); Academic Press (1981)]; and in the classic reference, Milstein and Kohler, Nature, 256: 495-497 (1975).]

Although representative hybridomas of this invention are formed by the fusion of murine cell lines, human/human hybridomas [Olsson et al., PNAS (USA), 77: 5429 (1980)] and human/murine hybridomas [Schlom et al., PNAS (USA), 77: 6841 (1980); Shearman et al. J. Immunol., 146: 928-935

(1991); and Gorman et al., *PNAS* (USA), 88: 4181-4185 (1991)] can also be prepared among other possibilities. Such humanized monoclonal antibodies would be preferred monoclonal antibodies for therapeutic and imaging uses.

Monoclonal antibodies specific for this invention can be prepared by immunizing appropriate mammals, preferably rodents, more preferably rabbits or mice, with an appropriate immunogen, for example, MaTu-infected HeLa cells, MN fusion proteins, or MN proteins/polypeptides attached to a carrier protein if necessary. Exemplary methods of producing antibodies of this invention are described below.

The monoclonal antibodies useful according to this invention to identify MN proteins/polypeptides can be labeled in any conventional manner, for example, with enzymes such as horseradish peroxidase (HRP), fluorescent compounds, or with radioactive isotopes such as, $^{125}$I, among other labels. A preferred label, according to this invention is $^{125}$I, and a preferred method of labeling the antibodies is by using chloramine-T [Hunter, W. M., "Radioimmunoassay," In: *Handbook of Experimental Immunology*, pp. 14.1-14.40 (D. W. Weir ed.; Blackwell, Oxford/London/Edinburgh/Melbourne; 1978)].

Representative mabs of this invention include Mabs M75, MN9, MN12 and MN7 described below. Monoclonal antibodies of this invention serve to identify MN proteins/polypeptides in various laboratory diagnostic tests, for example, in tumor cell cultures or in clinical samples.

Mabs Prepared Against HeLa Cells

MAb M75. Monoclonal antibody M75 (MAb M75) is produced by mouse lymphocytic hybridoma VU-M75, which was initially deposited in the Collection of Hybridomas at the Institute of Virology, Slovak Academy of Sciences (Bratislava, Slovakia) and was deposited under ATCC Designation HB 11128 on Sep. 17, 1992 at the American Type Culture Collection (ATCC) in Manassas, Va. (USA).

Hybridoma VU-M75 was produced according to the procedure described in Gerhard, W., "Fusion of cells in suspension and outgrowth of hybrids in conditioned medium," In: *Monoclonal Antibodies. Hybridomas: A New Dimension in Biological Analysis*, page 370 [Kennet et al. (eds.); Plenum N.Y. (USA)]. BALB/C mice were immunized with MaTu-infected HeLa cells, and their spleen cells were fused with myeloma cell line NS-0. Tissue culture media from the hybridomas were screened for monoclonal antibodies, using as antigen the p58 immunoprecipitated from cell extracts of MaTu-infected HeLa with rabbit anti-MaTu serum and protein A-*Staphylococcus aureus* cells (SAC) [Zavada and Zavadova, *Arch. Virol.*, 118 189-197 (1991)], and eluted from SDS-PAGE gels. Monoclonal antibodies were purified from TC media by affinity chromatography on protein A-Sepharose [Harlow and Lane, "*Antibodies: A Laboratory Manual*," Cold Spring Harbor, Cold Spring Harbor, N.Y. (USA); 1988].

Mab M75 recognizes both the nonglycosylated GEX-3X-MN fusion protein and native MN protein as expressed in CGL3 cells equally well. Mab M75 was shown by epitope mapping to be reactive with the epitope represented by the amino acid sequence from AA 62 to AA 67 [SEQ. ID. NO.: 10] of the MN protein shown in FIG. 15.

Mabs M16 and M67. Also produced by the method described for producing MAb M75 (isotype IgG2B) were MAbs M16 (isotype IgG2A) and M67 (isotype IgG1). Mabs M16 and M67 recognize MX protein, as described in the examples below.

MAb H460. Monoclonal antibody H460 (MAb H460) was prepared in a manner similar to that for MAb M75 except that the mice were immunized with HeLa cells uninfected with MaTu, and lymphocytes of the mice rather than spleen cells were fused with cells from myeloma cell line NS-0. MAb H460 reacts about equally with any human cells.

Mabs Prepared Against Fusion Protein GEX-3X-MN

Monoclonal antibodies of this invention were also prepared against the MN glutathione S-transferase fusion protein (GEX-3X-MN) purified by affinity chromatography as described above. BALB/C mice were immunized intraperitoneally according to standard procedures with the GEX-3X-MN fusion protein in Freund's adjuvant. Spleen cells of the mice were fused with SP/20 myeloma cells [Milstein and Kohler, supra].

Tissue culture media from the hybridomas were screened against CGL3 and CGL1 membrane extracts in an ELISA employing HRP labelled-rabbit anti-mouse. The membrane extracts were coated onto microtiter plates. Selected were antibodies reacted with the CGL3 membrane extract. Selected hybridomas were cloned twice by limiting dilution.

The mabs prepared by the just described method were characterized by Western blots of the GEX-3X-MN fusion protein, and with membrane extracts from the CGL1 and CGL3 cells. Representative of the mabs prepared are Mabs MN9, MN12 and MN7.

Mab MN9. Monoclonal antibody MN9 (Mab MN9) reacts to the same epitope as Mab M75, represented by the sequence from AA 62 to AA 67 [SEQ. ID. NO.: 10] of the FIG. 15 MN protein. As Mab M75, Mab MN9 recognizes both the GEX-3X-MN fusion protein and native MN protein equally well.

Mabs corresponding to Mab MN9 can be prepared reproducibly by screening a series of mabs prepared against an MN protein/polypeptide, such as, the GEX-3X-MN fusion protein, against the peptide representing the epitope for Mabs M75 and MN9. That peptide is Arg Arg Ile Cys Pro Val [SEQ. ID. NO.: 10]. Alternatively, the Novatope system [Novagen] or competition with the deposited Mab M75 could be used to select mabs comparable to Mabs M75 and MN9.

Mab MN12. Monoclonal antibody MN12 (Mab MN12) is produced by the mouse lymphocytic hybridoma MN 12.2.2 which was deposited under ATCC Designation HB 11647 on Jun. 9, 1994 at the American Type Culture Collection (ATCC) at 10801 University Blvd., Manassas, Va. 20110-2209 (USA). Antibodies corresponding to Mab MN12 can also be made, analogously to the method outlined above for Mab MN9, by screening a series of antibodies prepared against an MN protein/polypeptide, against the peptide representing the epitope for Mab MN12. That peptide is Gly Lys Met Thr His Trp (SEQ. ID. NO.: 11). The Novatope system could also be used to find antibodies specific for said epitope.

Mab MN7. Monoclonal antibody MN7 (Mab MN7) was selected from mabs prepared against nonglycosylated GEX-3X-MN as described above. It recognizes the epitope on MN represented by the amino acid sequence from AA 127 to AA 147 [SEQ. ID. NO.: 12; Asn Asn Ala H is Arg Asp Lys Glu Gly Asp Asp Gln Ser His Trp Arg Tyr Gly Gly Asp Pro] of the FIG. 15 MN protein. Analogously to methods described above for Mabs MN9 and MN12, mabs corresponding to Mab MN7 can be prepared by selecting mabs prepared against an MN protein/polypeptide that are reactive with the peptide having SEQ. ID. NO.: 12, or by the stated alternative means.

Epitope Mapping

Epitope mapping was performed by the Novatope system, a kit for which is commercially available from Novagen, Inc. [See, for analogous example, Li et al., *Nature*, 363: 85-88 (6 May 1993).] In brief, the MN cDNA was cut into overlapping short fragments of approximately 60 base pairs. The fragments were expressed in *E. coli*, and the *E. coli* colonies were transferred onto nitrocellulose paper, lysed and probed with the mab of interest. The MN cDNA of clones reactive with the mab of interest was sequenced, and the epitopes of the mabs were deduced from the overlapping polypeptides found to be reactive with each mab.

Therapeutic Use of MN-Specific Antibodies

The MN-specific antibodies of this invention, monoclonal and/or polyclonal, preferably monoclonal, and as outlined above, may be used therapeutically in the treatment of neoplastic and/or pre-neoplastic disease, either alone or in combination with chemotherapeutic drugs or toxic agents, such as ricin A. Further preferred for therapeutic use would be biologically active antibody fragments as described herein. Also preferred MN-specific antibodies for such therapeutic uses would be humanized monoclonal antibodies.

The MN-specific antibodies can be administered in a therapeutically effective amount, preferably dispersed in a physiologically acceptable, nontoxic liquid vehicle.

Imaging Use of Antibodies

Further, the MN-specific antibodies of this invention when linked to an imaging agent, such as a radionuclide, can be used for imaging. Biologically active antibody fragments or humanized monoclonal antibodies, may be preferred for imaging use.

A patient's neoplastic tissue can be identified as, for example, sites of transformed stem cells, of tumors and locations of any metastases. Antibodies, appropriately labeled or linked to an imaging agent, can be injected in a physiologically acceptable carrier into a patient, and the binding of the antibodies can be detected by a method appropriate to the label or imaging agent, for example, by scintigraphy.

Antisense MN Nucleic Acid Sequences

MN genes are herein considered putative oncogenes and the encoded proteins thereby are considered to be putative oncoproteins. Antisense nucleic acid sequences substantially complementary to mRNA transcribed from MN genes, as represented by the antisense oligodeoxynucleotides (ODNs) of Example 10, infra, can be used to reduce or prevent expression of the MN gene. [Zamecnik, P. C., "Introduction: Oligonucleotide Base Hybridization as a Modulator of Genetic Message Readout," pp. 1-6, *Prospects for Antisense Nucleic Acid Therapy of Cancer and AIDS*, (Wiley-Liss, Inc., New York, N.Y., USA; 1991); Wickstrom, E., "Antisense DNA Treatment of HL-60 Promyelocytic Leukemia Cells: Terminal Differentiation and Dependence on Target Sequence," pp. 7-24, id.; Leserman et al., "Targeting and Intracellular Delivery of Antisense Oligonucleotides Interfering with Oncogene Expression," pp. 25-34, id.; Yokoyama, K., "Transcriptional Regulation of c-myc Proto-oncogene by Antisense RNA," pp. 35-52, id.; van den Berg et al., "Antisense fos Oligodeoxyribonucleotides Suppress the Generation of Chromosomal Aberrations," pp. 63-70, id.; Mercola, D., "Antisense fos and fun RNA," pp. 83-114, id.; Inouye, *Gene*, 72: 25-34 (1988); Miller and Ts'o, *Ann. Reports Med. Chem.*, 23: 295-304 (1988); Stein and Cohen, *Cancer Res.*, 48: 2659-2668 (1988); Stevenson and Inversen, *J. Gen. Virol.*, 70: 2673-2682 (1989); Goodchild, "Inhibition of Gene Expression by Oligonucleotides," pp. 53-77, *Oligodeoxynucleotides: Antisense Inhibitors of Gene Expression* (Cohen, J. S., ed; CRC Press, Boca Raton, Fla., USA; 1989); Dervan et al., "Oligonucleotide Recognition of Double-helical DNA by Triple-helix Formation," pp. 197-210, id.; Neckers, L. M., "Antisense Oligodeoxynucleotides as a Tool for Studying Cell Regulation: Mechanisms of Uptake and Application to the Study of Oncogene Function," pp. 211-232, id.; Leitner et al., *PNAS* (USA), 87: 3430-3434 (1990); Bevilacqua et al., *PNAS* (USA), 85: 831-835 (1988); Loke et al. *Curr. Top. Microbiol. Immunol.*, 141: 282-288 (1988); Sarin et al., *PNAS* (USA), 85: 7448-7451 (1988); Agrawal et al., "Antisense Oligonucleotides: A Possible Approach for Chemotherapy and AIDS," International Union of Biochemistry Conference on Nucleic Acid Therapeutics (Jan. 13-17, 1991; Clearwater Beach, Fla., USA); Armstrong, L., *Ber. Week*, pp. 88-89 (Mar. 5, 1990); and Weintraub et al., *Trends*, 1: 22-25 (1985).] Such antisense nucleic acid sequences, preferably oligonucleotides, by hybridizing to the MN mRNA, particularly in the vicinity of the ribosome binding site and translation initiation point, inhibits translation of the mRNA. Thus, the use of such antisense nucleic acid sequences may be considered to be a form of cancer therapy.

Preferred antisense oligonucleotides according to this invention are gene-specific ODNs or oligonucleotides complementary to the 5' end of MN mRNA. Particularly preferred are the 29-mer ODN1 and 19-mer ODN2 for which the sequences are provided in Example 10, infra. Those antisense ODNs are representative of the many antisense nucleic acid sequences that can function to inhibit MN gene expression. Ones of ordinary skill in the art could determine appropriate antisense nucleic acid sequences, preferably antisense oligonucleotides, from the nucleic acid sequences of FIGS. 1A-1B, 15 and 25a-b.

Also, as described above, CGL3 cells transfected with an "antisense" MN cDNA/promoter construct formed colonies much smaller than control CGL3 cells.

Vaccines

It will be readily appreciated that MN proteins and polypeptides of this invention can be incorporated into vaccines capable of inducing protective immunity against neoplastic disease and a dampening effect upon tumorigenic activity. Efficacy of a representative MN fusion protein GEX-3X-MN as a vaccine in a rat model is shown in Example 14.

MN proteins and/or polypeptides may be synthesized or prepared recombinantly or otherwise biologically, to comprise one or more amino acid sequences corresponding to one or more epitopes of the MN proteins either in monomeric or multimeric form. Those proteins and/or polypeptides may then be incorporated into vaccines capable of inducing protective immunity. Techniques for enhancing the antigenicity of such polypeptides include incorporation into a multimeric structure, binding to a highly immunogenic protein carrier, for example, keyhole limpet hemocyanin (KLH), or diphtheria toxoid, and administration in combination with adjuvants or any other enhancers of immune response.

Preferred MN proteins/polypeptides to be used in a vaccine according to this invention would be genetically engineered MN proteins. Preferred recombinant MN protein are the GEX-3X-MN and MN 20-19 proteins.

A preferred exemplary use of such a vaccine of this invention would be its administration to patients whose MN-carrying-primary cancer had been surgically removed. The vaccine may induce active immunity in the patients and prevent recidivism or metastasis.

It will further be appreciated that anti-idiotype antibodies to antibodies to MN proteins/polypeptides are also useful as vaccines and can be similarly formulated.

An amino acid sequence corresponding to an epitope of an MN protein/polypeptide either in monomeric or multimeric form may also be obtained by chemical synthetic means or by purification from biological sources including genetically modified microorganisms or their culture media. [See Lerner, "Synthetic Vaccines", *Sci. Am.* 248(2): 66-74 (1983).] The protein/polypeptide may be combined in an amino acid sequence with other proteins/polypeptides including fragments of other proteins, as for example, when synthesized as a fusion protein, or linked to other antigenic or non-antigenic polypeptides of synthetic or biological origin. In some instances, it may be desirable to fuse a MN protein or polypeptide to an immunogenic and/or antigenic protein or polypeptide, for example, to stimulate efficacy of a MN-based vaccine.

The term "corresponding to an epitope of an MN protein/polypeptide" will be understood to include the practical possibility that, in some instances, amino acid sequence variations of a naturally occurring protein or polypeptide may be antigenic and confer protective immunity against neoplastic disease and/or anti-tumorigenic effects. Possible sequence variations include, without limitation, amino acid substitutions, extensions, deletions, truncations, interpolations and combinations thereof. Such variations fall within the contemplated scope of the invention provided the protein or polypeptide containing them is immunogenic and antibodies elicited by such a polypeptide or protein cross-react with naturally occurring MN proteins and polypeptides to a sufficient extent to provide protective immunity and/or anti-tumorigenic activity when administered as a vaccine.

Such vaccine compositions will be combined with a physiologically acceptable medium, including immunologically acceptable diluents and carriers as well as commonly employed adjuvants such as Freund's Complete Adjuvant, saponin, alum, and the like. Administration would be in immunologically effective amounts of the MN proteins or polypeptides, preferably in quantities providing unit doses of from 0.01 to 10.0 micrograms of immunologically active MN protein and/or polypeptide per kilogram of the recipient's body weight. Total protective doses may range from 0.1 to about 100 micrograms of antigen.

Routes of administration, antigen dose, number and frequency of injections are all matters of optimization within the scope of the ordinary skill in the art.

The following examples are for purposes of illustration only and not meant to limit the invention in any way.

Materials and Methods

The following materials and methods were used in examples below.

MaTu-Infected and Uninfected HeLa Cells

MaTu agent [Zavada et al., *Nature New Biol.,* 240: 124-125 (1972); Zavada et al., *J. Gen. Virol,* 24: 327-337 (1974)] was from original "MaTu" cells [Widmaier et al., *Arch. Geschwulstforsch,* 44: 1-10 (1974)] transferred into our stock of HeLa by cocultivation with MaTu cells treated with mitomycin C, to ensure that control and MaTu-infected cells were comparable. MaTu cells were incubated for 3 hours at 37° C. in media with 5 μg/ml of mitomycin C [Calbiochem; LaJolla, Calif. (USA)]. Mixed cultures were set to $2\times10^5$ of mitomycin C-treated cells and $4\times10^5$ of fresh recipient cells in 5 ml of medium. After 3 days they were first subcultured and further passaged 1-2 times weekly.

Control HeLa cells were the same as those described in Zavada et al. (1972), supra.

Sera

Human sera from cancer patients, from patients suffering with various non-tumor complaints and from healthy women were obtained from the Clinics of Obstetrics and Gynaecology at the Postgraduate Medical School, Bratislava, Slovakia. Human serum KH was from a fifty year old mammary carcinoma patient, fourteen months after resection. That serum was one of two sera out of 401 serum samples that contained neutralizing antibodies to the VSV(MaTU) pseudotype as described in Zavada et al. (1972), supra. Serum L8 was from a patient with Paget's disease. Serum M7 was from a healthy donor.

Rabbit anti-MaTu serum was prepared by immunizing a rabbit three times at intervals of 30 days with 1-$5\times10^7$ viable MaTu-infected HeLa cells.

RIP and PAGE

RIP and PAGE were performed essentially as described in Zavada and Zavadova, supra, except that in the experiments described herein [$^{35}$S]methionine (NEN), 10 μCi/ml of methionine-free MEM medium, supplemented with 2% FCS and 3% complete MEM were used. Confluent petri dish cultures of cells were incubated overnight in that media.

For RIP, the SAC procedure [Kessler, *J. Immunol.,* 115: 1617-1624 (1975)] was used. All incubations and centrifugations were performed at 0-4° C. Cell monolayers were extracted with RIPA buffer (0.14 M NaCl, 7.5 mM phosphate buffer, pH 7.2, 1% Triton X-100, 0.1% sodium deoxycholate, 1 mM phenylmethylsulfonyl fluoride and Trasylol). To reduce non-specific reactions, antisera were preabsorbed with fetal calf serum [Barbacid et al., *PNAS* (USA), 77: 1617-1621 (1980)] and antigenic extracts with SAC.

For PAGE (under reducing conditions) we used 10% gels with SDS [Laemmli, *Nature,* 227: 680-685 (1970)]. As reference marker proteins served the Sigma kit [product MW-SDS-200; St. Louis, Mo. (USA)]. For fluorography we used salicylate [Heegaard et al., *Electrophoresis,* 5: 263-269 (1984)].

Immunoblots

Immunoblotting used as described herein follows the method of Towbin et al., *PNAS* (USA), 76: 4350-4354 (1979). The proteins were transferred from the gels onto nitrocellulose [Schleicher and Schuell; Dassel Germany; 0.45 μm porosity] in Laemmli electrode buffer diluted 1:10 with distilled water, with no methanol or SDS. The transfer was for 2½ hours at 1.75 mA/cm$^2$. The blots were developed with $^{125}$I-labeled MAbs and autoradiography was performed using intensifying screens, with X-ray films exposed at −70° C.

In extracts from cell cultures containing only small amounts of MN antigen, we concentrated the antigen from 0.5 or 1 ml of an extract by adding 50 μl of a 10% SAC suspension, pre-loaded with MAb M75. This method allowed the concentration of MN antigen even from clinical specimens, containing human IgG; preliminary control experiments showed that such a method did not interfere with the binding of the MN antigen to SAC-adsorbed M75. Tissue extracts were made by grinding the tissue with a mortar and pestle and sand (analytical grade). To the homogenates was added RIPA buffer, 10:1 (volume to weight) of original tissue. The extracts were clarified for 3 minutes on an Eppendorf centrifuge.

Example 1

Immunofluorescence of MaTu-Specific Antigens

Immunofluorescence experiments were performed on control and MaTu-infected HeLa cells with monoclonal antibodies, prepared as described above, which are specific for MaTu-related antigens. FITC-conjugated anti-mouse IgG was used to detect the presence of the monoclonal antibodies. Staining of the cells with Giemsa revealed no clear differences between control and MaTu-infected HeLa cells.

MAbs, which in preliminary tests proved to be specific for MaTu-related antigens, showed two different reactivities in immunofluorescence. A representative of the first group, MAb M67, gave a granular cytoplasmic fluorescence in MaTu-infected HeLa, which was only seen in cells fixed with acetone; living cells showed no fluorescence. MAb M16 gave the same type of fluorescence. With either M67 or M16, only extremely weak "background" fluorescence was seen in control HeLa cells.

Another MAb, M75, showed a granular membrane fluorescence on living MaTu-infected cells and a granular nuclear fluorescence in acetone-fixed cells. However, M75 sometimes showed a similar, although much weaker, fluorescence on uninfected HeLa cells. A relationship was observed based upon the conditions of growth: in HeLa cells uninfected with MaTu, both types of fluorescence with MAb M75 were observed only if the cells were grown for several passages in dense cultures, but not in sparse ones.

The amount of M75-reactive cell surface antigen was analyzed cytofluorometrically and was dependent on the density of the cell cultures and on infection with MaTu. Control and MaTu infected HeLa cells were grown for 12 days in dense or sparse cultures. The cells were released with Versene (EDTA), and incubated with MAb M75 or with no MAb, and subsequently incubated with FITC-conjugated anti-mouse IgG. The intensity of fluorescence was measured.

It appeared that the antigen binding MAb M75 is inducible: it was found to be absent in control HeLa grown in sparse culture, and to be induced either by the growth of HeLa in dense culture or by infection with MaTu. Those two factors were found to have an additive or synergistic effect. Those observations indicated along with other results described herein that there were two different agents involved: exogenous, transmissible MX, reactive with M67, and endogenous, inducible MN, detected by MAb M75.

Example 2

Immunoblot Analysis of Protein(s) Reactive with MAb M75

To determine whether MAb M75 reacts with the same protein in both uninfected and MaTu-infected HeLa, and to determine the molecular weight of the protein, extracts of those cells were analyzed by PAGE and immunoblotting (as described above). HeLa cells uninfected or MaTu-infected, that had been grown for 12 days in dense or sparse cultures, were seeded in 5-cm petri dishes, all variants at $5 \times 10^5$ cells per dish. Two days later, the cells were extracted with RIPA buffer (above described), 200 µl/dish. The extracts were mixed with 2× concentrated Laemmli sample buffer containing 6% mercaptoethanol and boiled for five minutes. Proteins were separated by SDS-PAGE and blotted on nitrocellulose. The blots were developed with $^{125}$I-labeled MAb M75 and autoradiography.

MAb M75 reacted with two MN-specific protein bands of 54 kd and 58 kd, which were the same in uninfected HeLa grown at high density and in MaTu-infected HeLa, evidencing that M75 recognizes the same protein(s) in both uninfected and MaTu-infected HeLa cells. Consistent with the cytofluorometric results, the amount of the antigen depended both on cell density and on infection with MaTu, the latter being a much more potent inducer of p54/58N.

Example 3

Radioimmunoassay of MaTu-Specific Antigens In Situ

In contrast to the results with M75, the other MAb, M67, appeared to be specific for the exogenous, transmissible agent MX. With M67 we observed no immunofluorescence in control HeLa, regardless of whether the cells were grown in dense or in sparse culture. That difference was clearly evidenced in radioimmunoassay experiments wherein $^{125}$I-labeled MAbs M67 and M75 were used.

For such experiments, parallel cultures of uninfected and MaTu-infected cells were grown in dense or sparse cultures. The cultures were either live (without fixation), or fixed (with methanol for five minutes and air-dried). The cultures were incubated for two hours in petri dishes with the $^{125}$I-labeled MAbs, $6 \times 10^4$ cpm/dish. Afterward, the cultures were rinsed four times with PBS and solubilized with 1 ml/dish of 2 N NaOH, and the radioactivity was determined on a gamma counter.

The simple radioimmunoassay procedure of this example was performed directly in petri dish cultures. Sixteen variants of the radioimmunoassay enabled us to determine whether the MX and MN antigens are located on the surface or in the interior of the cells and how the expression of those two antigens depends on infection with MaTu and on the density, in which the cells had been grown before the petri dishes were seeded. In live, unfixed cells only cell surface antigens can bind the MAbs. In those cells, M67 showed no reaction with any variant of the cultures, whereas M75 reacted in accord with the results of Examples 1 and 2 above.

Fixation of the cells with methanol made the cell membrane permeable to the MAbs: M67 reacted with HeLa infected with MaTu, independently of previous cell density, and it did not bind to control HeLa. MAb M75 in methanol-fixed cells confirmed the absence of corresponding antigen in uninfected HeLa from sparse cultures and its induction both by growth in dense cultures and by infection with MaTu.

Example 4

Identification of MaTu Components Reactive with Animal Sera or Associated with VSV Virions Immunoblot analyses of MaTu-specific proteins from RIPA extracts from uninfected or MaTu-infected HeLa and from purified VSV reproduced in control or in MaTu-infected HeLa, identified which of the antigens, p58X or p54/58N, were radioimmunoprecipitated with animal sera, and which of them was responsible for complementation of VSV mutants and for the formation of pseudotype virions. Details concerning the procedures can be found in Pastorekova et al., *Virology,* 187: 620-626 (1992).

The serum of a rabbit immunized with MaTu-infected HeLa immunoprecipitated both MAb M67- and MAb M75-reactive proteins (both p58X and p54/58N), whereas the "spontaneously" immune sera of normal rabbit, sheep or leukemic cow immunoprecipitated only the M67-reactive protein (p58X). On the other hand, in VSV reproduced in MaTu-infected HeLa cells and subsequently purified, only the M75-reactive bands of p54/58N were present. Thus, it was concluded that MX and MN are independent components of MaTu, and that it was p54/58N that complemented VSV mutants and was assembled into pseudotype virions.

As shown in FIG. 6 discussed below in Example 5, MX antigen was found to be present in MaTu-infected fibroblasts. In Zavada and Zavadova, supra, it was reported that a p58 band from MX-infected fibroblasts could not be detected by RIP with rabbit anti-MaTu serum. That serum contains more antibodies to MX than to MN antigen. The discrepancy can be explained by the extremely slow spread of MX in infected cultures. The results reported in Zavada and Zavadova, supra were from fibroblasts tested 6 weeks after infection, whereas the later testing was 4 months after infection. We have found by immunoblots that MX can be first detected in both H/F-N and H/F-T hybrids after 4 weeks, in HeLa cells after six weeks and in fibroblasts only 10 weeks after infection.

Example 5

Expression of MN- and MX-Specific Proteins

FIG. 6 graphically illustrates the expression of MN- and MX-specific proteins in human fibroblasts, in HeLa cells and in H/F-N and H/F-T hybrid cells, and contrasts the expression in MX-infected and uninfected cells. Cells were infected with MX by co-cultivation with mitomycin C-treated MX-infected HeLa. The infected and uninfected cells were grown for three passages in dense cultures. About four months after infection, the infected cells concurrently with uninfected cells were grown in petri dishes to produce dense monolayers.

A radioimmunoassay was performed directly in confluent petri dish (5 cm) culture of cells, fixed with methanol essentially as described in Example 3, supra. The monolayers were fixed with methanol and treated with $^{125}$I-labeled MAbs M67 (specific for exogenous MX antigen) or M75 (specific for endogenous MN antigen) at $6 \times 10^4$ cpm/dish. The bound radioactivity was measured; the results are shown in FIG. 6.

FIG. 6 shows that MX was transmitted to all four cell lines tested, that is, to human embryo fibroblasts, to HeLa and to both H/F-N and H/F-T hybrids; at the same time, all four uninfected counterpart cell lines were MX-negative (top graph of FIG. 6). MN antigens are shown to be present in both MX-infected and uninfected HeLa and H/F-T cells, but not in the fibroblasts (bottom graph of FIG. 6). No MN antigen was found in the control H/F-N, and only a minimum increase over background of MN antigen was found in MaTu infected H/F-N. Thus, it was found that in the hybrids, expression of MN antigen very strongly correlates with tumorigenicity.

Those results were consistent with the results obtained by immunoblotting as shown in FIG. 7. The MN-specific twin protein p54/58N was detected in HeLa cell lines (both our standard type, that is, HeLa K, and in the Stanbridge mutant HeLa, that is, D98/AH.2 shown as HeLa S) and in tumorigenic H/F-T; however, p54/58N was not detected in the fibroblasts nor in the non-tumorigenic H/F-N even upon deliberately long exposure of the film used to detect radioactivity. Infection of the HeLa cells with MX resulted in a strong increase in the concentration of the p54/58N protein(s).

The hybrid cells H/F-N and H/F-T were constructed by Eric J. Stanbridge [Stanbridge et al., *Somatic Cell Genetics*, 7: 699-712 (1981); and Stanbridge et al., *Science*, 215: 252-259 (1982)]. His original hybrid, produced by the fusion of a HeLa cell and a human fibroblast was not tumorigenic in nude mice, although it retained some properties of transformed cells, for example, its growth on soft agar. Rare segregants from the hybrid which have lost chromosome 11 are tumorigenic. The most likely explanation for the tumorigenicity of those segregants is that chromosome 11 contains a suppressor gene (an antioncogene), which blocks the expression of a as yet unknown oncogene. The oncoprotein encoded by that oncogene is critical for the capacity of the H/F hybrids to produce tumors in nude mice. Since the p54/58N protein shows a correlation with the tumorigenicity of H/F hybrids, it is a candidate for that putative oncoprotein.

Example 6

Immunoblots of MN Antigen from Human Tumor Cell Cultures and from Clinical Specimens of Human Tissues The association of MN antigen with tumorigenicity in the H/F hybrid cells as illustrated by Example 5 prompted testing for the presence of MN antigen in other human tumor cell cultures and in clinical specimens. Preliminary experiments indicated that the concentration of MN antigen in the extracts from other human tumor cell cultures was lower than in HeLa; thus, it was realized that long exposure of the autoradiographs would be required. Therefore, the sensitivity of the method was increased by the method indicated under *Materials and Methods: Immunoblotting*, supra, wherein the MN antigen was concentrated by precipitation with MAb M75-loaded SAC.

Figure 8:
FIG. 8 (discussed in Example 6) shows immunoblots of MN proteins in cell culture extracts prepared from the following: (A) MX-infected HeLa cells; (B) human fibroblasts; (C) T24; (D) T47D; (E) SK-Mel 1477; and (F) HeLa cells uninfected with MX. The symbols +ME and O ME indicate that the proteins were separated by PAGE after heating in a sample buffer, with and without 3% mercaptoethanol (ME), respectively.

FIG. 8 shows the immunoblots wherein lane A, a cell culture extract from MX-infected HeLa cells was analysed directly (10 µl per lane) whereas the antigens from the other extracts (lanes B-E) were each concentrated from a 500 µl extract by precipitation with MAb M75 and SAC.

FIG. 8 indicates that two other human carcinoma cell lines contain MN-related proteins—T24 (bladder carcinoma; lane C) and T47D (mammary carcinoma; lane D). Those cells contain proteins which react with MAb M75 that under reducing conditions have molecular weights of 54 kd and 56 kd, and under non-reducing conditions have a molecular weight of about 153 kd. The intensity of those bands is at least ten times lower than that for the p54/58N twin protein from HeLa cells.

An extremely weak band at approximately 52 kd could be seen under reducing conditions from extracts from human melanoma cells (SK-Mel 1477; lane E), but no bands for human fibroblast extracts (lane B) could be seen either on the reducing or non-reducing gels.

Figure 9:
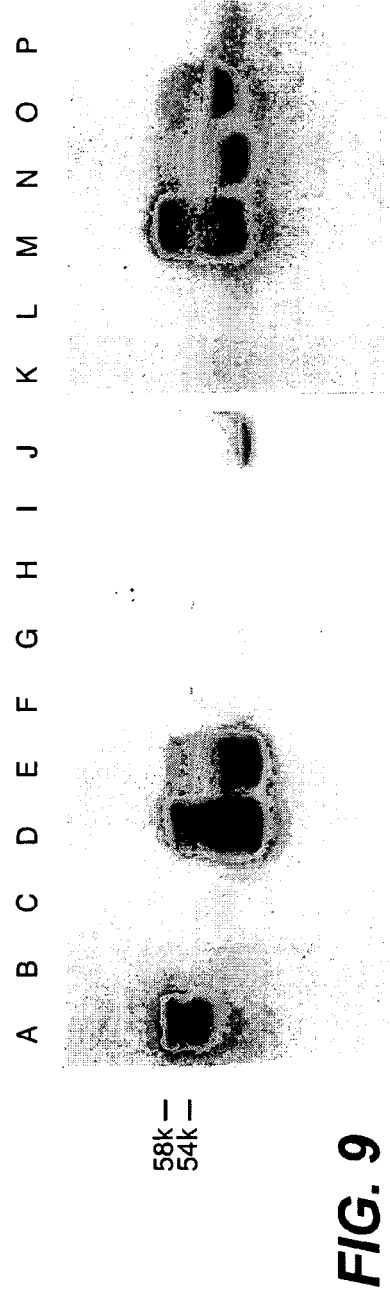
FIG. 9 (discussed in Example 6) provides immunoblots of MN proteins from human tissue extracts. The extracts were prepared from the following: (A) MX-infected HeLa cells; (B) full-term placenta; (C) corpus uteri; (D, M) adenocarcinoma endometrii; (E, N) carcinoma ovarii; (F, G) trophoblasts; (H) normal ovary; (I) myoma uteri; (J) mammary papilloma; (K) normal mammary gland; (L) hyperplastic endometrium; (O) cervical carcinoma; and (P) melanoma.

FIG. 9 shows immunoblots of human tissue extracts including surgical specimens as compared to a cell extract from MX-infected HeLa (lane A). The MN-related antigen from all the extracts but for lane A (analysed directly at 10 µl per lane) was first concentrated from a 1 ml extract as explained above. MN proteins were found in endometrial (lanes D and M), ovarian (lanes E and N) and in uterine cervical (lane 0) carcinomas. In those extracts MN-related proteins were found in three bands having molecular weights between about 48 kd and about 58 kd. Another MN-related protein was present in the tissue extract from a mammary papilloma that protein was seen as a single band at about 48 kd (lane J).

Clearly negative were the extracts from full-term placenta (lane B), normal mammary gland (lane K), hyperplastic endometrium (lane L), normal ovaries (lane H), and from uterine myoma (lane I). Only extremely slightly MN-related bands were seen in extracts from trophoblasts (lanes F and G) and from melanoma (lane P).

The observations that antigen related to p54/58N was expressed in clinical specimens of several types of human carcinomas but not in general in normal tissues of the corresponding organs (exceptions delineated in Example 13) further strengthened the association of MN antigen with tumorigenesis. However, it should be noted that for human tumors, a normal tissue is never really an adequate control in that tumors are believed not to arise from mature, differentiated cells, but rather from some stem cells, capable of division and of differentiation. In body organs, such cells may be quite rare.

Example 7

MN Antigen in Animal Cell Lines

Figure 10:
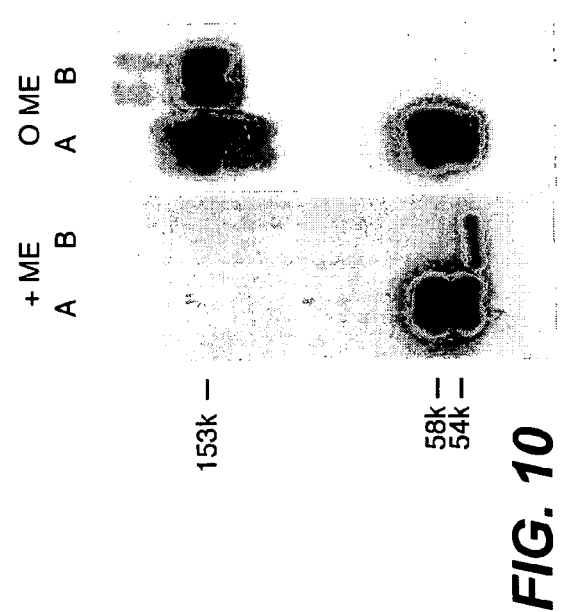
FIG. 10 (discussed in Example 7) provides immunoblots of MN proteins from (A) MX-infected HeLa cells and from (B) Rat2-Tk$^-$ cells. (+ME and 0 ME have the same meanings as explained in the legend to FIG. 8.)

Since the MN gene is present in the chromosomal DNA of all vertebrate species that were tested, MN-related antigen was searched for also in cell lines derived from normal tissues and from tumors of several animal species. MN-related protein was found in two rat cell lines: one of them was the XC cell line derived from rat rhabdomyosarcoma induced with Rous sarcoma virus; the other was the Rat2-Tk⁻ cell line. In extracts from both of those rat cell lines, a single protein band was found on the blots: its molecular weight on blots produced from a reducing gel and from a non-reducing gel was respectively 53.5 kd and 153 kd. FIG. 10 shows the results with Rat2-Tk⁻ cell extracts (lane B), compared with extracts from MX-infected HeLa (lane A); the concentration of MN antigen in those two cell lines is very similar. The extracts were analysed directly (40 µl per lane).

MN-related protein from XC cells showed the same pattern as for Rat2-Tk⁻ cells both under reducing and non-reducing conditions, except that its concentration was about 30× lower. The finding of a MN-related protein—p53.5N—in two rat cell lines (FIGS. 10 and 12) provides the basis for a model system.

None of the other animal cell lines tested contained detectable amounts of MN antigen, even when the highly sensitive immunoblot technique in which the MN antigens are concentrated was used. The MN-negative cells were: Vero cells (African green monkey); mouse L cells; mouse NIH-3T3 cells normal, infected with Moloney leukemia virus, or transformed with Harvey sarcoma virus; GR cells (mouse mammary tumor cells induced with MTV), and NMG cells (normal mouse mammary gland).

Example 8

Radioimmunoassays in Liquid Phase Using Recombinant MN Protein for MN-Specific Antibodies and for MN Antigen The genetically engineered MN protein fused with glutathione S-transferase—GEX-3X-MN—prepared and purified as described above was labeled with $^{125}$I by the chloramine T method [Hunter (1978)]. The purified protein enabled the development of a quantitative RIA for MN-specific antibodies as well as for MN antigens. All dilutions of antibodies and of antigens were prepared in RIPA buffer (1% TRITON X-100 and 0.1% sodium deoxycholate in PBS—phosphate buffered saline, pH 7.2), to which was added 1% of fetal calf serum (FCS). Tissue and cell extracts were prepared in RIPA buffer containing 1 mM phenylmethylsulfonylfluoride and 200 trypsin inhibiting units of Trasylol (aprotinin) per ml, with no FCS. $^{125}$I-labeled GEX-3X-MN protein (2.27 µCi/µg of TCA-precipitable protein) was before use diluted with RIPA+1% FCS, and non-specifically binding radioactivity was adsorbed with a suspension of fixed protein A-*Staphylococcus aureus* cells (SAC).

In an RIA for MN-specific antibodies, MAb-containing ascites fluids or test sera were mixed with 125I-labeled protein and allowed to react in a total volume of 1 ml for 2 hours at room temperature. Subsequently, 50 µl of a 10% suspension of SAC [Kessler, supra] was added and the mixture was incubated for 30 minutes. Finally, the SAC was pelleted, 3× washed with RIPA, and the bound radioactivity was determined on a gamma counter.

Figure 11A:
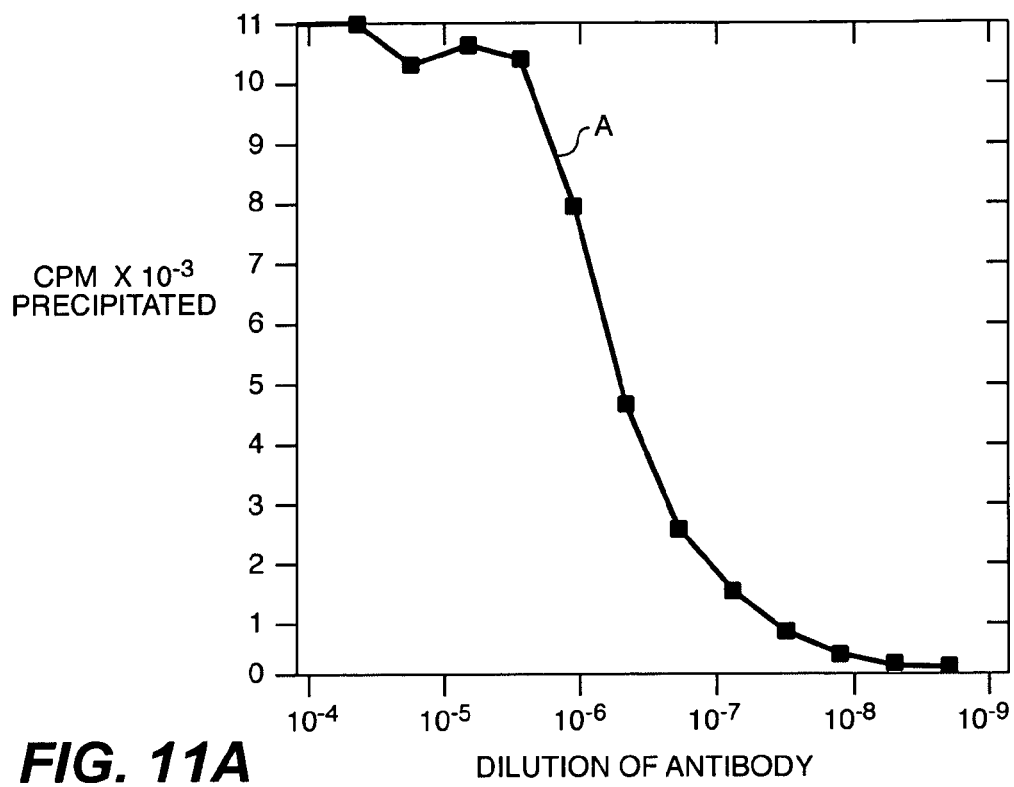
FIG. 11 (discussed in Example 8) graphically illustrates the results from radioimmunoprecipitation experiments with $^{125}$I-GEX-3X-MN protein and different antibodies. The radioactive protein ($15 \times 10^3$ cpm/tube) was precipitated with ascitic fluid or sera and SAC as follows: (A) ascites with MAb M75; (B) rabbit anti-MaTu serum; (C) normal rabbit serum; (D) human serum L8; (E) human serum KH; and (F) human serum M7.
Figure 11B:
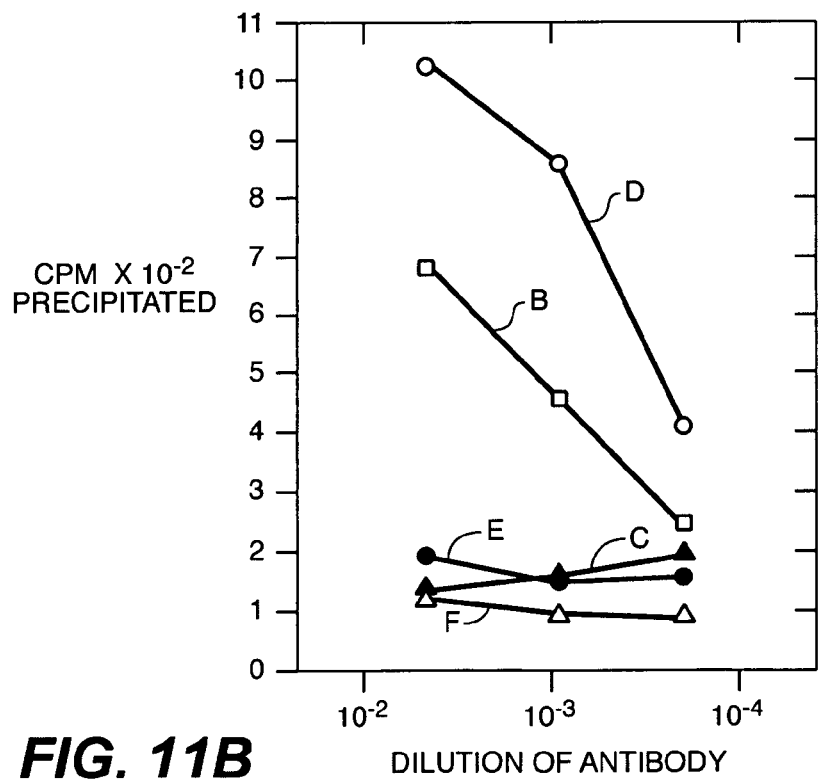

Titration of antibodies to MN antigen is shown in FIG. 11. Ascitic fluid from a mouse carrying M75 hybridoma cells (A) is shown to have a 50% end-point at dilution $1:1.4 \times 10^{-6}$. At the same time, ascitic fluids with MAbs specific for MX protein (M16 and M67) showed no precipitation of $^{125}$I-labeled GEX-3X-MN even at dilution 1:200 (result not shown). Normal rabbit serum (C) did not significantly precipitate the MN antigen; rabbit anti-MaTu serum (B), obtained after immunization with live MX-infected HeLa cells, precipitated 7% of radioactive MN protein, when diluted 1:200. The rabbit anti-MaTu serum is shown by immunoblot in Example 4 (above) to precipitate both MX and MN proteins.

Only one out of 180 human sera tested (90 control and 90 sera of patients with breast, ovarian or uterine cervical cancer) showed a significant precipitation of the radioactively labeled MN recombinant protein. That serum—L8—(D) was retested on immunoblot (as in Example 4), but it did not precipitate any p54/58N from MX-infected HeLa cells. Also, six other human sera, including KH (E), were negative on immunoblot. Thus, the only positive human serum in the RIA, L8, was reactive only with the genetically engineered product, but not with native p54/58N expressed by HeLa cells.

In an RIA for MN antigen, the dilution of MAb M75, which in the previous test precipitated 50% of maximum precipitable radioactivity (=dilution $1:1.4 \times 10^{-6}$) was mixed with dilutions of cell extracts and allowed to react for 2 hours. Then, $^{125}$I-labeled GEX-3X-MN ($25 \times 10^3$ cpm/tube) was added for another 2 hours. Finally, the radioactivity bound to MAb M75 was precipitated with SAC and washed as above. One hundred percent precipitation (=0 inhibition) was considered the maximum radioactivity bound by the dilution of MAb used. The concentration of the MN antigen in the tested cell extracts was calculated from an inhibition curve obtained with "cold" GEX-3X-MN, used as the standard (A in FIG. 12).

The reaction of radioactively labeled GEX-3X-MN protein with MAb M75 enabled us to quantitate MN antigen directly in cell extracts. FIG. 12 shows that 3 ng of "cold" GEX-3X-MN (A) caused a 50% inhibition of precipitation of "hot" GEX-3X-MN; an equivalent amount of MN antigen is present in $3 \times 10^3$ ng of proteins extracted from MaTu-infected HeLa (B) or from Rat2-Tk⁻ cells (C). Concentrations of MN protein in cell extracts, determined by this RIA, are presented in Table 1 below. It must be understood that the calculated values are not absolute, since MN antigens in cell extracts are of somewhat different sizes, and also since the genetically engineered MN protein is a product containing molecules of varying size.

TABLE 1

Concentration of MN Protein in Cell Extracts

| Cells | ng MN/mg total protein |
|---|---|
| HeLa + MX | 939.00 |
| Rat2-Tk⁻ | 1065.00 |
| HeLa | 27.50 |
| XC | 16.40 |
| T24 | 1.18 |
| HEF | 0.00 |

The data were calculated from the results shown in FIG. 12.

Example 9

Immunoelectron and Scanning Microscopy of Control and of MX-Infected HeLa Cells

As indicated above in Example 1, MN antigen, detected by indirect immunofluorescence with MAb M75, is located on the surface membranes and in the nuclei of MX-infected HeLa cells or in HeLa cells grown in dense cultures. To elucidate more clearly the location of the MN antigen, immunoelectron microscopy was used wherein MAb M75 bound to MN antigen was visualized with immunogold beads. [Herzog et al., "Colloidal gold labeling for determining cell surface area," IN: *Colloidal Gold*, Vol. 3 (Hayat, M. A., ed.), pp. 139-149 (Academic Press Inc.; San Diego, Calif.).]

Ultrathin sections of control and of MX-infected HeLa cells are shown in FIG. 13 A-D. Those immunoelectron micrographs demonstrate the location of MN antigen in the cells, and in addition, the striking ultrastructural differences between control and MX-infected HeLa. A control HeLa cell (FIG. 13A) is shown to have on its surface very little MN antigen, as visualised with gold beads. The cell surface is rather smooth, with only two little protrusions. No mitochondria can be seen in the cytoplasm. In contrast, MX-infected HeLa cells (FIGS. 13B and C) show the formation of abundant, dense filamentous protrusions from their surfaces. Most of the MN antigen is located on those filaments, which are decorated with immunogold. The cytoplasm of MX-infected HeLa contains numerous mitochondria (FIG. 13C). FIG. 13D demonstrates the location of MN antigen in the nucleus: some of the MN antigen is in nucleoplasm (possibly linked to chromatin), but a higher concentration of the MN antigen is in the nucleoli. Again, the surface of normal HeLa (panels A and E of FIG. 13) is rather smooth whereas MX-infected HeLa cells have on their surface, numerous filaments and "blebs". Some of the filaments appear to form bridges connecting them to adjacent cells.

Figure 13A:
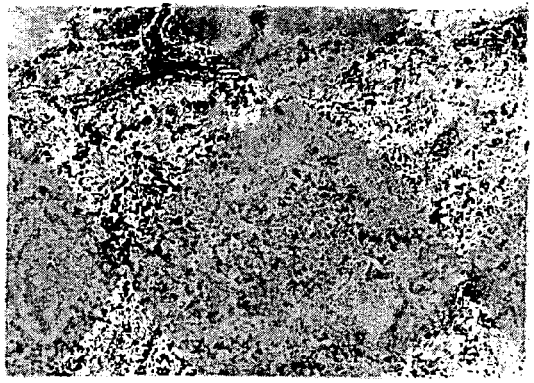
FIG. 13 (discussed in Example 9) provides results of immunoelectron and scanning microscopy of MX-uninfected (control) and MX-infected HeLa cells. Panels A-D show ultrathin sections of cells stained with MAb M75 and immunogold; Panels E and F are scanning electron micrographs of cells wherein no immunogold was used. Panels E and F both show a terminal phase of cell division. Panels A and E are of control HeLa cells; panels B, C, D and F are of MX-infected HeLa cells. The cells shown in Panels A, B and C were fixed and treated with M75 and immunogold before they were embedded and sectioned. Such a procedure allows for immunogold decoration only of cell surface antigens. The cells in Panel D were treated with M75 and immunogold only once they had been embedded and sectioned, and thus antigens inside the cells could also be decorated.
Figure 13B:
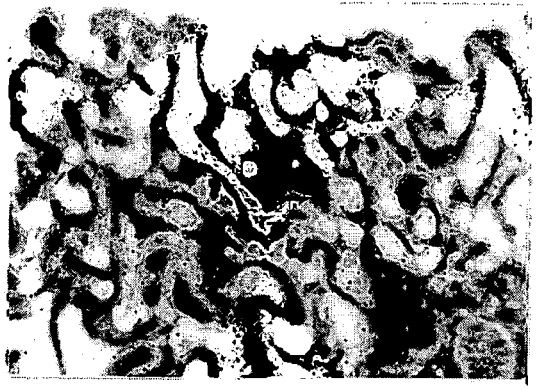
Figure 13C:
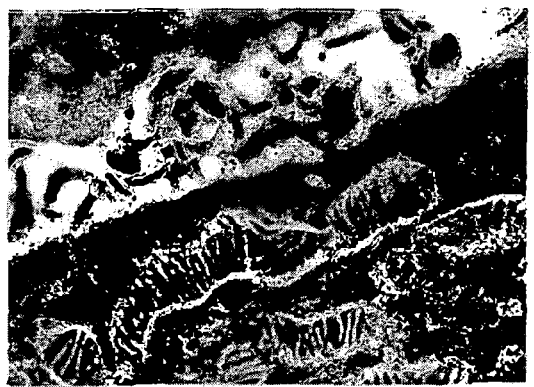
Figure 13D:
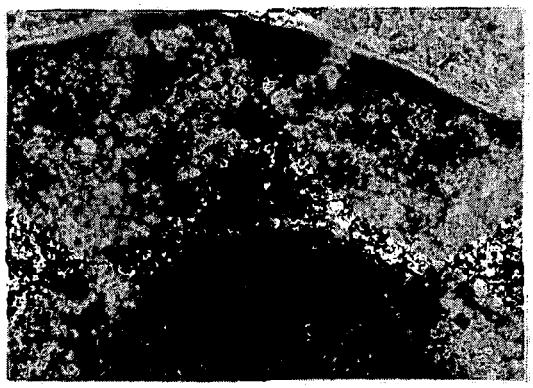
Figure 13E:
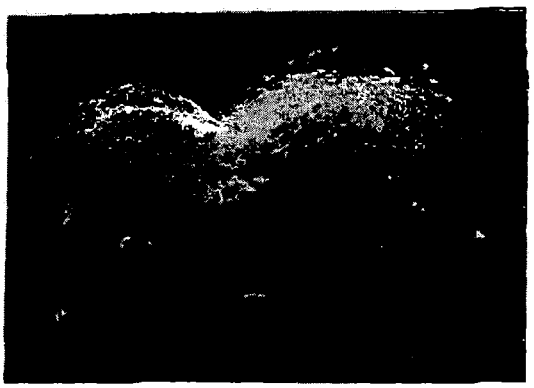
Figure 13F:
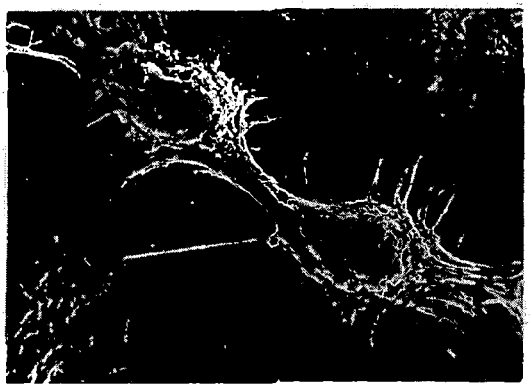

It has been noted that in some instances of in vitro transformed cells compared to their normal parent cells that one of the differences is that the surface of normal cells was smooth whereas on the transformed cells were numerous hair-like protrusions [Darnell et al. "Molecular Cell Biology," (2nd edition) Sci. Am. Books; W.H. Freeman and Co., New York (1990)]. Under that criteria MX-infected HeLa cells, as seen in FIG. 13F, has a supertransformed appearance.

Further in some tumors, amplification of mitochondria has been described [Bernhard, W., "Handbook of Molecular Cytology," pp. 687-715, Lima de Faria (ed.), North Holland Publishing Co.; Amsterdam-London (1972)]. Such amplification was noted for MX-infected HeLa cells which stained very intensely with Janus' green, specific for mitochondria whereas control HeLa were only weakly stained.

It should be noted that electron microscopists were unable to find any structural characteristics specific for tumor cells.

Example 10

Antisense ODNs Inhibit MN Gene Expression

To determine whether both of the p54/58N proteins were encoded by one gene, the following experiments with antisense ODNs were performed. Previously sparse-growing HeLa cells were seeded to obtain an overcrowded culture and incubated for 130 hours either in the absence or in the presence of two gene-specific ODNs complementary to the 5' end of MN mRNA. HeLa cells were subcultured at $8 \times 10^5$ cells per ml of DMEM with 10% FCS. Simultaneously, ODNs were added to the media as follows: (A) 29-mer ODN1 (5' CGC-CCAGTGGGTCATCTTCCCCAGAAGAG 3' [SEQ. ID. NO.: 3], complementary to positions 44-72 of FIG. 1A-1B) in 4 µM final concentration, (B) 19-mer ODN2 (5' GGAATC-CTCCTGCATCCGG 3' [SEQ. ID. NO.: 4], complementary to positions 12-30) in 4 µM final concentration and (C) both ODN1 and ODN2 in 2 µM final concentration each. (D) Cells treated in the same way, but incubated without ODNs, served as a control. After 130 hours, extracts from the cells were prepared and analyzed by immunoblotting using $^{125}$I-labeled MAb M75. Protein extracts from the cells were analyzed by immunoblotting and RIA using MAb M75. FIG. 3 provides the immunoblot results of those experiments.

It was found that cultivation of HeLa cells with the ODNs resulted in considerable inhibition of p54/58N synthesis. The 19-mer ODN2 (FIG. 3B) in 4 µM final concentration was very effective; as determined by RIA, it caused 40% inhibition, whereas the 29-mer ODN1 (4/M) (FIG. 3A) and a combination of the two ODNs (FIG. 3C), each in 2 µm final concentration, were less effective in RIA showing a 25-35% decrease of the MN-related proteins. At the same time, the amount of different HeLa cell protein determined by RIA using specific MAb H460 was in all cell variants approximately the same. Most importantly was that on immunoblot it could be seen that specific inhibition by the ODNs affected both of the p54/58N proteins. Thus, we concluded that the MN gene we cloned coded for both p54/58N proteins in HeLa cells.

The results indicated that the MN twin proteins arise by translation of a single mRNA (consistent with the Northern blotting data). Thus, the twin proteins may represent either differences in post-translational modification (phosphorylation, protease processing, etc.), or the use of alternative translational initiation sites.

Example 11

Northern Blotting of MN mRNA in Tumorigenic and Non-Tumorigenic Cell Lines

Figure 4:
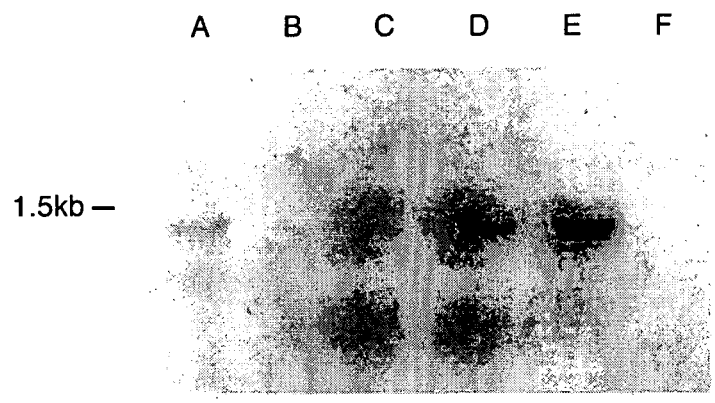
FIG. 4 shows the results of Northern blotting of MN mRNA in human cell lines. Total RNA was prepared from the following cell lines: HeLa cells growing in dense (A) and sparse (B) culture; (C) H/F-N; (D) and (E) H/F-T; and (F) human embryo fibroblasts. Example 11 details the procedure and results.

FIG. 4 shows the results of Northern blotting of MN mRNA in human cell lines. Total RNA was prepared from the following cell lines by the guanidinium thiocyanate-CsCl method: HeLa cells growing in a dense (A) and sparse (B) culture; CGL1 (H/F-N) hybrid cells (C); CGL3 (D) and CGL4 (E) segregants (both H/F-T); and human embryo fibroblasts (F). Fifteen µg of RNA were separated on a 1.2% formaldehyde gel and blotted onto a Hybond C Super membrane [Amersham]. MN cDNA NotI probe was labeled by random priming [Multiprime DNA labelling system; Amersham]. Hybridization was carried out in the presence of 50% formamide at 42° C., and the final wash was in 0.1% SSPE and 0.1% SDS at 65° C. An RNA ladder (0.24-9.5 kb) [BRL; Bethesda, Md. (USA)] was used as a size standard. Membranes were exposed to films at −70° C., with intensifying screens.

Detected was a 1.5 kb MN-specific mRNA only in two tumorigenic segregant clones—CGL3 and CGL4 (H/F-T), but not in the non-tumorigenic hybrid clone CGL1 (H/F-N) or in normal human fibroblasts. Further, the 1.5 kb mRNA was found in the HeLa cells growing in dense (FIG. 4A) but not in sparse (FIG. 4B) culture.

Thus, the results of the Northern blotting were consistent with other examples in regard to MN-related proteins being associated with tumorigenicity.

Example 12

Figure 5:
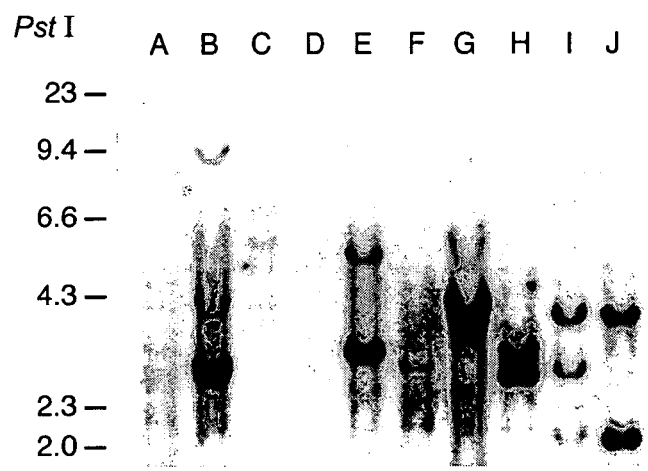
FIG. 5 illustrates the detection of the MN gene in genomic DNAs by Southern blotting. Chromosomal DNA digested by PstI was as follows: (A) chicken; (B) bat; (C) rat; (D) mouse; (E) feline; (F) pig; (G) sheep; (H) bovine; (I) monkey; and (J) human HeLa cells. The procedures used are detailed in Example 12.

Southern Blotting of Genomic DNAs from Different Vertebrate Species to Detect MN Gene and Restriction Analysis of Genomic DNA of HeLa Cells FIG. 5 illustrates the detection of MN genes in the genomic DNAs of various vertebrates by Southern blotting. Chromosomal DNA digested by PstI was as follows: (A) chicken; (B) bat; (C) rat; (D) mouse; (E) feline; (F) pig; (G) sheep; (H) bovine; (I) monkey; and (J) human HeLa cells. Restriction fragments were separated on a 0.7% agarose gel and alkali blotted onto a Hybond N membrane [Amersham]. The MN cDNA probe labelling and hybridization procedures were the same as for the Northern blotting analyses shown in FIG. 4 and described in Example 11. The Southern blot of FIG. 5 made with PstI indicates that the MN gene is conserved in a single copy in all vertebrate genomes tested.

HeLa. Further, genomic DNA from HeLa cells was prepared as described by Ausubel et al., *Short Protocols in Molecular Biology* [Greene Publishing Associates and Wiley-Interscience; New York (1989)], digested with different restriction enzymes, resolved on an agarose gel and transferred to Hybond N+ membrane [Amersham]. The HeLa genomic DNA was cleaved with the following restriction enzymes with the results shown in FIG. 17 (wherein the numbers in parentheses after the enzymes indicate the respective lanes in FIG. 17): EcoRI (1), EcoRV (2), HindIII (3), KpnI (4), NcoI (5), PstI (6), and PvuII (7), and then analyzed by Southern hybridization under stringent conditions using MN cDNA as a probe.

The prehybridization and hybridization using an MN cDNA probe labelled with $^{32}$P-dCTP by random priming [Multiprime DNA labelling system; Amersham] as well as wash steps were carried out according to Amersham's protocols at high stringency. A 1 kb DNA Ladder [from BRL; Bethesda, Md. (USA)] was used as a size standard. Membranes were exposed to films at $-70°$ C., with intensifying screens.

Figure 17:
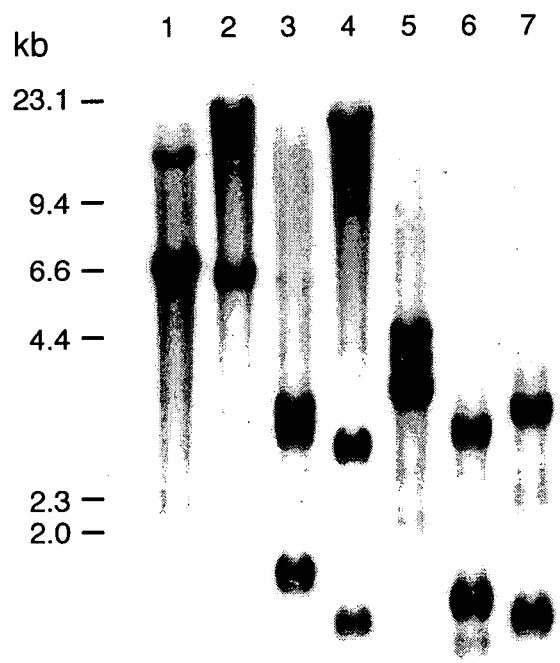
FIG. 17 shows a restriction analysis of the MN gene. Genomic DNA from HeLa cells was cleaved with the following restriction enzymes: EcoRI (1), EcoRV (2), HindIII (3), KpnI (4), NcoI (5), PstI (6), and PvuII (7), and then analyzed by Southern hybridization under stringent conditions using MN cDNA as a probe.
Figure 18:
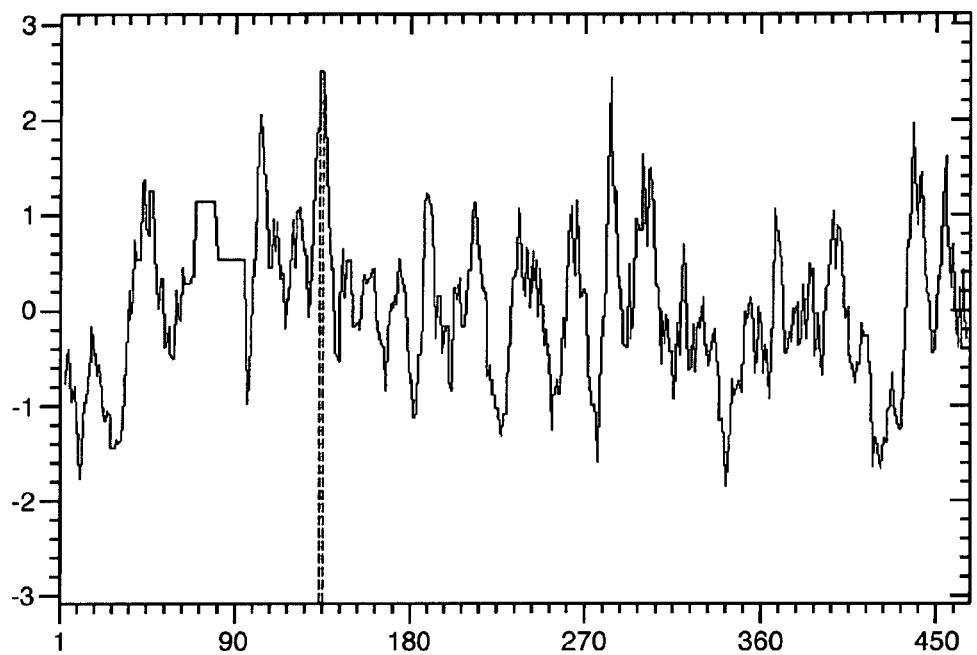
FIG. 18 provides a hydrophilicity profile of the MN protein shown in FIG. 15. The profile was computed using an average group length of 6 amino acids.

The Southern blotting analysis of HeLa chromosomal DNA showed that the gene coding for MN is present in the human genome in a single copy (FIG. 17). The sizes and distribution of MN-positive restriction fragments obtained using the restriction enzymes KpnI, NcoI and HindIII indicate that the MN gene contains introns, since those enzymes cut the MN genomic sequences despite the absence of their restriction sites in MN cDNA.

Example 13

Immunohistochemical Staining of Tissue Specimens

To study and evaluate the tissue distribution range and expression of MN proteins, the monoclonal antibody M75 was used to stain immunohistochemically a variety of human tissue specimens. The primary antibody used in these immunohistochemical staining experiments was the M75 monoclonal antibody. A biotinylated second antibody and streptavidin-peroxidase were used to detect the M75 reactivity in sections of formalin-fixed, paraffin-embedded tissue samples. A commercially available amplification kit, specifically the DAKO LSAB™ kit [DAKO Corp., Carpinteria, Calif. (USA)] which provides matched, ready made blocking reagent, secondary antibody and steptavidin-horseradish peroxidase was used in these experiments.

M75 immunoreactivity was tested according to the methods of this invention in multiple-tissue sections of breast, colon, cervical, lung and normal tissues. Such multiple-tissue sections were cut from paraffin blocks of tissues called "sausages" that were purchased from the City of Hope [Duarte, Calif. (USA)]. Combined in such a multiple-tissue section were normal, benign and malignant specimens of a given tissue; for example, about a score of tissue samples of breast cancers from different patients, a similar number of benign breast tissue samples, and normal breast tissue samples would be combined in one such multiple-breast-tissue section. The normal multiple-tissue sections contained only normal tissues from various organs, for example, liver, spleen, lung, kidney, adrenal gland, brain, prostate, pancreas, thyroid, ovary, and testis.

Also screened for MN gene expression were multiple individual specimens from cervical cancers, bladder cancers, renal cell cancers, and head and neck cancers. Such specimens were obtained from U.C. Davis Medical Center in Sacramento, Calif. and from Dr. Shu Y. Liao [Department of Pathology; St. Joseph Hospital; Orange, Calif. (USA)].

Controls used in these experiments were the cell lines CGL3 (H/F-T hybrid cells) and CGL1 (H/F-N hybrid cells) which are known to stain respectively, positively and negatively with the M75 monoclonal antibody. The M75 monoclonal antibody was diluted to a 1:5000 dilution wherein the diluent was either PBS [0.05 M phosphate buffered saline (0.15 M NaCl), pH 7.2-7.4] or PBS containing 1% protease-free BSA as a protein stabilizer.

Immunohistochemical Staining Protocol

The immunohistochemical staining protocol was followed according to the manufacturer's instructions for the DAKO LSAB™ kit. In brief, the sections were dewaxed, rehydrated and blocked to remove non-specific reactivity as well as endogenous peroxidase activity. Each section was then incubated with dilutions of the M75 monoclonal antibody. After the unbound M75 was removed by rinsing the section, the section was sequentially reacted with a biotinylated anti-mouse IgG antibody and streptavidin conjugated to horseradish peroxidase; a rinsing step was included between those two reactions and after the second reaction. Following the last rinse, the antibody-enzyme complexes were detected by reaction with an insoluble chromogen (diaminobenzidine) and hydrogen peroxide. A positive result was indicated by the formation of an insoluble reddish brown precipitate at the site of the primary antibody reaction. The sections were then rinsed, counterstained with hematoxylin, dehydrated and cover slipped. Then the sections were examined using standard light microscopy. The following is an outline of exemplary steps of the immunohistochemical staining protocol.

| | | |
|---|---|---|
| 1. | Series of ETOH-baths 100, 100, 95, 95, 70% | 2 min. ± 1 min. each |
| 2. | dH$_2$0 wash - 2x | 2 min. ± 1 min. each |
| 3. | 3% H$_2$0$_2$ as endogenous peroxidase block | 5 min. |
| 4. | PBS wash - 2x | 2 min. ± 1 min. |
| 5. | normal serum block (1.5% NGS) | 30 min. |
| 6. | primary antibody (Mab M75) | 60 min. ± 5 min. |
| 7. | PBS wash - 2x | 2 min. ± 1 min. |
| 8. | biotinylated secondary antibody | 20-30 min. ± 2 min. |
| 9. | PBS wash - 2x | 2 min. ± 1 min. |
| 10. | streptavidin-peroxidase reagent | 20-30 min. ± 2 min. |
| 11. | PBS wash - 2x | 2 min. ± 1 min. |
| 12. | DAB (150 ml Tris, 90 µl H$_2$0$_2$, 3 ml KPL DAB) | 5-6 min. |
| 13. | PBS rinse, dH$_2$0 wash | 1-2 min. |
| 14. | Hematoxylin counterstain | 2 min. ± 1 min. |
| 15. | wash with running tap water until clear | |
| 16. | 0.05% ammonium hydroxide | 20 sec. ± 10 sec. |
| 17. | dH$_2$0 wash - 2x | 3 min. ± 1 min. |
| 18. | dehydrate 70, 95, 95, 100, 100% EtOH | 2 min. ± 1 min. each |
| 19. | xylene 3x | 3 min. ± 1 min. each |
| 20. | coverslip with Permount ™ [Fisher Scientific Pittsburgh, PA (USA)] | |
| 21. | wait 10 min. before viewing results. | |

Interpretation. A deposit of a reddish brown precipitate over the plasma membrane was taken as evidence that the M75 antibody had bound to a MN antigen in the tissue. The known positive control (CGL3) had to be stained to validate the assay. Section thickness was taken into consideration to compare staining intensities, as thicker sections produce greater staining intensity independently of other assay parameters.

The above-described protocol was optimized for formalin-fixed tissues, but can be used to stain tissues prepared with other fixatives.

Results

Preliminary examination of cervical specimens showed that 62 of 68 squamous cell carcinoma specimens (91.2%) stained positively with M75. Additionally; 2 of 6 adenocarcinomas and 2 of 2 adenosquamous cancers of the cervix also stained positively. In early studies, 55.6% (10 of 18) of cervical dysplasias stained positively. A total of 9 specimens including both cervical dysplasias and tumors, exhibited some MN expression in normal appearing areas of the endocervical glandular epithelium, usually at the basal layer. In some specimens, whereas morphologically normal-looking areas showed expression of MN antigen, areas exhibiting dysplasia and/or malignancy did not show MN expression.

M75 positive immunoreactivity was most often localized to the plasma membrane of cells, with the most apparent stain being present at the junctions between adjacent cells. Cytoplasmic staining was also evident in some cells; however, plasma membrane staining was most often used as the main criterion of positivity.

M75 positive cells tended to be near areas showing keratin differentiation in cervical specimens. In some specimens, positive staining cells were located in the center of nests of non-staining cells. Often, there was very little, if any, obvious morphological difference between staining cells and non-staining cells. In some specimens, the positive staining cells were associated with adjacent areas of necrosis.

In most of the squamous cell carcinomas of the cervix, the M75 immunoreactivity was focal in distribution, i.e., only certain areas of the specimen stained. Although the distribution of positive reactivity within a given specimen was rather sporadic, the intensity of the reactivity was usually very strong. In most of the adenocarcinomas of the cervix, the staining pattern was more homogeneous, with the majority of the specimen staining positively.

Among the normal tissue samples, intense, positive and specific M75 immunoreactivity was observed only in normal stomach tissues, with diminishing reactivity in the small intestine, appendix and colon. No other normal tissue stained extensively positively for M75. Occasionally, however, foci of intensely staining cells were observed in normal intestine samples (usually at the base of the crypts) or were sometimes seen in morphologically normal appearing areas of the epithelium of cervical specimens exhibiting dysplasia and/or malignancy. In such, normal appearing areas of cervical specimens, positive staining was seen in focal areas of the basal layer of the ectocervical epithelium or in the basal layer of endocervical glandular epithelium. In one normal specimen of human skin, cytoplasmic MN staining was observed in the basal layer. The basal layers of these epithelia are usually areas of proliferation, suggesting the MN expression may be involved in cellular growth. In a few cervical biopsied specimens, MN positivity was observed in the morphologically normal appearing stratified squamous epithelium, sometimes associated with cells undergoing koilocytic changes.

Some colon adenomas (4 of 11) and adenocarcinomas (9 of 15) were positively stained. One normal colon specimen was positive at the base of the crypts. Of 15 colon cancer specimens, 4 adenocarcinomas and 5 metastatic lesions were MN positive. Fewer malignant breast cancers (3 of 25) and ovarian cancer specimens (3 of 15) were positively stained. Of 4 head and neck cancers, 3 stained very intensely with M75.

Although normal stomach tissue was routinely positive, 4 adenocarcinomas of the stomach were MN negative. Of 3 bladder cancer specimens (1 adenocarcinoma, 1 non-papillary transitional cell carcinoma, and 1 squamous cell carcinoma), only the squamous cell carcinoma was MN positive. Approximately 40% (12 of 30) of lung cancer specimens were positive; 2 of 4 undifferentiated carcinomas; 3 of 8 adenocarcinomas; 2 of 8 oat cell carcinomas; and, 5 of 10 squamous cell carcinomas. One hundred percent (4 of 4) of the renal cell carcinomas were MN positive.

In summary, MN antigen, as detected by M75 and immunohistochemistry in the experiments described above, was shown to be prevalent in tumor cells, most notably in tissues of cervical cancers. MN antigen was also found in some cells of normal tissues, and sometimes in morphologically normal appearing areas of specimen exhibiting dysplasia and/or malignancy. However, MN is not usually extensively expressed in most normal tissues, except for stomach tissues where it is extensively expressed and in the tissues of the lower gastrointestinal tract where it is less extensively expressed. MN expression is most often localized to the cellular plasma membrane of tumor cells and may play a role in intercellular communication or cell adhesion. Representative results of experiments performed as described above are tabulated in Table 2.

TABLE 2

Immunoreactivity of M75 in Various Tissues

| TISSUE | TYPE | POS/NEG (#pos/#tested) |
| --- | --- | --- |
| liver, spleen, lung, kidney, adrenal gland, brain, prostate, pancreas, thyroid, ovary, testis | normal | NEG (all) |
| skin | normal | POS (in basal layer) (1/1) |
| stomach | normal | POS |
| small intestine | normal | POS |
| colon | normal | POS |
| breast | normal | NEG (0/10) |
| cervix | normal | NEG (0/2) |
| breast | benign | NEG (0/17) |
| colon | benign | POS (4/11) |
| cervix | benign | POS (10/18) |
| breast | malignant | POS (3/25) |
| colon | malignant | POS (9/15) |
| ovarian | malignant | POS (3/15) |
| lung | malignant | POS (12/30) |
| bladder | malignant | POS (1/3) |
| head & neck | malignant | POS (3/4) |
| kidney | malignant | POS (4/4) |
| stomach | malignant | NEG (0/4) |
| cervix | malignant | POS (62/68) |

The results recorded in this example indicate that the presence of MN proteins in a tissue sample from a patient may, in general, depending upon the tissue involved, be a marker signaling that a pre-neoplastic or neoplastic process is occurring. Thus, one may conclude from these results that diagnostic/prognostic methods that detect MN antigen may be particularly useful for screening patient samples for a number of cancers which can thereby be detected at a pre-neoplastic stage or at an early stage prior to obvious morphologic changes associated with dysplasia and/or malignancy being evident or being evident on a widespread basis.

Example 14

Vaccine

Rat Model

As shown above in Example 7, in some rat tumors, for example, the XC tumor cell line (cells from a rat rhabdomyosarcoma), a rat MN protein, related to human MN, is expressed. Thus a model was afforded to study antitumor immunity induced by experimental MN-based vaccines. The following representative experiments were performed.

Nine- to eleven-day-old Wistar rats from several families were randomized, injected intraperitoneally with 0.1 ml of either control rat sera (the C group) or with rat serum against the MN fusion protein GEX-3X-MN (the IM group). Simultaneously both groups were injected subcutaneously with $10^6$ XC tumor cells.

Figure 14:
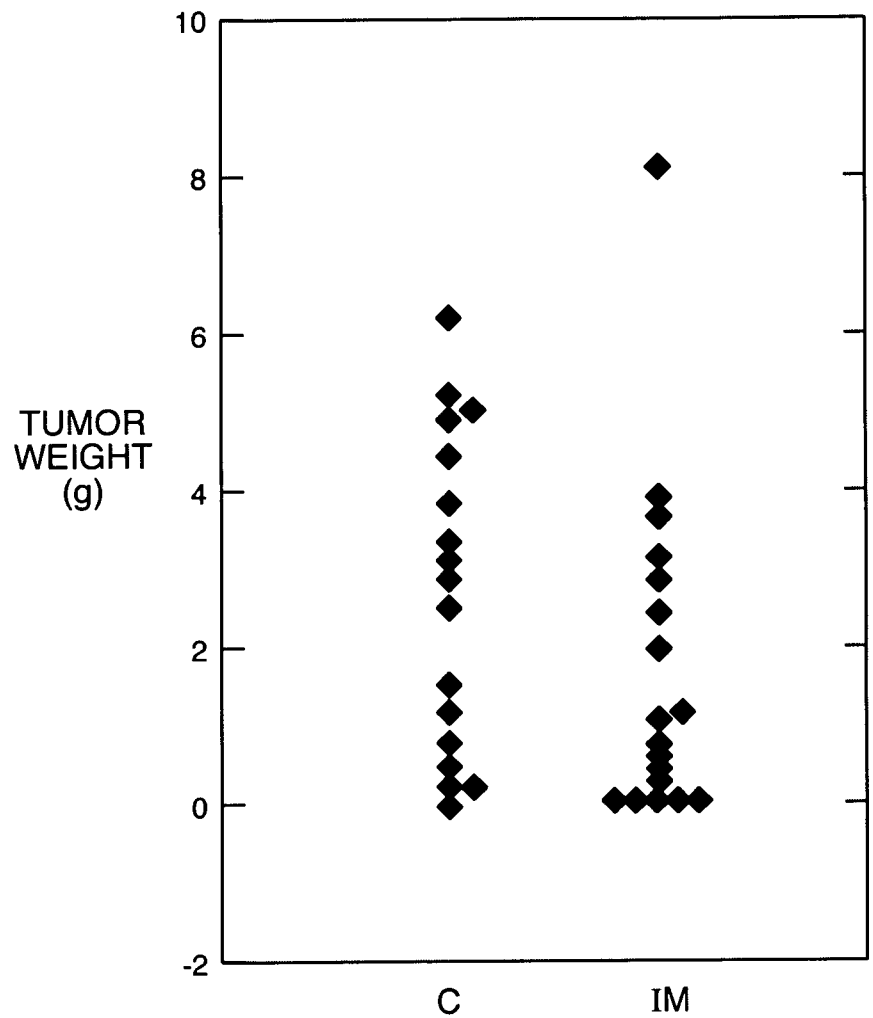
FIG. 14 compares the results of immunizing baby rats to XC tumor cells with rat serum prepared against the fusion protein MN glutathione S-transferase (GEX-3X-MN) (the IM group) with the results of immunizing baby rats with control rat sera (the C group). Each point on the graph represents the tumor weight of a tumor from one rat. Example 14 details those experiments.
Figure 16:
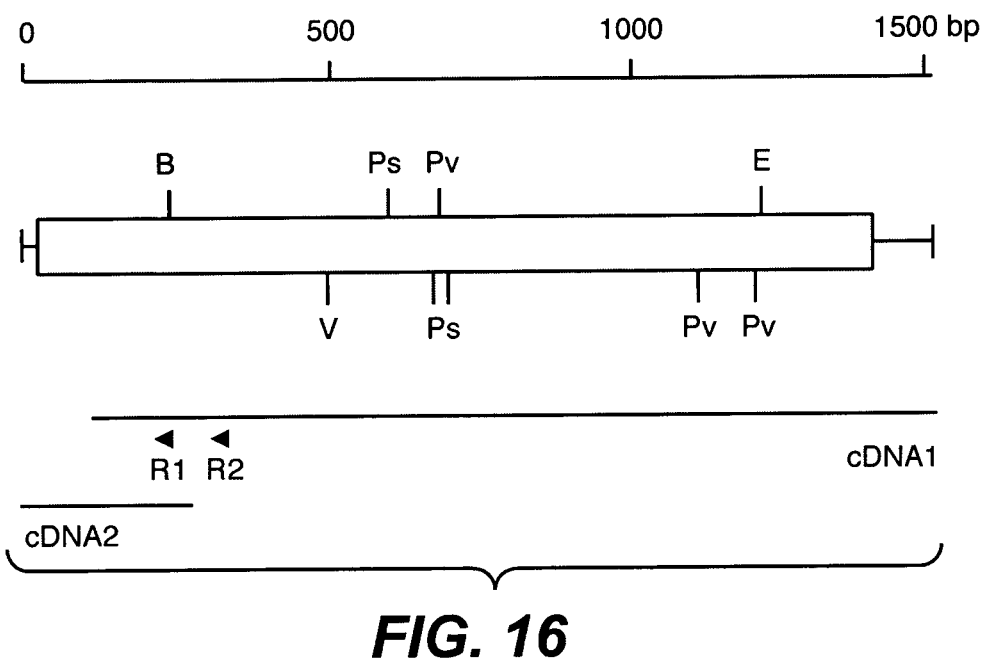
FIG. 16 is a restriction map of the full-length MN cDNA. The open reading frame is shown as an open box. The thick lines below the restriction map illustrate the sizes and positions of two overlapping cDNA clones. The horizontal arrows indicate the positions of primers R1 [SEQ. ID. NO.: 7] and R2 [SEQ. ID. NO.: 8] used for the 5' end RACE. Relevant restriction sites are BamHI (B), EcoRV (V), EcoRI (E), PstI (Ps), PvuII (Pv).

Four weeks later, the rats were sacrificed, and their tumors weighed. The results are shown in FIG. 14. Each point on the graph represents a tumor from one rat. The difference between the two groups—C and IM—was significant by Mann-Whitney rank test (U=84, α<0.025). The results indicate that the IM group of baby rats developed tumors about one-half the size of the controls, and 5 of the 18 passively immunized rats developed no tumor at all, compared to 1 of 18 controls.

Example 15

Expression of Full-Length MN cDNA in NIH 3T3 Cells

The role of MN in the regulation of cell proliferation was studied by expressing the full-length cDNA in NIH 3T3 cells. That cell line was chosen since it had been used successfully to demonstrate the phenotypic effect of a number of proto-oncogenes [Weinberg, R. A., *Cancer Res.*, 49: 3713 (1989); Hunter, T., *Cell*, 64: 249 (1991)]. Also, NIH 3T3 cells express no endogenous MN-related protein that is detectable by Mab M75.

The full length MN cDNA was obtained by ligation of the two cDNA clones using the unique BamHI site and subcloned from pBluescript into KpnI-SacI sites of the expression vector pSG5C. pSG5C was kindly provided by Dr. Richard Kettman [Department of Molecular Biology, Faculty of Agricultural Sciences, B-5030 Gembloux, Belgium]. pSG5C was derived from pSG5 [Stratagene] by inserting a polylinker consisting of a sequence having several neighboring sites for the following restriction enzymes: EcoRI, XhoI, KpnI, BamHI, SacI, 3 times TAG stop codon and BglII.

The recombinant pSG5C-MN plasmid was co-transfected in a 10:1 ratio (10 μg: 1 μg) with the pSV2neo plasmid [Southern and Berg, *J. Mol. Appl. Genet.* 1: 327 (1982)] which contains the neo gene as a selection marker. The co-transfection was carried out by calcium phosphate precipitation method [Mammalian Transfection Kit; Stratagene] into NIH 3T3 cells plated a day before at a density of $1 \times 10^5$ per 60 mm dish. As a control, pSV2neo was co-transfected with empty pSG5C.

Transfected cells were cultured in DMEM medium supplemented with 10% FCS and 600 μg ml$^{-1}$ of G418 [Gibco BRL] for 14 days. The G418-resistant cells were clonally selected, expanded and analysed for expression of the transfected cDNA by Western blotting using iodinated Mab M75.

For an estimation of cell proliferation, the clonal cell lines were plated in triplicates ($2 \times 10^4$ cells/well) in 24-well plates and cultivated in DMEM with 10% FCS and 1% FCS, respectively. The medium was changed each day, and the cell number was counted using a hemacytometer.

To determine the DNA synthesis, the cells were plated in triplicate in 96-well plate at a density of $10^4$/well in DMEM with 10% FCS and allowed to attach overnight. Then the cells were labeled with $^3$H-thymidine for 24 hours, and the incorporated radioactivity was counted.

For the anchorage-independent growth assay, cells ($2 \times 10^4$) were suspended in a 0.3% agar in DMEM containing 10% FCS and overlaid onto 0.5% agar medium in 60 mm dish. Colonies grown in soft agar were counted two weeks after plating.

Several clonal cell lines constitutively expressing both 54 and 58 kd forms of MN protein in levels comparable to those found in LCMV-infected HeLa cells were obtained. Selected MN-positive clones and negative control cells (mock-transfected with an empty pSG5C plasmid) were subjected to further analyses directed to the characterization of their phenotype and growth behavior.

Figure 23A:
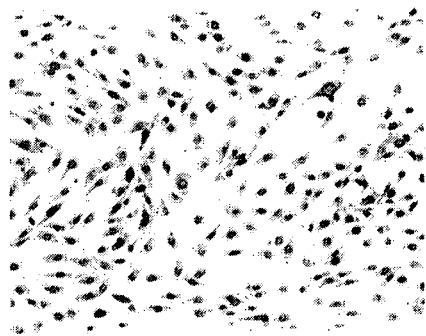
FIG. 23 shows the morphology and growth kinetics of control (a, c, e and g) and MN-expressing (b, d, f and h) NIH 3T3 cells. The micrographs are of methanol fixed and Giemsa stained cells at a magnification ×100. Cells were grown to confluency (a, b), or as individual colonies in Petri dishes (c, d) and in soft agar (e, f). The (g) and (h) graphs provide growth curves of cells cultured in DMEM medium containing respectively, 10% and 1% FCS. The mean values of triplicate determinations were plotted against time.
Figure 23B:
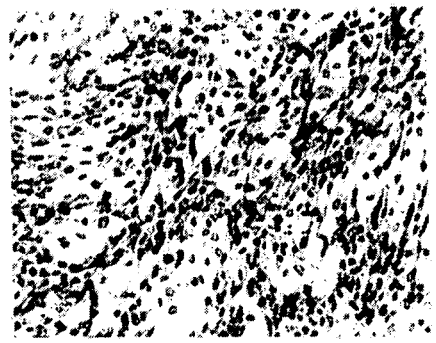
Figure 23C:
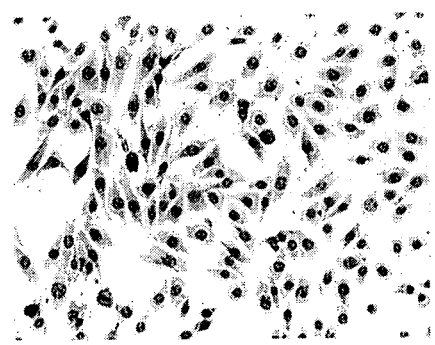
Figure 23D:
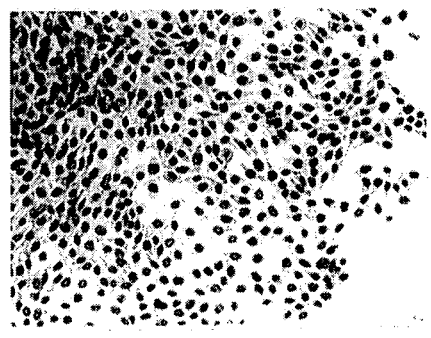
Figure 23E:
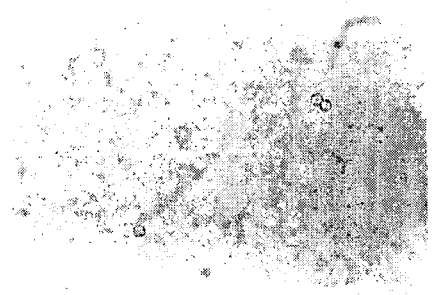
Figure 23F:
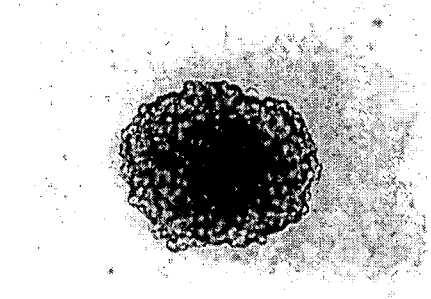
Figure 23G:
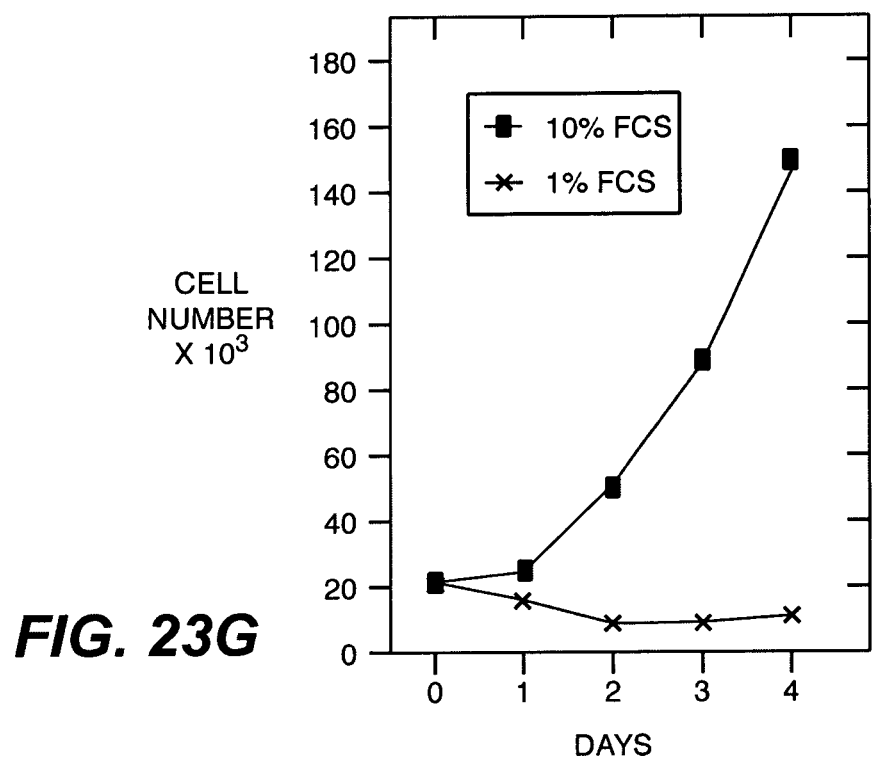
Figure 23H:
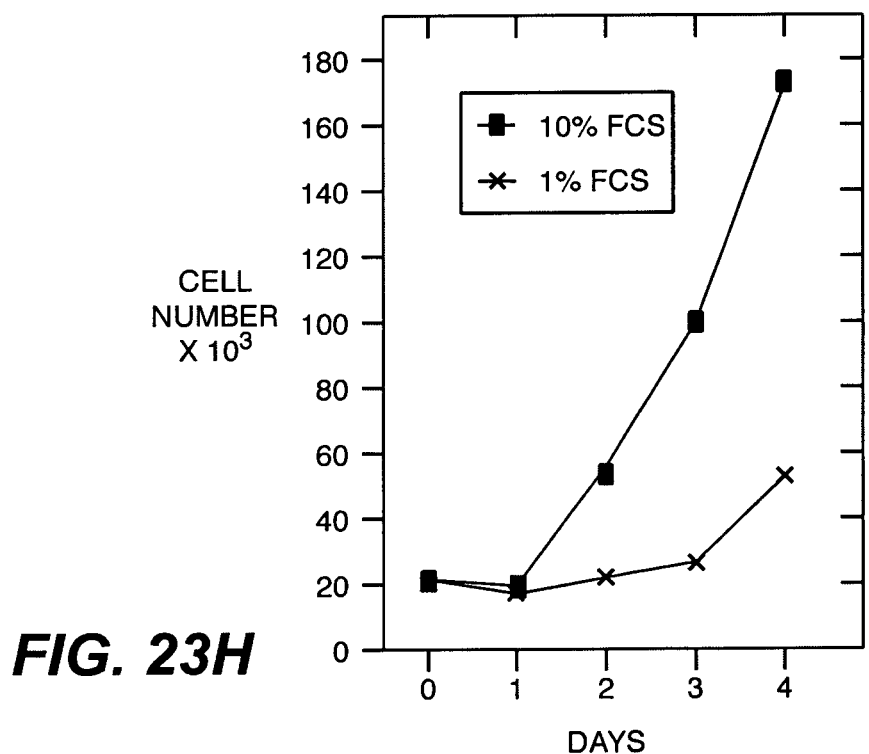

The MN-expressing NIH 3T3 cells displayed spindle-shaped morphology, and increased refractility; they were less adherent to the solid support and smaller in size. The control (mock transfected cells) had a flat morphology, similar to parental NIH 3T3 cells. In contrast to the control cells that were aligned and formed a monolayer with an ordered pattern, the cells expressing MN lost the capacity for growth arrest and grew chaotically on top of one another (FIG. 23a-d). Correspondingly, the MN-expressing cells were able to reach significantly higher (more than 2×) saturation densities (Table 3) and were less dependent on growth factors than the control cells (FIG. 23g-h).

MN transfectants also showed faster doubling times (by 15%) and enhanced DNA synthesis (by 10%), as determined by the amount of [$^3$H]-thymidine incorporated in comparison to control cells. Finally, NIH 3T3 cells expressing MN protein grew in soft agar. The diameter of colonies grown for 14 days ranged from 0.1 to 0.5 mm (FIG. 23f); however, the cloning efficiency of MN transfectants was rather low (2.4%). Although that parameter of NIH 3T3 cells seems to be less affected by MN than by conventional oncogenes, all other data are consistent with the idea that MN plays a role in cell growth control.

TABLE 3

Growth Properties of NIH 3T3 Cells Expressing MN Protein

| Transfected DNA | pSG5C/ pSV2neo | pSG5C-MN/ pSV2neo |
|---|---|---|
| Doubling time$^a$ (hours) | 27.9 ± 0.5 | 24.1 ± 1.3 |
| Saturation density$^b$ (cells × $10^4$/cm$^2$) | 4.9 ± 0.2 | 11.4 ± 0.4 |
| Cloning efficiency (%)$^c$ | <0.01 | 2.4 ± 0.2 |

$^a$For calculation of the doubling time, the proliferation rate of exponentially growing cells was used.
$^b$The saturation cell density was derived from the cell number 4 days after reaching confluency.
$^c$Colonies greater than 0.1 mm in diameter were scored at day 14. Cloning efficiency was estimated as a percentage of colonies per number of cells plated, with correction for cell viability.

Example 16

Acceleration of G1 Transit and Decrease in Mitomycin C Sensitivity Caused by MN Protein For the experiments described in this example, the stable MN transfectants of NIH 3T3 cells generated as described in Example 15 were used. Four selected MN-positive clones and four control mock-transfected clones were either used individually or in pools.

Flow cytometric analyses of asynchronous cell populations. For the results shown in FIG. 24(a), cells that had been grown in dense culture were plated at $1 \times 10^6$ cells per 60 mm dish. Four days later, the cells were collected by trypsinization, washed, resuspended in PBS, fixed by dropwise addition of 70% ethanol and stained by propidium iodine solution containing RNase. Analysis was performed by FACStar using DNA cell cycle analysis software. [Becton Dickinson; Franklin Lakes, N.J. (USA)].

For the analyses shown in FIGS. 24(b) and (c), exponentially growing cells were plated at $5 \times 10^5$ cells per 60 mm dish and analysed as above 2 days later. Forward light scatter was used for the analysis of relative cell sizes. The data were evaluated using Kolmogorov-Smirnov test [Young, *J. Histochem. Cytochem.*, 25: 935 (1977)]. D is the maximum difference between summation curves derived from histograms. D/s(n) is a value which indicates the similarity of the compared curves (it is close to zero when curves are similar).

The flow cytometric analyses revealed that clonal populations constitutively expressing MN protein showed a decreased percentage of cells in G1 phase and an increased percentage of cells in G2-M phases. Those differences were more striking in cell populations grown throughout three passages in high density cultures [FIG. 24(a)], than in exponentially growing subconfluent cells [FIG. 24(b)]. That observation supports the idea that MN protein has the capacity to perturb contact inhibition.

Also observed was a decrease in the size of MN expressing cells seen in both exponentially proliferating and high density cultures. It is possible that the MN-mediated acceleration of G1 transit is related to the above-noted shorter doubling time (by about 15%) of exponentially proliferating MN-expressing NIH 3T3 cells. Also, MN expressing cells displayed substantially higher saturation density and lower serum requirements than the control cells. Those facts suggest that MN-transfected cells had the capacity to continue to proliferate despite space limitations and diminished levels of serum growth factors, whereas the control cells were arrested in G1 phase.

Limiting conditions. The proliferation of MN-expressing and control cells was studied both in optimal and limiting conditions. Cells were plated at $2 \times 10^4$ per well of 24-well plate in DMEM with 10% FCS. The medium was changed at daily intervals until day 4 when confluency was reached, and the medium was no longer renewed. Viable cells were counted in a hemacytometer at appropriate times using trypan blue dye exclusion. The numbers of cells were plotted versus time wherein each plot point represents a mean value of triplicate determination.

The results showed that the proliferation of MN expressing and control cells was similar during the first phase when the medium was renewed daily, but that a big difference in the number of viable cells occurred after the medium was not renewed. More than half of the control cells were not able to withstand the unfavorable growth conditions. In contrast, the MN-expressing cells continued to proliferate even when exposed to increasing competition for nutrients and serum growth factors.

Those results were supported also by flow cytometric analysis of serum starved cells grown for two days in medium containing 1% FCS. While 83% of control cells accumulated in G0-G1 phase (S=5%, G2-M=12%), expression of MN protein partially reversed the delay in G1 as indicated by cell cycle distribution of MN transfectants (G0-G1=65%, S=10%, G2-M=26%). The results of the above-described experiments suggest that MN protein might function to release the G1/S checkpoint and allow cells to proliferate under unfavorable conditions.

MMC. To test that assumption, unfavorable conditions were simulated by treating cells with the DNA damaging drug mitomycin C (MMC) and then following their proliferation and viability. The mechanism of action of MMC is thought to result from its intracellular activation and subsequent DNA alkylation and crosslinking [Yier and Szybalski, *Science*, 145: 55 (1964)]. Normally, cells respond to DNA damage by arrest of their cell cycle progression to repair defects and prevent acquisition of genomic instability. Large damage is accompanied by marked cytotoxicity. However, many studies [for example, Peters et al., *Int. J. Cancer*, 54: 450 (1993)] concern the emergence of drug resistant cells both in tumor cell populations and after the introduction of oncogenes into nontransformed cell lines.

The response of MN-transfected NIH 3T3 cells to increasing concentrations of MMC was determined by continuous [$^3$H]-thymidine labeling. Cells were plated in 96-well microtiter plate concentration of $10^4$ per well and incubated overnight in DMEM with 10% FCS to attach. Then the growth medium was replaced with 100 µl of medium containing increasing concentrations of MMC from 1 µl/ml to 32 µg/ml. All the drug concentrations were tested in three replicate wells. After 5 hours of treatment, the MMC was removed, cells were washed with PBS and fresh growth medium without the drug was added. After overnight recovery, the fractions of cells that were actively participating in proliferation was determined by continuous 24-hr labeling with [$^3$H]-thymidine. The incorporation by the treated cells was compared to that of the control, untreated cells, and the proliferating fractions were considered as a percentage of the control's incorporation.

The viability of the treated cells was estimated three days later by a CellTiter 96 AQ Non-Radioactive Cell Proliferation Assay [Promega] which is based on the bioreduction of methotrexate (MTX) into a water soluble formazan that absorbs light at 490 nm. The percentage of surviving cells was derived from the values of absorbance obtained after substraction of background.

The control and MN-expressing NIH 3T3 cells showed remarkable differences in their responses to MMC. The sensitivity of the MN-transfected cells appeared considerably lower than the control's in both sections of the above-described experiments. The results suggested that the MN-transfected cells were able to override the negative growth signal mediated by MMC.

ATCC Deposits. The material listed below was deposited with the American Type Culture Collection (ATCC) at 10801 University Blvd., Manassas, Va. 20110-2209 (USA). The deposits were made under the provisions of the Budapest Treaty on the International Recognition of Deposited microorganisms for the Purposes of Patent Procedure and Regulations thereunder (Budapest Treaty). Maintenance of a viable culture is assured for thirty years from the date of deposit. The organism will be made available by the ATCC under the terms of the Budapest Treaty, and subject to an agreement between the Applicants and the ATCC which assures unrestricted availability of the deposited hybridomas to the public upon the granting of patent from the instant application. Availability of the deposited strain is not to be construed as a license to practice the invention in contravention of the rights granted under the authority of any Government in accordance with its patent laws.

| Hybridoma | Deposit Date | ATCC # |
|---|---|---|
| VU-M75 | Sep. 17, 1992 | HB 11128 |
| MN 12.2.2 | Jun. 9, 1994 | HB 11647 |

The description of the foregoing embodiments of the invention have been presented for purposes of illustration and description. They are not intended to be exhaustive or to limit the invention to the precise form disclosed, and obviously many modifications and variations are possible in light of the above teachings. The embodiments were chosen and described in order to explain the principles of the invention and its practical application to enable thereby others skilled in the art to utilize the invention in various embodiments and with various modifications as are suited to the particular use contemplated.

All references cited herein are hereby incorporated by reference.

What we claim is:

1. An isolated monoclonal antibody which specifically binds to an MN protein or to an MN polypeptide,
   wherein said MN protein or MN polypeptide is encoded by a nucleic acid that comprises a polynucleotide of SEQ ID NO:5, or an antigen-binding fragment of said antibody, and
   wherein
      said antibody is not antibody M75 that is secreted by hybridoma VU-M75, which was deposited at the American Type Culture Collection (ATCC) under ATCC No. RB 11128 and
      said antibody is not antibody MN12 that is secreted by hybridoma MN 12.2.2, which was deposited at the American Type culture Collection (ATCC) under ATCC No. HE 11647.

2. The antibody of claim 1 that is conjugated to a toxin.

3. The antibody of claim 1 that is conjugated to a chemotherapeutic drug.

4. An isolated antibody which specifically binds to an MN protein or to an MN polypeptide,
   wherein said MN protein or MN polypeptide is encoded by a nucleic acid that comprises a polynucleotide of SEQ ID NO:5,
   wherein said antibody is prepared using a phage library that displays sequences of heavy-chain variable ($V_H$) and/or light-chain variable ($V_L$) regions of immunoglobulin genes screened for specific binding to said MN protein or said MN polypeptide, or an antigen-binding fragment of said antibody, and
   wherein
      said antibody is not antibody M75 that is secreted by hybridoma VU-M75, which was deposited at the American Type Culture Collection (ATCC) under ATCC No. RB 11128 and
      said antibody is not antibody MN12 that is secreted by hybridoma MN 12.2.2, which was deposited at the American Type culture Collection (ATCC) under ATCC No. HE 11647.

5. The antibody of claim 4 that is conjugated to a toxin.

6. The antibody of claim 4 that is conjugated to a chemotherapeutic drug.

7. The antibody of claim 4 wherein said MN protein has the amino acid sequence of SEQ ID NO: 6.

8. The antibody of claim 4 wherein said MN polypeptide has an amino acid sequence from SEQ ID NO: 6.

9. The antibody of claim 4 which is an antigen-binding antibody fragment.

10. The antibody of claim 9 which comprises an antigen binding region.

11. The antibody of claim 9 which comprises a variable heavy chain ($V_H$) region and a variable light chain ($V_L$) region.

12. The antibody of claim 11 which comprises the hypervariable regions of said $V_H$ and $V_L$ regions.

13. An isolated MN-specific antibody that specifically binds to an MN protein which has the amino acid sequence of or from SEQ ID NO: 6,
   wherein said isolated MN-specific antibody is prepared using a phage library that displays sequences of heavy-chain variable ($V_H$) and/or light-chain variable ($V_L$) regions of immunoglobulin genes screened for specific binding to said MN protein, or an antigen-binding fragment of said antibody, and
   wherein
      said antibody is not antibody M75 that is secreted by hybridoma VU-M75, which was deposited at the American Type Culture Collection (ATCC) under ATCC No. RB 11128 and
      said antibody is not antibody MN12 that is secreted by hybridoma MN 12.2.2, which was deposited at the American Type culture Collection (ATCC) under ATCC No. HE 11647.

14. The antibody of claim 13 that is conjugated to a toxin.

15. The antibody of claim 13 that is conjugated to a chemotherapeutic drug.

16. The antibody of claim 13 which is an antigen-binding antibody fragment.

17. The antibody of claim 16 which comprises an antigen binding region.

18. The antibody of claim 16 which comprises a variable heavy chain ($V_H$) region and a variable light chain ($V_L$) region.

19. The antibody of claim 18 which comprises the hypervariable regions of said $V_H$ and $V_L$ regions.

20. The antibody of claim 4 which is linked to an imaging agent.

21. The antibody of claim 13 which is linked to an imaging agent.

22. A vector comprising an expression control sequence operatively linked to a nucleic acid encoding a variable light chain and/or a variable heavy chain, or one or more fragments from a variable light ($V_L$) chain and/or from a variable heavy ($V_H$) chain, of an antibody or an antigen-binding antibody fragment that specifically binds to an MN protein or to an MN polypeptide, wherein said MN protein or MN polypeptide is encoded by a nucleic acid that comprises a polynucleotide of SEQ ID NO:5, wherein said antibody or antibody fragment specifically binds to the MN protein having the amino acid sequence of SEQ ID NO: 6.

23. The vector of claim 22 wherein said nucleic acid encodes both a variable light chain and a variable heavy chain of an antibody that specifically binds said MN protein or MN polypeptide.

24. The vector of claim 22, wherein said nucleic acid encodes hypervariable regions of the variable heavy chain and/or hypervariable regions of the variable light chain from said MN-specific antibody or antibody fragment.

25. The vector of claim 22, wherein said antibody or antibody fragment is selected from the group consisting of an Fab fragment, an F(ab')$_2$ fragment, a single-chain antibody, a bispecific antibody, and a chimeric antibody.

26. The vector of claim 22, wherein said antibody or antibody fragment specifically binds an epitope within the N-terminal domain of MN protein, wherein said N-terminal domain has an amino acid sequence consisting of amino acids 38-414 of SEQ ID NO: 6.

27. The vector of claim 22, wherein said antibody or antibody fragment specifically binds an epitope within the transmembrane domain of MN protein, wherein said transmembrane domain has an amino acid sequence consisting of amino acids 415-434 SEQ ID NO: 6.

28. The vector of claim 22, wherein said antibody or antibody fragment specifically binds an epitope within the C-terminal domain of MN protein, wherein said C-terminal domain has an amino acid sequence consisting of amino acids 435-459 of SEQ ID NO: 6.

29. The vector of claim 22, wherein said antibody or antibody fragment is first isolated using a phage library that displays sequences of heavy-chain variable and/or light-chain variable regions of immunoglobulin genes screened for specific binding to said MN protein or said MN polypeptide.

\* \* \* \* \*